United States Patent [19]

Binger et al.

[11] Patent Number: 5,661,015

[45] Date of Patent: Aug. 26, 1997

[54] RECOMBINANT COCCIDIOSIS VACCINES

[75] Inventors: Mary-Helen Binger, Hopewell, N.J.; Richard Anthony Chizzonite, South Kent, Conn.; Richard Allen Kramer, West Orange, N.J.; Peter Thomas Lomedico, Montclair, N.J.; Stephen J. McAndrew, Meriden, Conn.; Werner Altenburger, Muenchenstein, Switzerland

[73] Assignee: Hoffmann-La Roche Inc., Nutley, N.J.

[21] Appl. No.: 812,349

[22] Filed: Dec. 20, 1991

Related U.S. Application Data

[63] Continuation-in-part of Ser. No. 202,721, Jun. 3, 1988, abandoned.

[51] Int. Cl.⁶ ................................................ C12N 15/00
[52] U.S. Cl. .............. 435/172.3; 435/69.3; 435/320.1; 435/252.33; 435/252.31; 435/419; 435/325; 530/350; 935/12; 536/23.7
[58] Field of Search .............. 424/85.8, 88; 435/69.3, 435/69.6, 240.27, 172.3; 530/350, 388.8, 389.8; 935/12, 15

[56] References Cited

U.S. PATENT DOCUMENTS

| | | | |
|---|---|---|---|
| 4,639,372 | 1/1987 | Murray et al. | 424/88 |
| 4,650,676 | 3/1987 | Schenkel et al. | 424/88 |
| 4,710,377 | 12/1987 | Schenkel et al. | 424/88 |
| 4,874,705 | 10/1989 | Andrews et al. | . |
| 5,118,080 | 6/1992 | Andrews et al. | 435/69.3 |
| 5,187,080 | 2/1993 | Andrews | 435/69.3 |
| 5,273,901 | 12/1993 | Jacobson et al. | 435/243 |
| 5,496,550 | 3/1996 | Wallach et al. | 424/184.1 |

FOREIGN PATENT DOCUMENTS

| | | |
|---|---|---|
| 135 712 | 4/1985 | European Pat. Off. . |
| 164 176 | 12/1985 | European Pat. Off. . |
| 167 443 | 1/1986 | European Pat. Off. . |
| 0231537 | 8/1987 | European Pat. Off. . |
| 86/00528 | 1/1986 | WIPO ............................ C12N 7/00 |

OTHER PUBLICATIONS

Drofous–Jachelka, Mol. Bioch. Parasitology 30:233–242 "ID and Charge of cDNA Clones Encoding Antigens of *E. tenella*" (1988).

Smith et al., Gene 25:21 (1983).

Zemcik et al., Immunol. Methods 91:265 (1986).

Moss et al., Ann. Rev. Immunol. 5:305 (1987).

Jenkins and Dame, Fed. Proc. 46(3) abstract 2696 (1987) p. 778.

Wisher, J. Cell. Biochem. 7 (Suppl.) 12th Ann. Mtg. UCLA abstract 0059 (1983) p. 25.

Clarke et al., Mol. and Biochem. Para. 22:79–87 (1987).

Jenkins et al., Mol. and Biochem. Para. 32:153–162 (1989).

Binger et al., J. Cell. Biochem. (Suppl.) 15th Ann. Mt. UCLA abstract C83 (1986) p. 144.

*Primary Examiner*—James C. Housel
*Assistant Examiner*—Ginny Allen Portner
*Attorney, Agent, or Firm*—George W. Johnston; William H. Epstein; Catherine R. Smith

[57] ABSTRACT

This invention provides DNA sequences coding for Eimeria surface antigens, recombinant vectors containing such DNA sequences, transformed microorganisms containing such vectors, and methods for producing the antigens using the transformed microorganisms. Methods are also provided for protecting poultry against coccidiosis using the Eimeria surface antigens. The surface antigens can be administered for such protection either as purified proteins or in the form of DNA encoding the proteins in a suitable viral vector such as vaccinia virus.

5 Claims, 47 Drawing Sheets

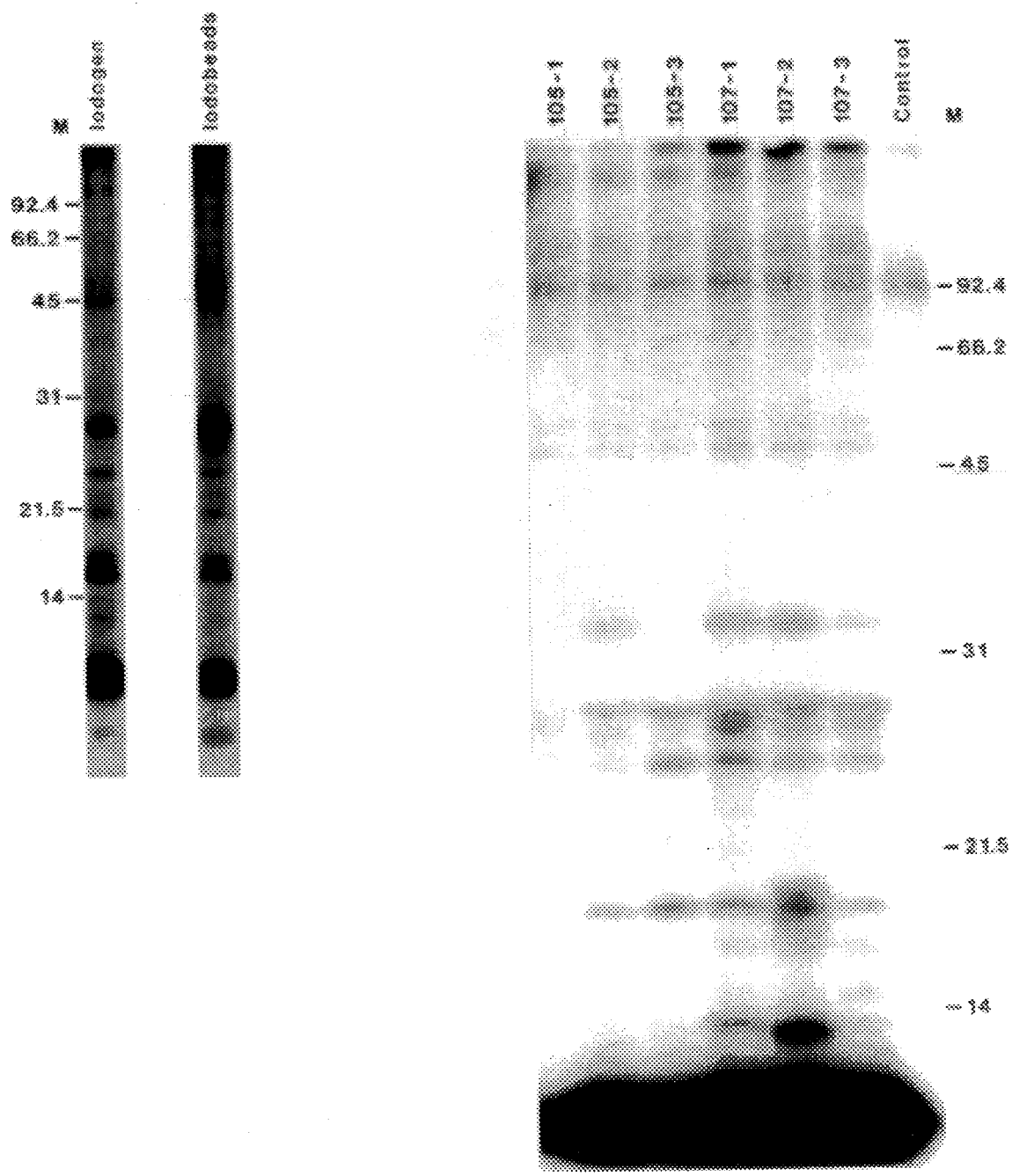
F I G. 4

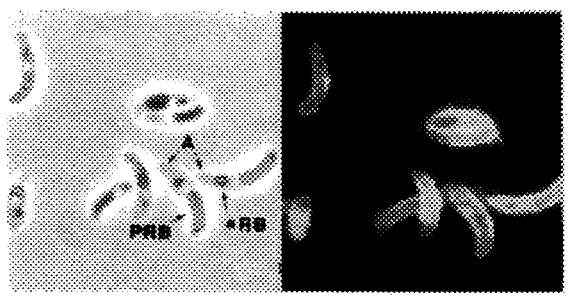 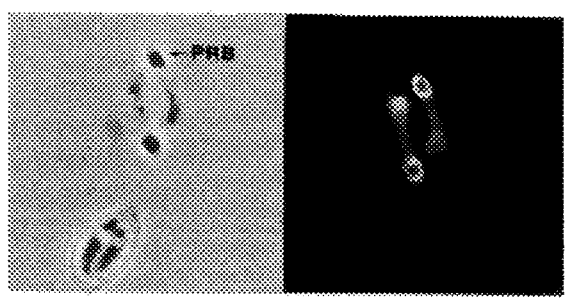
FIG. 6A  FIG. 6B
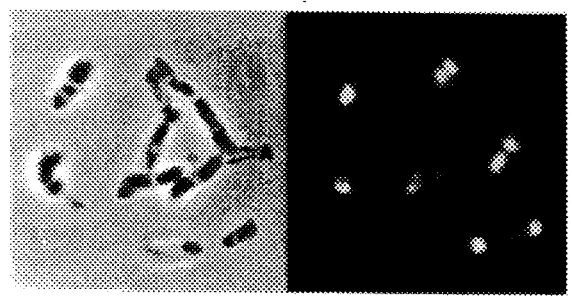 
FIG. 6C  FIG. 6D

7D4
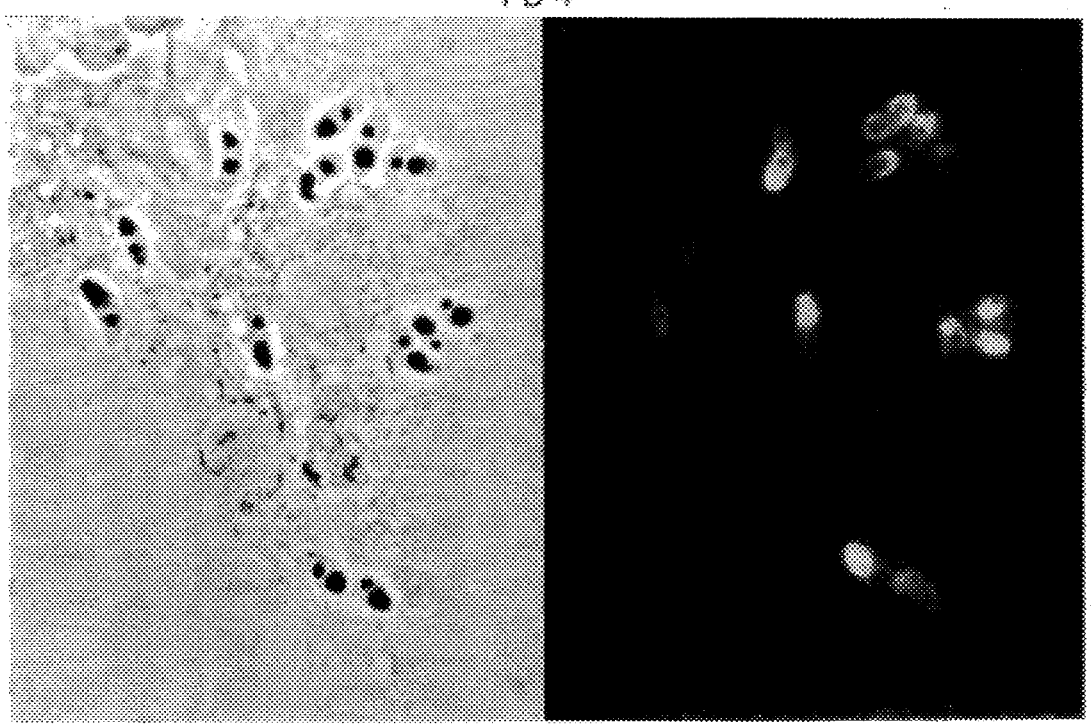
3hrs
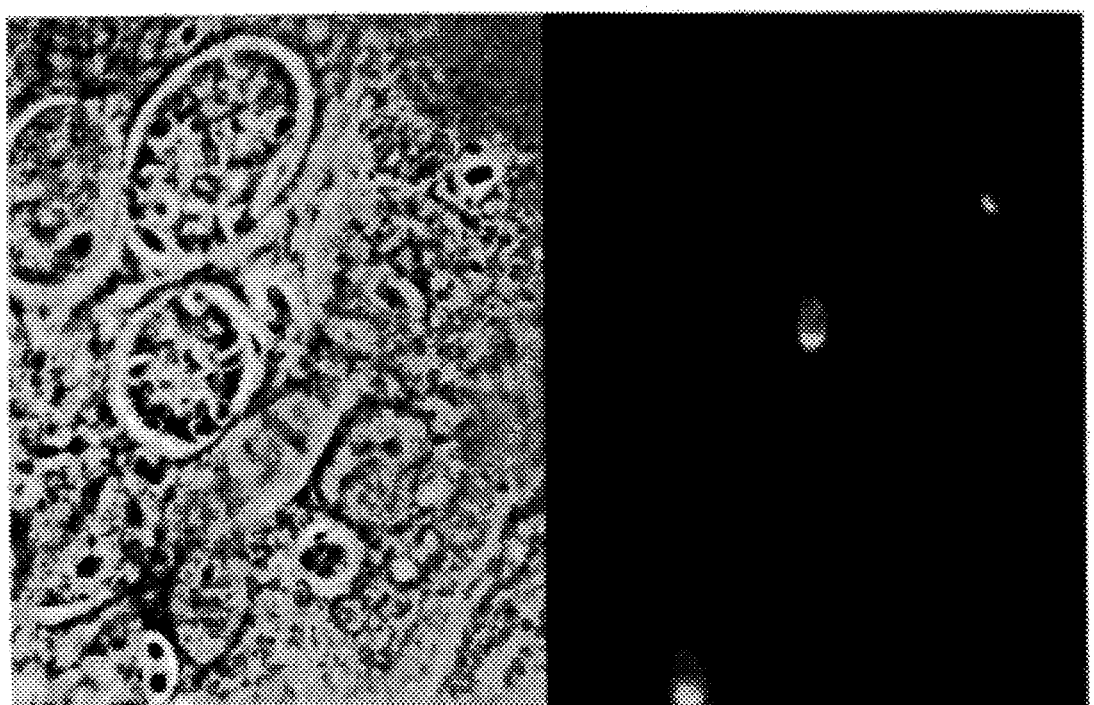
60hrs
F I G. 7A

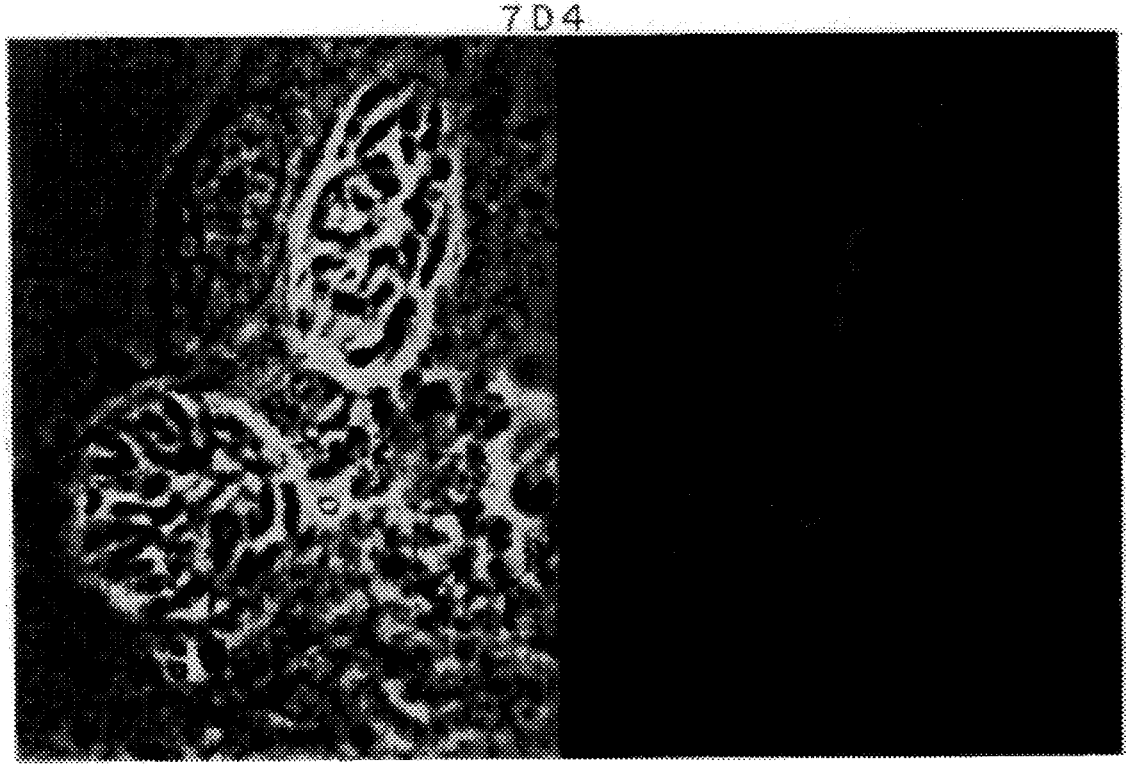
100hrs
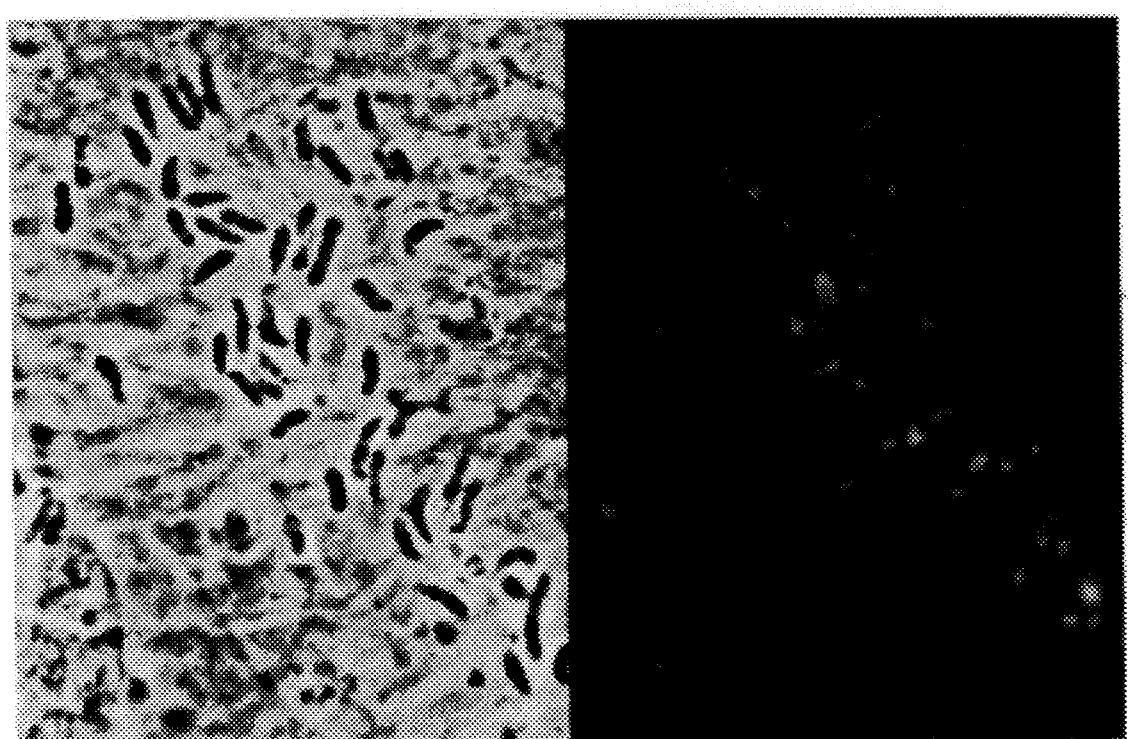
120hrs
FIG. 7B

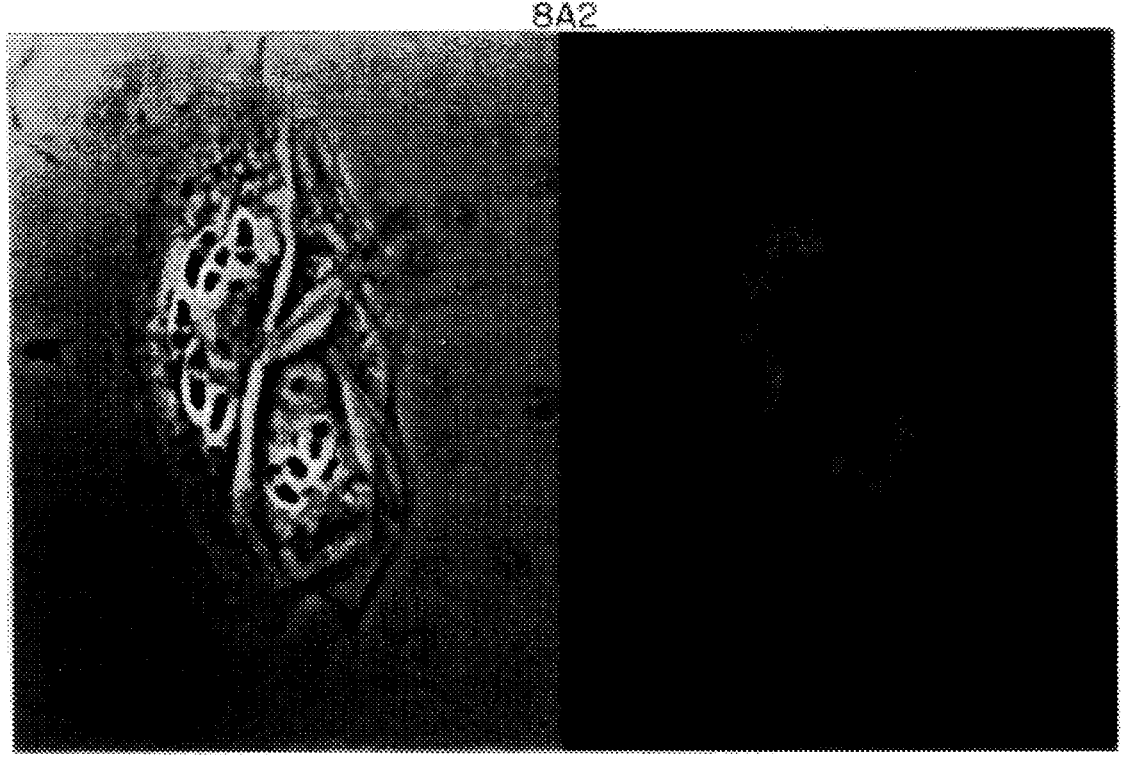
FIG. 7C

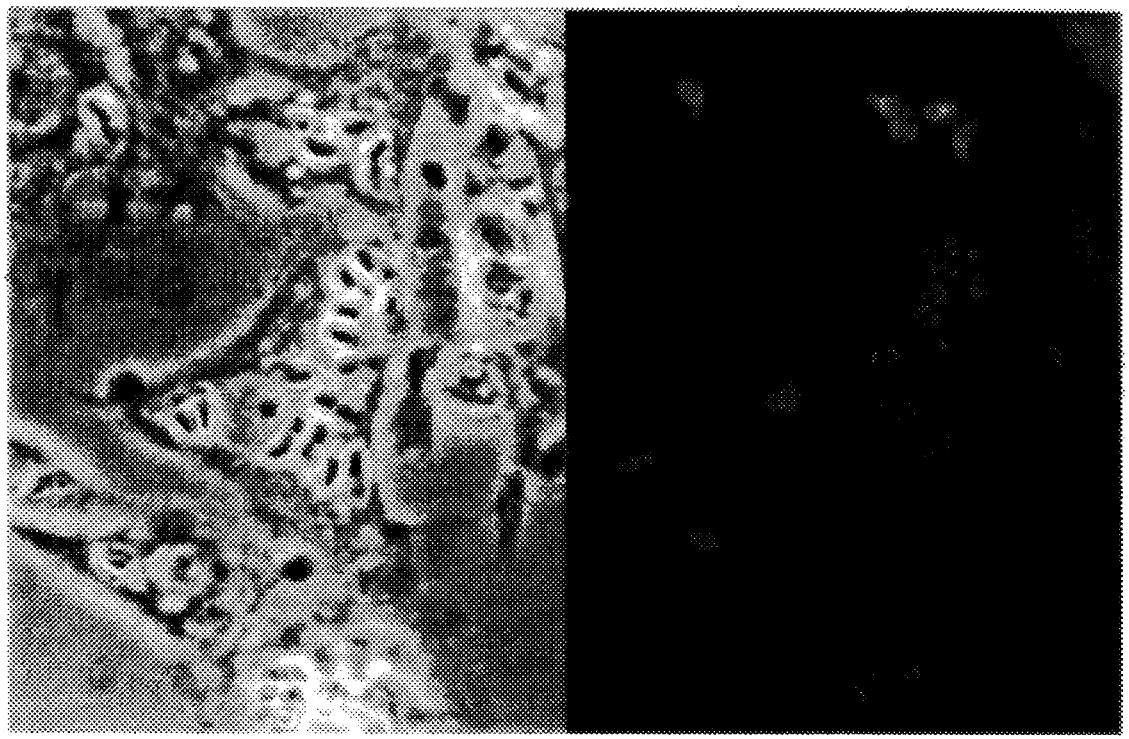
782     3hrs
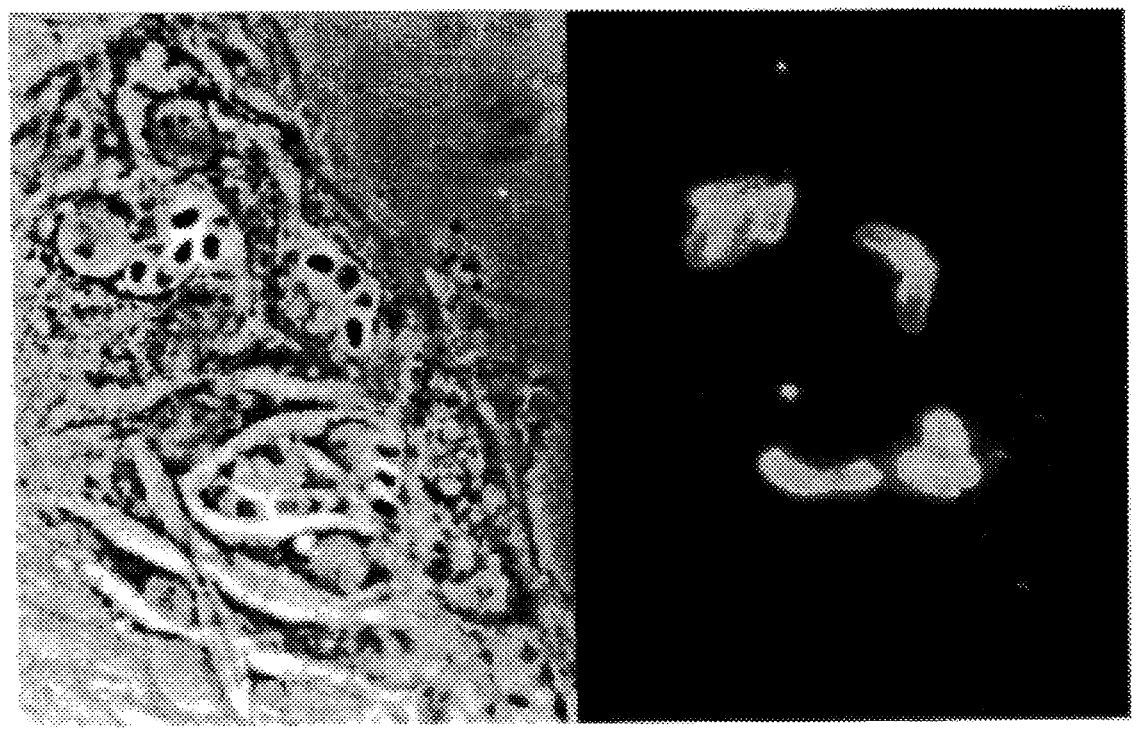
15A3    19hrs
F I G. 7D

14B1
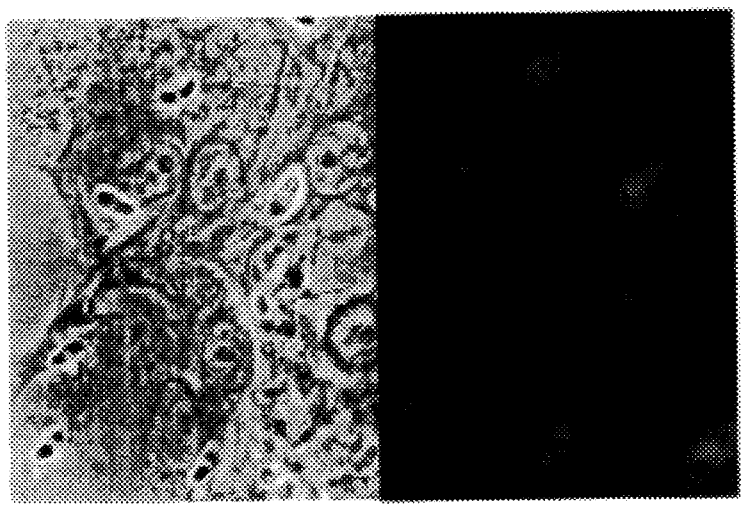
16 hrs
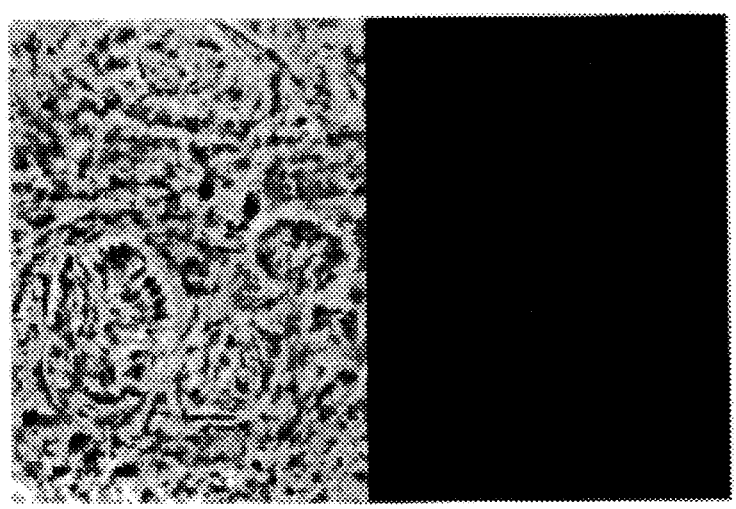
100 hrs
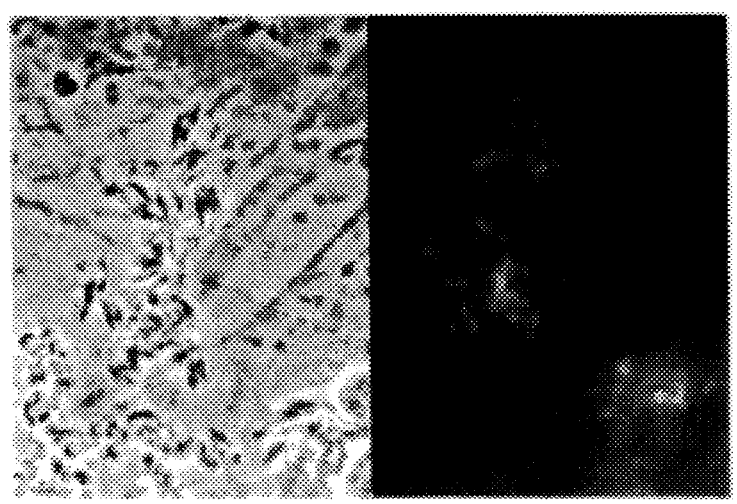
120 hrs
FIG. 8A

19D6
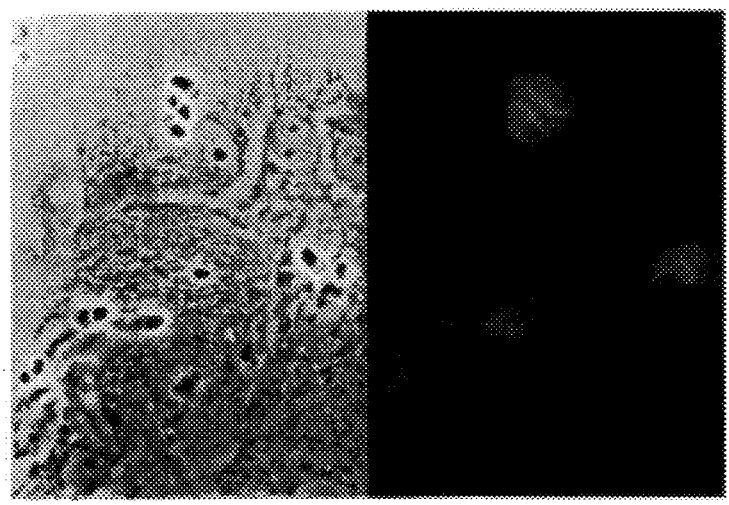
3hrs
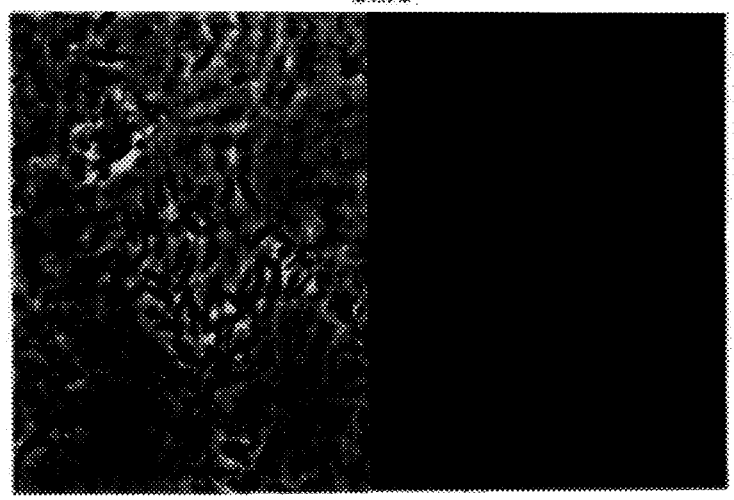
120hrs
IMMUNE CHICK SERA
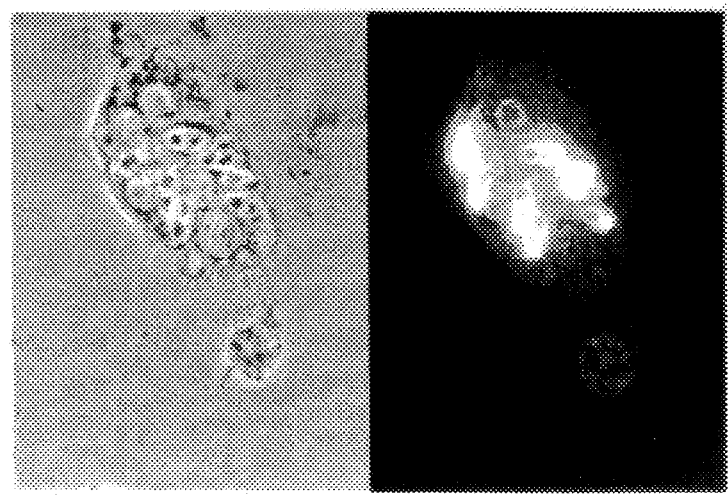
3hrs
FIG.8B

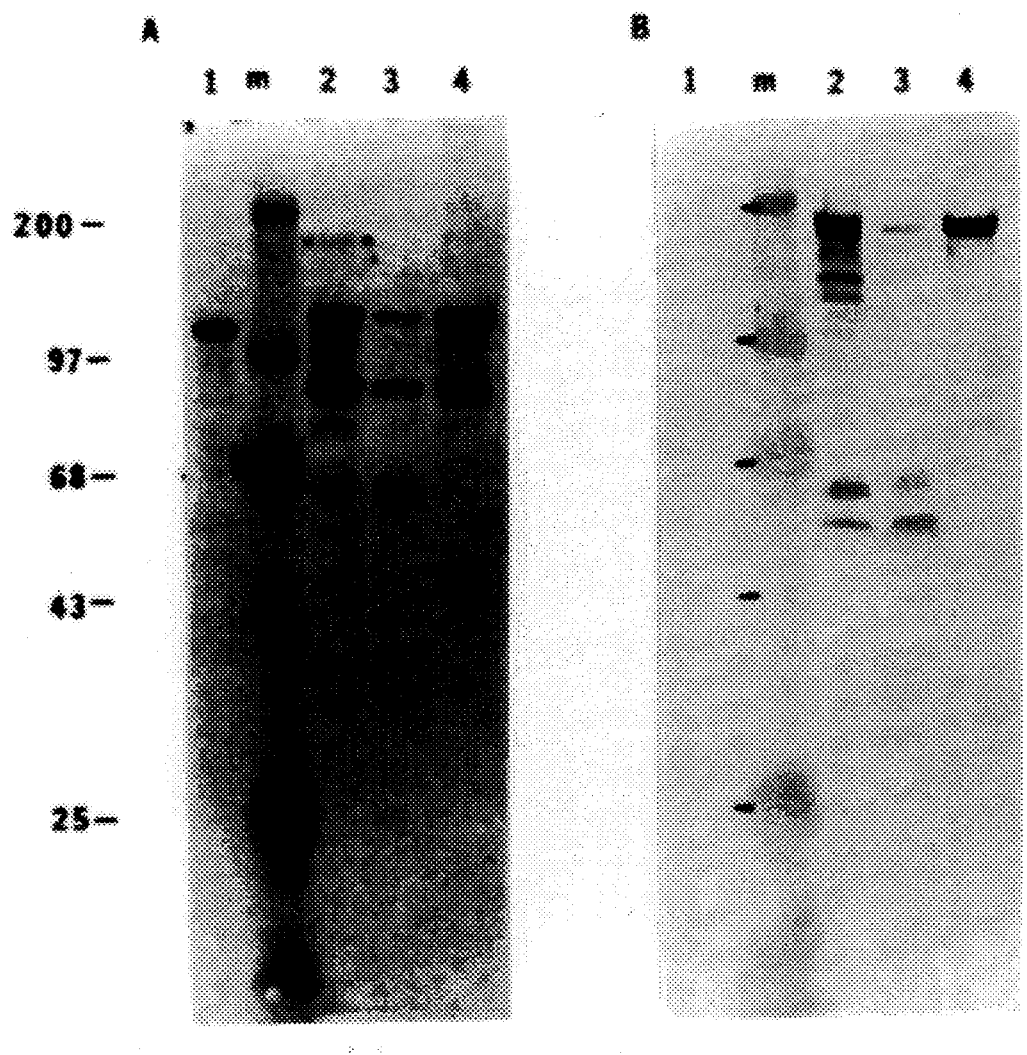
F I G. 10

```
       10         20         30         40         50
GAATTCCCTC CAACTCTTCG CGACTCTCTC TCTCTCGCCC CAACTTTTTC 60         70         80         90        100
CCCCGCGCCC CGCAGCAGCA GCAGCAGCAG CAGCAGCAAA ATGGCAGACC 110        120        130        140        150
TCTTCAGCGG ACTCGTGGGC GGCGTCGTCG GCGCTGTTGC TGCAGCAGAT 160        170        180        190        200
TTGCCTGCGG AGGGCGAGAG GGCCCCCCGC CCCGCCCCCG GCACTGCCTG 210        220        230        240        250
GACTTGCTGC TGCAGCAAAC TGCAAGAAGG GGCCCGCGAG CTGGAGGGTT 260        270        280        290        300
TTGTGCAGCA GCTGAGTTTT GTTGCAGGGA AGCTGGCCTG CTGCCTGCGG 310        320        330        340        350
GTGGGGGCGG AGCAGCTGGC GCGCTGCGCT GCGGAGGGGC GGCTGCCCAG 360        370        380        390        400
CAGCAGCAGC AGCAGCAGCT GCTGCGCGCT GCGGAGGGGC GGCTGCCCAG 410        420        430        440        450
ACCTCGAGCA GAGCCTCGAG GCCGGCAAGC AGGGCGCGGA GTGCCTCTTG 460        470        480        490        500
AGGAGCAGCA AACTGGCCCT CGAGGCCCTC CTCGAGGGGG CCCGCGTTGC 510        520        530        540        550
AGCAACGCGG GGTTTGCTGC TGGTCGAGAG CAGCAAAGAC ACGGTGCTGC 560        570        580        590        600
GCAGCATTCC CCACACCCAG GAGAAGCTGG CTCAGGCCTA CAGTTCTTTC 610        620        630        640        650
CTGCGGGGCT ACCAGGGGGC AGCAGCGGGG AGGTCTCTGG GCTACGGGGC 660        670        680        690        700
CCCTGCTGCT GCTTACGGCC AGCAGCAGCA GCCCAGCAGC TACGGGGCGC 710        720        730        740        750
CCCCCGCCTC CAGCCAGCAG CCCTCCGGCT TCTTCTGGTA GCCCTGCAGC 760        770        780        790        800
AGCAGCAGCA GCAGCAGCAG CAGCAGCAGC GGCGGCGGCA GCCGCGGCGG 810        820        830        840        850
GGCCGGGGCG CCGCTGCAGC AACAGCAGCA GCCGCGGCGG CTAGCG3636

860        870        880        890        900
GAGCACTCGC AGGGAACTCC ACAGGCAGCG GGAGAGCAGC AGGGACGAGA
```

FIG. 14A

```
          910        920        930         940        950
    AGCAGGTCTA TGTAGCGCAG GCAGCAGCGC CAGCTGCAGC AGCAGCAGCA 960        970        980         990       1000
    GCAGCAGCAG CAGCAGCAGC AGCTCCTGCA CCGCAGCGTT GTGTCATTTA 1010       1020       1030        1040       1050
    TTACGTTGGC AGCTCTGAGG CCTCGGCGCA GCCAACGCGC CTCAGGTATC 1060       1070       1080
    TTTCAGACTC TTTTCTCTAA GGTCTTCCAG ACGGAATTC
```

FIG. 14B

```
                                          10                                              20
Met Ala Asp Leu Phe Ser Gly Leu Val Gly Gly Val Val Gly Ala Val Ala Ala Ala Asp
                                          30                                              40
Leu Pro Ala Glu Gly Glu Arg Ala Pro Arg Pro Ala Pro Gly Thr Ala Trp Thr Cys Cys
                                          50                                              60
Cys Ser Lys Leu Gln Glu Gly Ala Arg Glu Leu Glu Gly Phe Val Gln Gln Leu Ser Phe
                                          70                                              80
Val Ala Gly Lys Leu Ala Cys Cys Leu Arg Val Gly Ala Glu Gln Leu Ala Arg Cys Ala
                                          90                                             100
Ala Glu Gly Arg Leu Pro Ser Ser Ser Ser Ser Ser Cys Cys Ala Leu Leu Gln Leu
                                         110                                             120
Glu Lys Gln Asp Leu Glu Gln Ser Leu Glu Ala Gly Lys Gln Gly Ala Glu Cys Leu Leu
                                         130                                             140
Arg Ser Ser Lys Leu Ala Leu Glu Ala Leu Leu Glu Gly Ala Arg Val Ala Ala Thr Arg
                                         150                                             160
Gly Leu Leu Leu Val Glu Ser Ser Lys Asp Thr Val Leu Arg Ser Ile Pro His Thr Gln
                                         170                                             180
Glu Lys Leu Ala Gln Ala Tyr Ser Ser Phe Leu Arg Gly Try Gln Gly Ala Ala Ala Gly
                                         190                                             200
Arg Ser Leu Gly Tyr Gly Ala Pro Ala Ala Ala Tyr Gly Gln Gln Gln Gln Pro Ser Ser
                                         210                         216
Tyr Gly Ala Pro Pro Ala Ser Ser Gln Gln Pro Ser Gly Phe Phe Trp
```

*FIG. 15*

```
   1 GAATTCATGT TTAGGCGGAT TTTGTTCCAT GCAAGAAAGC CCACCACCGG CTGCAGGTGG
  61 ACTGTACGGG GGACAGACTT TGGAACAACA AGGCATTGCT GTGAGGGAAA CTGCTTCGTG
 121 CAGCGAGAAC CCGTGCCCTA TCGACGCAAC GTGCGGAGAA TGGACAGAGT ACAGTGCGTG
 181 CTCCAGAACT TGCGGAGGCG GTACCCAAGA GAGGAAGAGG GAGCCGTGGT TGGATAATGC
 241 GCAACACGGG GGGCGCACCT GCATGGAACA GTATCCTGAT GGGCCCATAT CGGTCAGGGA
 301 GTGCAACACC CAGCCGTGCC CTGTGGACGA AGTAGTTGGT GATTGGGAAG ACTGGGGGCA
 361 ATGCAGCGAA CAGTGTGGTG GCGGCAAGCG GACTCGTAAT CGCGGCCCAA GCAAGCAAGA
 421 GGCCATGTTC GGAGGCAAGA CAGTTGCTCA ACAGAACGCA GAGCTCCCTG AAGGCGAGAA
 481 GATTGAGGTG GTTCAGGAAG AAGGATGCAA TGAAGTTCCA TGCGGACCTT GCACGCTCCC
 541 CTTCAGTGAG TGGACCGAAT GCGAGTCGTG CTCCGGGCAT AGAACCAGGG AATCCGCAGT
 601 AGCATTTGAT TACACTGACA GAATGTGCAG TGGTGACACA CACGAGGTAC AAAGCTGTGA
 721 GACTGGAGGC TCTGGAGAGG AGGAAGGAAA GGAGGAATCG AGTGGATTTC CAACTGCAGC
 781 TGTAGCCGGT GGCGTGGCTG GGGGAGTCCT CGCGATTGCT GCGGGAGCTG GAGCGTTTTA
 841 TGGATTGAGT GGTGGGAGCG CGGCTGCTGC CACTGAAGCA GGTGCTGAAG TGATGACAGA
 901 AGCTGGTACA TCCAATGCTG CTGAGGTAGA AAAGGAGAGC CTCATCAGTG CAGGTGAACA
 961 ATCAGAGATG TGGGCATCCT AAATGGAAAC GTCGCCGCCG CGGGTTTCGA AAAGGTGCGG
1021 ATCTTGCATA TCTGTGAACG AATTATTTAC TAACATCGAG CTCCTTGACC TCCCGTTGGC
1081 AAATCATTTA CCAAGCATCT CTGGCGCATA GCTTCTTGAA CAAGACAACG AATGTCCAA
1141 CTGGGGAACA GCTATATTGC GAAGTGTGGT GTTCAAACCA GAAGAGAGCA CAGCGTCATG
1201 TGTATGTTAG GGTTGGGCGC CTCCTTTCCC TTATTTATCC CATTTCCTCC GCCTTCATCT
1261 TTCCGCCTTC TCTCTGTGCG CCGTATTTTG GGTGTTATTG GTGCCTGGCG GACAGTAAAG
1321 AGAGATTGGC GTTATTTGCA GCGTGCGCAG GCCATGGTAG GGTTGGATAA CACTCATTGG
1381 TGAAGCGCAA GCCAACAGGG CCACCTTTAC CTCCTGGTGG TCAATGGGGC AGCTTGCTTC
1441 TGATCATTGG TTGGTTCTGT TTCAAGGGGC CGGTAATGGG CAGCAGAAGC TTCTGCCAGC
1501 CACCACACAA TCGAAGCAAC AAATAAGGGA GGTTCTGCTA ACAATTGTGC GTAGTCATGA
1561 TTGTAGGTAG GCTCCGTTTC GAAGATGAAT GACCGGGAGC AGCCTGAATG AAACTTGACT
1621 CTCAAAGAAG GGAATTC
```

```
         10         20         30         40         50         60         70
     SCLGGFCSMQ ESPPPAAGGL YGGQTLEQQG IAVRETASCS ENPCPIDATC GEWTEYSACS RTCGGGTQER
⑥   MNKNS?LGGF??MQ                           ④ ETAS?S ENP?PIDA?? G
③
         80         90        100        110        120        130        140
     KREPWLDNAQ HGGRTCMEQY PDGPISVREC NTQPCPVDEV VGDWEDWGQC SEQCGGGKRT RNRGPSKQEA
     KREPWLDNAQ                                                       NRGPSKQEA 150        160        170        180        190        200        210
     MFGGKTVAQQ NAELPEGEKI EVVQEEGCNE VPCGPCTLPF SEWTECESCS GHRTRESAVA FDYTDRMCSG
①   MFGGKTVAQQ NAELP      ⑦                                ② ESAVA FDYTDR 220        230        240        250        260        270        280
     DTHEVQSCEE YCSQNAGGGA GGDGGAGGGT GGSGEEEGKE ESSGFPTAAV AGGVAGGVLA IAAGAGAFYG 290        300        310        320
     LSGGSAAAAT EAGAEVMTEA GTSNAAEVEK ESLISAGEQS EMWAS
```

```
       10         20         30         40         50
GAATTCCCGA CTTCGAGGGA GGCCCCGGGG GCCTCCCCGC CTGCGAAGCG 60         70         80         90        100
GCGGCGGACG TCGCTGGGGG CCCCTGCAGC AGGGGAGGGC CCCCTGCGGC 110        120        130        140        150
GGTGGGAGCA GCCTGCTGCT GGGACTGCAG CAGCAATCCG GCAGCAGGCT 160        170        180        190        200
GGAGGAGCGG GAGCAGCAGC GGCAGCGCGA GCGGCAGCTG CAGCACGTGC 210        220        230        240        250
GCGCACCCCC GGGCGCGCAG CAGCAGTGCA GGCGCGGCTA AACGCGTGGG 260        270        280        290        300
TGGCGGAGGG CAACAAACTG CCAGAGTCCG AGAGAAGAAG AAGGATGTTA 310        320        330        340        350
GAACAATATA TGAACTTGGA CCAAATACAT AAGTTGAGGA AAAAACTCGA 360        370        380        390        400
CGAAGAAGCA GAAGCCAGGG CCAAATACAT CGAAGGCGGA GTTCAAAAAG 410        420        430        440        450
AACCCCCACT GGGGGCCCCT CAAGGCCGAA AACCCTTTGC TGCCTTTTGC 460        470        480        490        500
CCAGAGAGAG GCCGACGAGG CCTACAGGCG GTTCGGCAGG GGCGCTCCCT 510        520        530        540        550
CTGCGGGGCC CCTCAGGGAG AAGATGCTGC AGGCCCGCAG GAAGTAAAGC 560        570        580        590        600
AGCAGCAGCA GCAGCAGCAG CAGCGGCAGC GGCAGCGGCA GGGGAGGCGG 610        620        630        640        650
AGGAGGCAGG GAGGCTTTTG TTTCGAATTG TTTAGGGAGA GGGCGGAGGG 660        670        680        690        700
CTCGCGGGGT GTATGTACAG CGCGCGAACG CGGCGGCTCA TGTTTGGGTG 710        720        730        740        750
TTGGATTTCG TCTGCAGAAA ACACGAAGCA AATTAAACTG GCAGAAGTTC 760        770        780        790        800
CATTTTTCCA CTTTAAAATG CCACTTTTGC TCTTTATATT GATTAAAACT 810        820        830        840        850
AATGCCATGC TGCTGGCATT CATATAAATG CATTTCCGCG CATTTATGTG 860        870        880        890        900
CATGCATGGC TGGGCGCGGG TGTCTGTACA CCCCAAGAGC CTTGCTGCTC
```

*FIG. 18A*

```
      910        920        930        940        950
CGCCGGCGCG AATTTATATT TATATTTCAT TTATGTAAAT ATAAAAGCCT 960        970        980        990       1000
TCAAAAACAC AAATGGACAT TAATTTATCA AGAAAAAAGA TTAAGGAATT C
```

FIG. 18B

```
                                      10                                          20
Glu Phe Pro Thr Ser Arg Glu Ala Pro Gly Ala Ser Pro Pro Ala Lys Arg Arg Arg Thr
                                      30                                          40
Ser Leu Gly Ala Pro Ala Ala Gly Glu Gly Pro Leu Arg Arg Trp Glu Gln Pro Ala Ala
                                      50                                          60
Gly Thr Ala Ala Ala Ile Arg Gln Gln Ala Gly Gly Ala Gly Ala Ala Ala Ala Ala Arg
                                      70                                          80
Ala Ala Ala Ala Ala Arg Ala Arg Thr Pro Gly Arg Ala Ala Ala Val Gln Ala Arg Leu
                                      90                                         100
Asn Ala Trp Val Ala Glu Gly Asn Lys Leu Pro Glu Ser Glu Arg Arg Arg Arg Met Leu
                                     110                                         120
Glu Gln Tyr Met Asn Leu Glu Lys Val Lys Lys Leu Arg Lys Lys Leu Asp Glu Glu Ala
                                     130                                         140
Glu Ala Arg Ala Lys Tyr Ile Glu Gly Gly Val Gln Lys Glu Pro Pro Teu Gly Ala Pro
                                     150                                         160
Gln Gly Arg Lys Pro Phe Ala Ala Phe Cys Pro Glu Arg Gly Arg Arg Gly Leu Gln Ala
                                     170                                         180
Val Arg Gln Gly Arg Ser Leu Cys Gly Ala Pro Gln Gly Glu Asp Ala Ala Gly Pro Gln
                                     190                                         200
Glu Val Lys Gln Gln Gln Gln Gln Gln Gln Arg Gln Arg Gln Arg Gln Gly Arg Arg
                                     210                                         220
Arg Arg Gln Gly Gly Phe Cys Phe Glu Leu Phe Arg Glu Arg Ala Glu Gly Ser Arg Gly
                                     230                                         240
Val Cys Thr Ala Arg Glu Arg Gly Gly Ser Cys Leu Gly Val Gly Phe Arg Leu Gln Lys
                                     250                                         260
Thr Arg Ser Lys Leu Asn Trp Gln Lys Phe His Phe Ser Thr Leu Lys Cys His Phe Cys

Ser Leu Tyr
```

*FIG. 19*

```
         10         20         30         40         50
GAATTCCGCC CCAGACAGCT AAGCGTGGCA ACATTCTTGG TCTTGTGGGC 60         70         80         90        100
ATGGTAGCCG CTGTCGTCGT GACCTTCACG GAGGCAGGGT TTGGACAGCA 110        120        130        140        150
TTACTTGCTG TTTTTCGCCA CTGCTGCACC GGCCCTTGGC CTGGGGCTGT 160        170        180        190        200
ACATTGCGCA GTCTGTCAAC ATGACTGAGA TGCCTCAACT CGTGGCTCTT 210        220        230        240        250
TTCCACAGTT TCGTCGGTCT TGCCGCCGTA ATGGTTGGGT TCGCGAACTT 260        270        280        290        300
CCACTCCCCT GCTGGCGTGG AGCGCGCTTC CTCACTTCTA CGTCTGTTGG 310        320        330        340        350
AGGTCTACGC CGGCGTTTTC GTCGCCGGTA TCACCTTCAC CGGATCAGTG 360        370        380        390        400
GTCGCTGCGG CAAAGCTCCA TGGATCGATG GAGAGCCGCT CATTGAGGGT 410        420        430        440        450
TCCCGGACGC CATGCGTTGA ATACTGCCAC TATTGCTGCC ATTGGCGTAC 460        470        480        490        500
TTGGCGCTCT TTTTTGCGTC TCTTCTGGCC ACTTTACACG CATGCTTTGC 510        520        530        540        550
CTTTATGTGA ATGCTGGCTT GAGCATGTGG CTTGGTTTTC ACCTGGTCGC 560        570        580        590        600
CGCTATTGGT GGAGCTGACA TGCCCGTCGT GATCAGCTTG CTGAACTCGT 610        620        630        640        650
CGCTATTGGT GGAGCTGACA GCCAGTGGCT TCATGTTGGA CAACAACTTG 660        670        680        690        700
CTGATCATTG CTGGTGCTCT CATCGCGTCA TCTGGTGCCA TTCTGTCTTA 710        720        730        740        750
CATCATGTGC AAAGGCATGA ACCGGAGTCT GTGGAATGTC GTTCTTGGTG 760        770        780        790        800
GCTTCGAGGA GGCCGAGGAC GTTGGCGCAG CCAGCCCTCA GGGGGCTGTG 810        820        830        840        850
CAGCAGGCCA CGGCTGATCA GGTCGCCGAC GAGTTGCTGG CTGCCCGCAA 860        870        880        890        900
AGTTTTGATC GTGCCTGGAT ACGGAATGGC CGTTGCAAGG TGCCAGAGCG
```

*FIG. 20A*

```
       910        920        930        940        950
AGCTTGCAGA CATTGCCAAG AACTTGATGA ACTGCGGTAT CACCGTCGAT 960        970        980        990       1000
TTCGGCATCC ATCCAGTTGC TGGTCGCATG CCAGGCCACA TGAACGTCCT 1010       1020       1030       1040       1050
CCTCGCTGAG GCTGATGTTC CGTACAAGAT TGTCAAGGAG ATGTCTGAAG 1060       1070       1080       1090       1100
TCAACCCGGA AATGAGCTTC TACGACGTCG TCCTGGTTGT TGGAGCCAAC 1110       1120       1130       1140       1150
GACACCGTCA ATCCTGCAGC CCTTGAGCCA GGATCAAAGA TCTCAGGAAT 1160       1170       1180       1190       1200
GCCCGTTATA GAGGCCTGGA AAGCTAGACG CGTTTTGTG CTGAAGCGGT 1210       1220       1230       1240       1250
CCATGGCTGC TGGATATGCC AGCATTGAAA ATCCACTTTT CCATCTGGAG 1260       1270       1280       1290       1300
AACACACGCA TGCTCTTCGG AAACGCAAAG AACACCACTT CTGCAGTCTT 1310       1320       1330       1340       1350
CGCCCGTGTC AATGCCAGAG CCGAGCAAAT GCCACCATCT GCTGCCCGTG 1360       1370       1380       1390       1400
ATGACCTCGA AGCTGGACTA CTTGAGTTCG ATAGGGAAGA ACGTGTTGAT 1410       1420       1430       1440       1450
CCCTCTTCTT GGCCATATCC CAGGATGGCT GTTGGTGTTC TGAGAGACTC 1460       1470       1480       1490       1500
CAATGGCTCT GTTATGGTGC CAGTAGCTCC GAAGTTTGTG CCCAAGCTGA 1510       1520       1530       1540       1550
GGAAGTTGGC ATTCCGTGTC AATGTCGAGT CTGGTGCTGG CGCCGATGCC 1560       1570       1580       1590       1600
GGCTTTACTG ACGAAGAGTA CAGGAGGGCT GGAGCAGAAG TCCTGTCGGG 1610       1620       1630       1640       1650
CCCCGATGCA GTCATTAACC AGTCTCAAGT CCTGCTCCGC GTTTCAGCGC 1660       1670       1680       1690       1700
CGTCGCCAGA TCTGGTTTCG CGCATTCCTA GGGACAAGGT CCTTATCAGT 1710       1720       1730       1740       1750
TACCTATTCC CCAGCATCAA CCAACAAGCT CTTGACATGC TAGCACGCCA 1760       1770       1780       1790       1800
AGGCGTCACC GCACTTGCTG TGGATGAGGT TCCTCGCGTC ACAAGAGCAC
```

*FIG. 20B*

```
           1810       1820       1830       1840       1850
       AGAAGCTAGA CGTGAAGTCT GCTATGCAAG GTCTCCAGGG ATACCGCGCC 1860       1870       1880       1890       1900
       GTTATCGAAG CGTTCAACGC TCTTCCGAAG CTCAGCAAAG CATCTATCAG 1910       1920       1930       1940       1950
       TGCTGCAGGC CGTGTAGAAG CCGCTAAAGT TTTCGTCATC GGTGCCGGTG 1960       1970       1980       1990       2000
       TTGCTGGACT ACAGGCAATT TCTACCGCCC ATGGTTTGGG TGCACAAGTA 2010       2020       2030       2040       2050
       8TTGGCCACG ATGTGCGCTC TGCAACTCGT GAGGAAGTCG AATCTTGCGG 2060       2070       2080       2090       2100
       TGGAAAGTTC ATTGGTTTGA GAATGGGAGA GGAGGGTGAA GTCCTCGGAG 2110       2120       2130       2140       2150
       GATATGCACG CGAGATGGGT GATGCATATC AGAGAGCGCA ACGCGAGATG 2160       2170       2180       2190       2200
       ATTGCCAACA CAATCAAGCA CTGCGATGTC GTCATCTGTA CCGCTGCTAT 2210       2220       2230       2240       2250
       TCACGGCAGA CCTTCACCAA AGCTCATATC ACGCGACATG TTGCGTTCAA 2260       2270       2280       2290       2300
       TGAAGCCTGG CTCCGTCGTC GTAGATCTTG CAACAGAGTT CGGTGATGTG 2310       2320       2330       2340       2350
       CGCTCCGGCT GGGGTGGAAA CGTCGAGGTT TCGCCTAAGG ACGACCAGAT 2360       2370       2380       2390       2400
       TGTCGTTGAT GGCGTCACTG TCATTGGTCG CAGACGCATT GAGACTCGCA 2410       2420       2430       2440       2450
       TGCCCATTCA GGCGTCTGAG CTGTTCTCCA TGAACATATG CAACCTCCTT 2460       2470       2480       2490       2500
       GAGGATCTTG GTGGTGGCAG CAACTTCCGC ATCAACATGG ACGACGAAGT 2510       2520       2530       2540       2550
       CATCAGAGGA TTGGTCGCAG TCTACCAAGG TCGCAACGTG TGGCAGCCAT 2560       2570       2580       2590       2600
       CGCAGCCCAC TCCTGTTTCC AGGACACCTC CGCGCGGCCA GATGCCGCCC 2610       2620       2630       2640       2650
       CCGTCTGCAC CTGGTGCACC AGCTCCTGAG AAGCCTGGTG CCTTTGCTCA 2660       2670       2680       2690       2700
       AGCACTTGCT TCGGATGCAT TCTTCGCAAT GTGTCTTGTT GTTGCTGCCG
```

*FIG. 20C*

```
      2710       2720       2730       2740       2750
CTGTTGTCGG GCTCCTTGGC ATTGTCCTTG ACCCTGTGGA GCTCAAGCAT 2760       2770       2780       2790       2800
TTGACTCTCC TCGGCTTGTC TCTCATCGTC GGCTACTACT GCGTGTGGGC 2810       2820       2830       2840       2850
CGTTACGCCT TCGCTTCACA CACCATTGAT GTCTGTGACG AATGCCCTTT 2860       2870       2880       2890       2900
CGGGAGTCAT TGTCATCGGC TGCATGCTCG AGTACGGAAC CGCCATGATA 2910       2920       2930       2940       2950
TCCGGATTCA CTCTTCTCGC ACTCATTGGA ACCTTCTTGG CTTCCGTCAA.

2960       2970       2980       2990       3000
CGTTGCTGGT GGATTCTTCG TAACTCACCG CATGCTGAAG ATGTTTCAGA 3010       3020       3030       3040       3050
TATAAGGGGA GAACCCCCTT GAGTTAATCT TAACTCAGAA TAACTCTTTT 3060       3070       3080       3090
TCAATTGTAT AAACCTGTAC TCGTTGCAAA AAAAAAAGGA ATTC
```

FIG. 20D

```
                                        10                                      20
     Pro Gln Thr Ala Lys Arg Gly Asn Ile Leu Gly Leu Val Gly Met Val Ala Ala Val Val 30                                      40
     Val Thr Phe Thr Glu Ala Gly Phe Gly Gln His Tyr Leu Leu Phe Phe Ala Thr Ala Ala 50                                      60
     Pro Ala Leu Gly Leu Gly Leu Tyr Ile Ala Gln Ser Val Asn Met Thr Glu Met Pro Gln 70                                      80
     Leu Val Ala Leu Phe His Ser Phe Val Gly Leu Ala Ala Val Met Val Gly Phe Ala Asn 90                                     100
     Phe His Ser Pro Ala Gly Val Glu Arg Ala Ser Ser Leu Leu Arg Leu Leu Glu Val Tyr 110                                     120
     Ala Gly Val Phe Val Ala Gly Ile Thr Phe Thr Gly Ser Val Val Ala Ala Ala Lys Leu 130                                     140
     His Gly Ser Met Glu Ser Arg Ser Leu Arg Val Pro Gly Arg His Ala Leu Asn Thr Ala 150                                     160
     Thr Ile Ala Ala Ile Gly Val Leu Gly Ala Leu Phe Cys Val Ser Ser Gly His Phe Thr 170                                     180
     Arg Met Leu Cys Leu Tyr Val Asn Ala Gly Leu Ser Met Trp Leu Gly Phe His Leu Val 190                                     200
     Ala Ala Ile Gly Gly Ala Asp Met Pro Val Val Ile Ser Leu Leu Asn Ser Tyr Ser Gly 210                                     220
     Val Ala Leu Ala Ala Ser Gly Phe Met Leu Asp Asn Asn Leu Leu Ile Ile Ala Gly Ala 230                                     240
     Leu Ile Ala Ser Ser Gly Ala Ile Leu Ser Tyr Ile Met Cys Lys Gly Met Asn Arg Ser 250                                     260
     Leu Trp Asn Val Val Leu Gly Gly Phe Glu Glu Ala Glu Asp Val Gly Ala Ala Ser Pro 270                                     280
     Gln Gly Ala Val Gln Gln Ala Thr Ala Asp Gln Val Ala Asp Glu Leu Leu Ala Ala Arg 290                                     300
     Lys Val Leu Ile Val Pro Gly Tyr Gly Met Ala Val Ala Arg Cys Gln Ser Glu Leu Ala 310                                     320
     Asp Ile Ala Lys Asn Leu Met Asn Cys Gly Ile Thr Val Asp Phe Gly Ile His Pro Val 330                                     340
     Ala Gly Arg Met Pro Gly His Met Asn Val Leu Leu Ala Glu Ala Asp Val Pro Tyr Lys
```

*FIG. 21A*

```
                                          350                                          360
      Ile Val Lys Glu Met Ser Glu Val Asn Pro Glu Met Ser Ser Tyr Asp Val Val Leu Val
                                          370                                          380
      Val Gly Ala Asn Asp Thr Val Asn Pro Ala Ala Leu Glu Pro Gly Ser Lys Ile Ser Gly
                                          390                                          400
      Met Pro Val Ile Glu Ala Trp Lys Ala Arg Arg Val Phe Val Leu Lys Arg Ser Met Ala
                                          410                                          420
      Ala Gly Tyr Ala Ser Ile Glu Asn Pro Leu Phe His Leu Glu Asn Thr Arg Met Leu Phe
                                          430                                          440
      Gly Asn Ala Lys Asn Thr Thr Ser Ala Val Phe Ala Arg Val Asn Ala Arg Ala Glu Gln
                                          450                                          460
      Met Pro Pro Ser Ala Ala Arg Asp Asp Leu Glu Ala Gly Leu Leu Glu Phe Asp Arg Glu
                                          470                                          480
      Glu Arg Val Asp Pro Ser Ser Trp Pro Tyr Pro Arg Met Ala Val Gly Val Leu Arg Asp
                                          490                                          500
      Ser Asn Gly Ser Val Met Val Pro Val Ala Pro Lys Phe Val Pro Lys Leu Arg Lys Leu
                                          510                                          520
      Ala Phe Arg Val Asn Val Glu Ser Gly Ala Gly Ala Asp Ala Gly Phe Thr Asp Glu Glu
                                          530                                          540
      Tyr Arg Arg Ala Gly Ala Glu Val Leu Ser Gly Pro Asp Ala Val Ile Asn Gln Ser Gln
                                          550                                          560
      Val Leu Leu Arg Val Ser Ala Pro Ser Pro Asp Leu Val Ser Arg Ile Pro Arg Asp Lys
                                          570                                          580
      Val Leu Ile Ser Tyr Leu Phe Pro Ser Ile Asn Gln Gln Ala Leu Asp Met Leu Ala Arg
                                          590                                          600
      Gln Gly Val Thr Ala Leu Ala Val Asp Glu Val Pro Arg Val Thr Arg Ala Gln Lys Leu
                                          610                                          620
      Asp Val Lys Ser Ala Met Gln Gly Leu Gln Gly Tyr Arg Ala Val Ile Glu Ala Phe Asn
                                          630                                          640
      Ala Leu Pro Lys Leu Ser Lys Ala Ser Ile Ser Ala Ala Gly Arg Val Glu Ala Ala Lys
                                          650                                          660
      Val Phe Val Ile Gly Ala Gly Val Ala Gly Leu Gln Ala Ile Ser Thr Ala His Gly Leu
                                          670                                          680
      Gly Ala Gln Val ??? Gly His Asp Val Arg Ser Ala Thr Arg Glu Glu Val Glu Ser Cys
                                          690                                          700
      Gly Gly Lys Phe Ile Gly Leu Arg Met Gly Glu Glu Gly Glu Val Leu Gly Gly Tyr Ala
```

*FIG. 21B*

```
                                    710                                          720
Arg Glu Met Gly Asp Ala Tyr Gln Arg Ala Gln Arg Glu Met Ile Ala Asn Thr Ile Lys 730                                          740
His Cys Asp Val Val Ile Cys Thr Ala Ala Ile His Gly Arg Pro Ser Pro Lys Leu Ile 750                                          760
Ser Arg Asp Met Leu Arg Ser Met Lys Pro Gly Ser Val Val Val Asp Leu Ala Thr Glu 770                                          780
Phe Gly Asp Val Arg Ser Gly Trp Gly Gly Asn Val Glu Val Ser Pro Lys Asp Asp Gln 790                                          800
Ile Val Val Asp Gly Val Thr Val Ile Gly Arg Arg Arg Ile Glu Thr Arg Met Pro Ile 810                                          820
Gln Ala Ser Glu Leu Phe Ser Met Asn Ile Cys Asn Lue Leu Glu Asp Leu Gly Gly Gly 830                                          840
Ser Asn Phe Arg Ile Asn Met Asp Asp Glu Val Ile Arg Gly Leu Val Ala Val Tyr Gln 850                                          860
Gly Arg Asn Val Trp Gln Pro Ser Gln Pro Thr Pro Val Ser Arg Thr Pro Pro Arg Gly 870                                          880
Gln Met Pro Pro Pro Ser Ala Pro Gly Ala Pro Ala Pro Glu Lys Pro Gly Ala Phe Ala 890                                          900
Gln Ala Leu Ala Ser Asp Ala Phe Phe Ala Met Cys Leu Val Val Ala Ala Ala Val Val 910                                          920
Gly Leu Leu Gly Ile Val Leu Asp Pro Val Glu Leu Lys His Leu Thr Leu Leu Gly Leu 930                                          940
Ser Leu Ile Val Gly Tyr Tyr Cys Val Trp Ala Val Thr Pro Ser Leu His Thr Pro Leu 950                                          960
Met Ser Val Thr Asn Ala Leu Ser Gly Val Ile Val Ile Gly Cys Met Leu Glu Tyr Gly 970                                          980
Thr Ala Met Ile Ser Gly Phe Thr Leu Leu Ala Leu Ile Gly Thr Phe Leu Ala Ser Val 990                                          998
Asn Val Ala Gly Gly Phe Phe Val Thr His Arg Met Leu Lys Met Phe Gln Ile
```

*FIG. 21C*

```
                    5                      10                     15
Met Arg Trp Glu Phe Pro Thr Ser Arg Glu Ala Pro Gly Ala Ser ....
```

*FIG. 25A*

```
                    5                      10                     15
Met Lys Ile Ile Phe Phe Leu Cys Ser Phe Leu Phe Phe Ile Ile
Asn Thr Gln Cys:Val Thr His Glu Ser Tyr Glu Glu Leu Val Lys
Lys Leu Glu Ala Ser Ser Arg Gly Thr Ala Cys Asp Ile Glu Leu
Ser Arg Glu Phe Pro Thr Ser Arg Glu Ala Pro Gly Ala Ser ....
```

*FIG. 25B*

```
ATGGCAGACC TCTTCAGCGG ACTCGTGGGC GGCGTCGTCG GCGCTGTTGC
TGCAGCAGAT TTGCCTGCGG AGGGCGAGAG GGCCCCCCGC CCCGCCCCCG
GCACTGCCTG GACTTGCTGC TGCAGCAAAC TGCAAGAAGG GGCCCGCGAG
CTGGAGGGTT TTGTGCAGCA GCTGAGTTTT GTTGCAGGGA AGCTGGCCTG
CTGCCTGCGG GTGGGGGCGG AGCAGCTGGC GCGCTGCGCT GCGGAGGGGC
GGCTGCCCAG CAGCAGCAGC AGCAGCAGCT GCTGCGCGCT GCTGCAGCTC
GAGAAGCAGG ACCTCGAGCA GAGCCTCGAG GCCGGCAAGC AGGGCGCGGA
GTGCCTCTTG AGGAGCAGCA AACTGGCCCT CGAGGCCCTC CTCGAGGGGG
CCCGCGTTGC AGCAACGCGG GGTTTGCTGC TGGTCGAGAG CAGCAAAGAC
ACGGTGCTGC GCAGCATTCC CCACACCCAG GAGAAGCTGG CTCAGGCCTA
CAGTTCTTTC CTGCGGGGCT ACCAGGGGGC AGCAGCGGGG AGGTCTCTGG
GCTACGGGGC CCCTGCTGCT GCTTACGGCC AGCAGCAGCA GCCCAGCAGC
TACGGGGCGC CCCCGCCTC CAGCCAGCAG CCCTCCGGCT TCTTCTGGTA
G
```

FIG. 26

```
CTGTACGGG GGACAGACTT TGGAACAACA AGGCATTGCT GTGAGGGAAA
CTGCTTCGTG CAGCGAGAAC CCGTGCCCTA TCGACGCAAC GTGCGGAGAA
TGGACAGAGT ACAGTGCGTG CTCCAGAACT TGCGGAGGCG GTACCCAAGA
GAGGAAGAGG GAGCCGTGGT TGGATAATGC GCAACACGGG GGGCGCACCT
GCATGGAACA GTATCCTGAT GGGCCCATAT CGGTCAGGGA GTGCAACACC
CAGCCGTGCC CTGTGGACGA AGTAGTTGGT GATTGGGAAG ACTGGGGGCA
ATGCAGCGAA CAGTGTGGTG GCGGCAAGCG GACTCGTAAT CGCGGCCCAA
GCAAGCAAGA GGCCATGTTC GGAGGCAAGA CAGTTGCTCA ACAGAACGCA
GAGCTCCCTG AAGGCGAGAA GATTGAGGTG GTTCAGGAAG AAGGATGCAA
TGAAGTTCCA TGCGGACCTT GCACGCTCCC CTTCAGTGAG TGGACCGAAT
GCGAGTCGTG CTCCGGGCAT AGAACCAGGG AATCCGCAGT AGCATTTGAT
TACACTGACA GAATGTGCAG TGGTGACACA CACGAGGTAC AAAGCTGTGA
GGAATACTGT TCCCAAAATG CTGGAGGGG TGCTGGAGGA GATGGGGGCG
CAGGAGGAGG GACTGGAGGC TCTGGAGAGG AGGAAGGAAA GGAGGAATCG
AGTGGATTTC CAACTGCAGC TGTAGCCGGT GGCGTGGCTG GGGGAGTCCT
CGCCATTGCT GCGGGAGCTG GAGCGTTTTA TGGATTGAGT GGTGGGAGCG
CGGCTGCTGC CACTGAAGCA GGTGCTGAAG TGATGACAGA AGCTGGTACA
TCCAATGCTG CTGAGGTAGA AAAGGAGAGC CTCATCAGTG CAGGTGAACA
ATCAGAGATG TGGGCATCCT AA
```

FIG. 27

LeuTyrGlyGlyGlnThrLeuGluGlnGlnGlyIleAlaValArgGluThrAlaSerCys
SerGluAsnProCysProIleAspAlaThrCysGlyGluTrpThrGluTyrSerAlaCys
SerArgThrCysGlyGlyGlyThrGlnGluArgLysArgGluProTrpLeuAspAsnAla
GlnHisGlyGlyArgThrCysMetGluGlnTyrProAspGlyProIleSerValArgGlu
CysAsnThrGlnProCysProValAspGluValValGlyAspTrpGluAspTrpGlyGln
CysSerGluGlnCysGlyGlyGlyLysArgThrArgAsnArgGlyProSerLysGlnGlu
AlaMetPheGlyGlyLysThrValAlaGlnGlnAsnAlaGluLeuProGluGlyGluLys
IleGluValValGlnGluGluGlyCysAsnGluValProCysGlyProCysThrLeuPro
PheSerGluTrpThrGluCysGluSerCysSerGlyHisArgThrArgGluSerAlaVal
AlaPheAspTyrThrAspArgMetCysSerGlyAspThrHisGluValGlnSerCysGlu
GluTyrCysSerGlnAsnAlaGlyGlyGlyAlaGlyGlyAspGlyGlyAlaGlyGlyGly
ThrGlyGlySerGlyGluGluGluGlyLysGluGluSerSerGlyPheProThrAlaAla
ValAlaGlyGlyValAlaGlyGlyValLeuAlaIleAlaAlaGlyAlaGlyAlaPheTyr
GlyLeuSerGlyGlySerAlaAlaAlaAlaThrGluAlaGlyAlaGluValMetThrGlu
AlaGlyThrSerAsnAlaAlaGluValGluLysGluSerLeuIleSerAlaGlyGluGln
SerGluMetTrpAlaSer

FIG. 28

```
GAATTCCCGA CTTCGAGGGA GGCCCCGGGG GCCTCCCCGC CTGCGAAGCG
GCGGCGGACG TCGCTGGGGG CCCCTGCAGC AGGGGAGGGC CCCCTGCGGC
GGTGGGAGCA GCCTGCTGCT GGGACTGCAG CAGCAATCCG GCAGCAGCTG
GAGGAGCGGG AGCAGCAGCG GCAGCGCGAG CAGCAGCTGC AGCACGTGCA
GCGCACCCCC GGGCGCGCAG CAGCAGTGCA GGCGCGGCTA AACGCGTGGG
TGGCGGAGGG CAACAAACTG CCAGAGTCCG AGAGAAGAAG AAGGATGTTA
GAACAATATA TGAACTTGGA AAAAGTCAAA AAGTTGAGGA AAAAACTCGA
CGAAGAAGCA GAAGCCAGGG CCAAATACAT CGAAGGCGAG TTCAAAAAGA
ACCCCCACTG GGGGCCCCTC AAGGCCGAAA ACCCTTTGCT GCCTTTTGCC
CAGAGAGAGG CCGACGAGGC CTACAGGCGG TTCGGCAGGG GCGCTCCCTC
TGCGGGGCCC CTCAGGGAGA AGATGCTGCA GGCCCGCAGG AAGTAAAGCA
GCAGCAGCAG CAGCAGCAGC AGCGGCAGCG GCAGCGGCAG GGGAGGCGGA
GGAGGCAGGG AGGCTTTTGT TTGAATTGT TTAGGGAGAGG GCGGAGGGCT
CGCGGGGTGT ATGTACAGCG CGCGAACGCG CGGGCTCATG TTTGGGTGTT
GGATTTCGTC TGCAGAAAAC ACGAAGCAAA TTAAACTGGC AGAAGTTCCA
TTTTTCCACT TTAAAATGCC ACTTTTGCTC TTTATATTGA TTAAAACTAA
TGCCATGCTG CTGGCATTCA TATAAATGCA TTTCCGCGCA TTTATGTGCA
TGCATGGCTG GGCGCGGGTG TCTGTACACC CCAAGAGCCT TGCTGCTCCG
CCGGCGCGAA TTTATATTTA TATTTCATTT ATGTAAATAT AAAAGCCTTC
AAAAACACAA ATGGACATTA ATTTATCAAG AAAAAAGATT AAGGAATTC
```

*FIG. 29*

```
              CGA CTTCGAGGGA GGCCCCGGGG GCCTCCCCGC CTGCGAAGCG
       GCGGCGGACG TCGCTGGGGG CCCCTGCAGC AGGGGAGGGC CCCCTGCGGC
       GGTGGGAGCA GCCTGCTGCT GGGACTGCAG CAGCAATCCG GCAGCAGCTG
       GAGGAGCGGG AGCAGCAGCG GCAGCGCGAG CAGCAGCTGC AGCACGTGCA
       GCGCACCCCC GGGCGCGCAG CAGCAGTGCA GGCGCGGCTA AACGCGTGGG
       TGGCGGAGGG CAACAAACTG CCAGAGTCCG AGAGAAGAAG AAGGATGTTA
       GAACAATATA TGAACTTGGA AAAAGTCAAA AAGTTGAGGA AAAAACTCGA
       CGAAGAAGCA GAAGCCAGGG CCAAATACAT CGAAGGCGAG TTCAAAAAGA
       ACCCCCACTG GGGGCCCCTC AAGGCCGAAA ACCCTTTGCT GCCTTTTGCC
       CAGAGAGAGG CCGACGAGGC CTACAGGCGG TTCGGCAGGG GCGCTCCCTC
       TGCGGGGCCC CTCAGGGAGA AGATGCTGCA GGCCCGCAGG AAGTAA
```

FIG. 30

GluPheProThrSerArgGluAlaProGlyAlaSerProProAlaLysArgArgArgThr
SerLeuGlyAlaProAlaAlaGlyGluGlyProLeuArgArgTrpGluGlnProAlaAla
GlyThrAlaAlaAlaIleArgGlnGlnLeuGluGluArgGluGlnGlnArgGlnArgGlu
GlnGlnLeuGlnHisValArgSerThrProGlyArgAlaAlaAlaValGlnAlaArgLeu
AsnAlaTrpValAlaGluGlyAsnLysLeuProGluSerGluArgArgArgArgMetLeu
GluGlnTyrMetAsnLeuGluLysValLysLysLeuArgLysLysLeuAspGluGluAla
GluAlaArgAlaLysTyrIleGluGlyGluPheLysLysAsnProHisTrpGlyProLeu
LysAlaGluAsnProLeuLeuProPheAlaGlnArgGluAlaAspGluAlaTyrArgArg
PheGlyArgGlyAlaProSerAlaGlyProLeuArgGluLysMetLeuGlnAlaArgArg
Lys

*FIG. 31*

ThrSerArgGluAlaProGlyAlaSerProProAlaLysArgArgArgThrSerLeuGly
AlaProAlaAlaGlyGluGlyProLeuArgArgTrpGluGlnProAlaAlaGlyThrAla
AlaAlaIleArgGlnGlnLeuGluGluArgGluGlnGlnArgGlnArgGluGlnGlnLeu
GlnHisValArgSerThrProGlyArgAlaAlaAlaValGlnAlaArgLeuAsnAlaTrp
ValAlaGluGlyAsnLysLeuProGluSerGluArgArgArgArgMetLeuGluGlnTyr
MetAsnLeuGluLysValLysLysLeuArgLysLysLeuAspGluGluAlaGluAlaArg
AlaLysTyrIleGluGlyGluPheLysLysAsnProHisTrpGlyProLeuLysAlaGlu
AsnProLeuLeuProPheAlaGlnArgGluAlaAspGluAlaTyrArgArgPheGlyArg
GlyAlaProSerAlaGlyProLeuArgGluLysMetLeuGlnAlaArgArgLys

*FIG. 32*

```
           CC CCAGACAGCT AAGCGTGGCA ACATTCTTGG TCTTGTGGGC
   ATGGTAGCCG CTGTCGTCGT GACCTTCACG GAGGCAGGGT TTGGACAGCA
   TTACTTGCTG TTTTTCGCCA CTGCTGCACC GGCCCTTGGC CTGGGGCTGT
   ACATTGCGCA GTCTGTCAAC ATGACTGAGA TGCCTCAACT CGTGGCTCTT
   TTCCACAGTT TCGTCGGTCT TGCCGCCGTA ATGGTTGGGT TCGCGAACTT
   CCACTCCCCT GCTGGCGTGG AGCGCGCTTC CTCACTTCTA CGTCTGTTGG
   AGGTCTACGC CGGCGTTTTC GTCGCCGGTA TCACCTTCAC CGGATCAGTG
   GTCGCTGCGG CAAAGCTCCA TGGATCGATG GAGAGCCGCT CATTGAGGGT
   TCCCGGACGC CATGCGTTGA ATACTGCCAC TATTGCTGCC ATTGGCGTAC
   TTGGCGCTCT TTTTTGCGTC TCTTCTGGCC ACTTTACACG CATGCTTTGC
   CTTTATGTGA ATGCTGGCTT GAGCATGTGG CTTGGTTTTC ACCTGGTCGC
   CGCTATTGGT GGAGCTGACA TGCCCGTCGT GATCAGCTTG CTGAACTCGT
   ATTCCGGAGT GGCGTTGGCT GCCAGTGGCT TCATGTTGGA CAACAACTTG
   CTGATCATTG CTGGTGCTCT CATCGCGTCA TCTGGTGCCA TTCTGTCTTA
   CATCATGTGC AAAGGCATGA ACCGGAGTCT GTGGAATGTC GTTCTTGGTG
   GCTTCGAGGA GGCCGAGGAC GTTGGCGCAG CCAGCCCTCA GGGGGCTGTG
   CAGCAGGCCA CGGCTGATCA GGTCGCCGAC GAGTTGCTGG CTGCCCGCAA
   AGTTTTGATC GTGCCTGGAT ACGGAATGGC CGTTGCAAGG TGCCAGAGCG
   AGCTTGCAGA CATTGCCAAG AACTTGATGA ACTGCGGTAT CACCGTCGAT
   TTCGGCATCC ATCCAGTTGC TGGTCGCATG CCAGGCCACA TGAACGTCCT
   CCTCGCTGAG GCTGATGTTC CGTACAAGAT TGTCAAGGAG ATGTCTGAAG
   TCAACCCGGA AATGAGCTCC TACGACGTCG TCCTGGTTGT TGGAGCCAAC
   GACACCGTCA ATCCTGCAGC CCTTGAGCCA GGATCAAAGA TCTCAGGAAT
   GCCCGTTATA GAGGCCTGGA AAGCTAGACG CGTTTTTGTG CTGAAGCGGT
   CCATGGCTGC TGGATATGCC AGCATTGAAA ATCCACTTTT CCATCTGGAG
   AACACACGCA TGCTCTTCGG AAACGCAAAG AACACCACTT CTGCAGTCTT
   CGCCCGTGTC AATGCCAGAG CCGAGCAAAT GCCACCATCT GCTGCCCGTG
   ATGACCTCGA AGCTGGACTA CTTGAGTTCG ATAGGGAAGA ACGTGTTGAT
   CCCTCTTCTT GGCCATATCC CAGGATGGCT GTTGGTGTTC TGAGAGACTC
   CAATGGCTCT GTTATGGTGC CAGTAGCTCC GAAGTTTGTG CCCAAGCTGA
   GGAAGTTGGC ATTCCGTGTC AATGTCGAGT CTGGTGCTGG CGCCGATGCC
   GGCTTTACTG ACGAAGAGTA CAGGAGGGCT GGAGCAGAAG TCCTGTCGGG
   CCCCGATGCA GTCATTAACC AGTCTCAAGT CCTGCTCCGC GTTTCAGCGC
   CGTCGCCAGA TCTGGTTTCG CGCATTCCTA GGGACAAGGT CCTTATCAGT
   TACCTATTCC CCAGCATCAA CCAACAAGCT CTTGACATGC TAGCACGCCA
   AGGCGTCACC GCACTTGCTG TGGATGAGGT TCCTCGCGTC ACAAGAGCAC
   AGAAGCTAGA CGTGAAGTCT GCTATGCAAG GTCTCCAGGG ATACCGCGCC
   GTTATCGAAG CGTTCAACGC TCTTCCGAAG CTCAGCAAAG CATCTATCAG
   TGCTGCAGGC CGTGTAGAAG CCGCTAAAGT TTTCGTCATC GGTGCCGGTG
```

*FIG. 33A*

```
TTGCTGGACT ACAGGCAATT TCTACCGCCC ATGGTTTGGG TGCACAAGTA
TTTGGCCACG ATGTGCGCTC TGCAACTCGT GAGGAAGTCG AATCTTGCGG
TGGAAAGTTC ATTGGTTTGA GAATGGGAGA GGAGGGTGAA GTCCTCGGAG
GATATGCACG CGAGATGGGT GATGCATATC AGAGAGCGCA ACGCGAGATG
ATTGCCAACA CAATCAAGCA CTGCGATGTC GTCATCTGTA CCGCTGCTAT
TCACGGCAGA CCTTCACCAA AGCTCATATC ACGCGACATG TTGCGTTCAA
TGAAGCCTGG CTCCGTCGTC GTAGATCTTG CAACAGAGTT CGGTGATGTG
CGCTCCGGCT GGGGTGGAAA CGTCGAGGTT TCGCCTAAGG ACGACCAGAT
TGTCGTTGAT GGCGTCACTG TCATTGGTCG CAGACGCATT GAGACTCGCA
TGCCCATTCA GGCGTCTGAG CTGTTCTCCA TGAACATATG CAACCTCCTT
GAGGATCTTG GTGGTGGCAG CAACTTCCGC ATCAACATGG ACGACGAAGT
CATCAGAGGA TTGGTCGCAG TCTACCAAGG TCGCAACGTG TGGCAGCCAT
CGCAGCCCAC TCCTGTTTCC AGGACACCTC CGCGCGGCCA GATGCCGCCC
CCGTCTGCAC CTGGTGCACC AGCTCCTGAG AAGCCTGGTG CCTTTGCTCA
AGCACTTGCT TCGGATGCAT TCTTCGCAAT GTGTCTTGTT GTTGCTGCCG
CTGTTGTCGG GCTCCTTGGC ATTGTCCTTG ACCCTGTGGA GCTCAAGCAT
TTGACTCTCC TCGGCTTGTC TCTCATCGTC GGCTACTACT GCGTGTGGGC
CGTTACGCCT TCGCTTCACA CACCATTGAT GTCTGTGACG AATGCCCTTT
CGGGAGTCAT TGTCATCGGC TGCATGCTCG AGTACGGAAC CGCCATGATA
TCCGGATTCA CTCTTCTCGC ACTCATTGGA ACCTTCTTGG CTTCCGTCAA
CGTTGCTGGT GGATTCTTCG TAACTCACCG CATGCTGAAG ATGTTTCAGA
TATAA
```

FIG. 33B

ThrAlaLysArgGlyAsnIleLeuGlyLeuValGlyMetValAlaAlaValVal
ValThrPheThrGluAlaGlyPheGlyGlnHisTyrLeuLeuPhePheAlaThrAlaAla
ProAlaLeuGlyLeuGlyLeuTyrIleAlaGlnSerValAsnMetThrGluMetProGln
LeuValAlaLeuPheHisSerPheValGlyLeuAlaAlaValMetValGlyPheAlaAsn
PheHisSerProAlaGlyValGluArgAlaSerSerLeuLeuArgLeuLeuGluValTyr
AlaGlyValPheValAlaGlyIleThrPheThrGlySerValValAlaAlaAlaLysLeu
HisGlySerMetGluSerArgSerLeuArgValProGlyArgHisAlaLeuAsnThrAla
ThrIleAlaAlaIleGlyValLeuGlyAlaLeuPheCysValSerSerGlyHisPheThr
ArgMetLeuCysLeuTyrValAsnAlaGlyLeuSerMetTrpLeuGlyPheHisLeuVal
AlaAlaIleGlyGlyAlaAspMetProValValIleSerLeuLeuAsnSerTyrSerGly
ValAlaLeuAlaAlaSerGlyPheMetLeuAspAsnAsnLeuLeuIleIleAlaGlyAla
LeuIleAlaSerSerGlyAlaIleLeuSerTyrIleMetCysLysGlyMetAsnArgSer
LeuTrpAsnValValLeuGlyGlyPheGluGluAlaGluAspValGlyAlaAlaSerPro
GlnGlyAlaValGlnGlnAlaThrAlaAspGlnValAlaAspGluLeuLeuAlaAlaArg
LysValLeuIleValProGlyTyrGlyMetAlaValAlaArgCysGlnSerGluLeuAla
AspIleAlaLysAsnLeuMetAsnCysGlyIleThrValAspPheGlyIleHisProVal
AlaGlyArgMetProGlyHisMetAsnValLeuLeuAlaGluAlaAspValProTyrLys
IleValLysGluMetSerGluValAsnProGluMetSerSerTyrAspValValLeuVal
ValGlyAlaAsnAspThrValAsnProAlaAlaLeuGluProGlySerLysIleSerGly
MetProValIleGluAlaTrpLysAlaArgArgValPheValLeuLysArgSerMetAla
AlaGlyTyrAlaSerIleGluAsnProLeuPheHisLeuGluAsnThrArgMetLeuPhe
GlyAsnAlaLysAsnThrThrSerAlaValPheAlaArgValAsnAlaArgAlaGluGln
MetProProSerAlaAlaArgAspAspLeuGluAlaGlyLeuLeuGluPheAspArgGlu
GluArgValAspProSerSerTrpProTyrProArgMetAlaValGlyValLeuArgAsp
SerAsnGlySerValMetValProValAlaProLysPheValProLysLeuArgLysLeu
AlaPheArgValAsnValGluSerGlyAlaGlyAlaAspAlaGlyPheThrAspGluGlu
TyrArgArgAlaGlyAlaGluValLeuSerGlyProAspAlaValIleAsnGlnSerGln
ValLeuLeuArgValSerAlaProSerProAspLeuValSerArgIleProArgAspLys
ValLeuIleSerTyrLeuPheProSerIleAsnGlnGlnAlaLeuAspMetLeuAlaArg
GlnGlyValThrAlaLeuAlaValAspGluValProArgValThrArgAlaGlnLysLeu
AspValLysSerAlaMetGlnGlyLeuGlnGlyTyrArgAlaValIleGluAlaPheAsn
AlaLeuProLysLeuSerLysAlaSerIleSerAlaAlaGlyArgValGluAlaAlaLys
ValPheValIleGlyAlaGlyValAlaGlyLeuGlnAlaIleSerThrAlaHisGlyLeu
GlyAlaGlnValPheGlyHisAspValArgSerAlaThrArgGluGluValGluSerCys
GlyGlyLysPheIleGlyLeuArgMetGlyGluGluGlyGluValLeuGlyGlyTyrAla
ArgGluMetGlyAspAlaTyrGlnArgAlaGlnArgGluMetIleAlaAsnThrIleLys
HisCysAspValValIleCysThrAlaAlaIleHisGlyArgProSerProLysLeuIle
SerArgAspMetLeuArgSerMetLysProGlySerValValValAspLeuAlaThrGlu

*FIG. 34A*

PheGlyAspValArgSerGlyTrpGlyGlyAsnValGluValSerProLysAspAspGln
IleValValAspGlyValThrValIleGlyArgArgArgIleGluThrArgMetProIle
GlnAlaSerGluLeuPheSerMetAsnIleCysAsnLeuLeuGluAspLeuGlyGlyGly
SerAsnPheArgIleAsnMetAspAspGluValIleArgGlyLeuValAlaValTyrGln
GlyArgAsnValTrpGlnProSerGlnProThrProValSerArgThrProProArgGly
GlnMetProProProSerAlaProGlyAlaProAlaProGluLysProGlyAlaPheAla
GlnAlaLeuAlaSerAspAlaPhePheAlaMetCysLeuValValAlaAlaAlaValVal
GlyLeuLeuGlyIleValLeuAspProValGluLeuLysHisLeuThrLeuLeuGlyLeu
SerLeuIleValGlyTyrTyrCysValTrpAlaValThrProSerLeuHisThrProLeu
MetSerValThrAsnAlaLeuSerGlyValIleValIleGlyCysMetLeuGluTyrGly
ThrAlaMetIleSerGlyPheThrLeuLeuAlaLeuIleGlyThrPheLeuAlaSerVal
AsnValAlaGlyGlyPhePheValThrHisArgMetLeuLysMetPheGlnIle

*FIG. 34B*

RECOMBINANT COCCIDIOSIS VACCINES

This application is a continuation-in-part of U.S. Ser. No. 07/202,721, filed Jun. 3, 1988, now abandoned.

TABLE OF CONTENTS
1. Technical Field
2. Background of the Invention
   2.1. Prevention of Coccidiosis
   2.2. Recombinant DNA Technology
   2.3. Subunit Vaccines
3. Summary of the Invention
4. Brief Description of the Figures
5. Description of the Invention
   5.1. Definitions
   5.2. Preparation of Coccidial Proteins
      5.2.1. Recombinant DNA
         5.2.1.1. Identification of Clones
         5.2.1.2. Cell Disruption
      5.2.2. Chemical Synthesis
      5.2.3. Immunoprecipitation and Immunoaffinity Chromatography
      5.2.4. Anti-Idiotype Antibodies
   5.3. Poultry Vaccination
      5.3.1. Use of Eimeria Proteins and Anti-Idiotype Antibodies
      5.3.2. Vector Systems
6. Examples
   6.1. Preparation of Monoclonal Antibodies Against Eimeria Antigens
      6.1.1. Parasite Preparation
      6.1.2. Immunizations
      6.1.3. Cell Culture and Cell Fusions
      6.1.4. Sporozoite ELISA
      6.1.5. Western Blotting of Sporozoite Proteins
      6.1.6. Immunoprecipitation of +hu 125I-Labeled Sporozoite Surface Proteins
      6.1.7. Immunofluorescence Assays With Purified Sporozoites
      6.1.8. Summary of ELISA, Western Blot, Immunoprecipitation and Immunofluorescence Results
      6.1.9. In Vitro Infection Assays
      6.1.10. In Vitro Sporozoite Neutralization Assays
   6.2. Construction of cDNA Expression Libraries
      6.2.1. Preparation of Sporulating Oocysts
      6.2.2. Isolation of Sporulating Oocyst mRNA
      6.2.3. Preparation of Merozoites
      6.2.4. Isolation of Merozoite mRNA
      6.2.5. Synthesis of Oocyst and Merozoite cDNAs, and Insertion into Phage Vectors
   6.3. Immunological Screening of cDNA Libraries
   6.4. Expression of +i Eimeria Genes in +i E. Coli
   6.5. DNA Sequence Analysis
   6.6. Purification and Characterization of the 65 Kd Protein
      6.6.1. Protein Purification
      6.6.2. Isoelectric Point Determination
      6.6.3. Amino Acid Composition Analysis
      6.6.4. N- and C-Terminal Sequence Analysis
      6.6.5. Tryptic Peptide Analysis
   6.7. Poultry Immunization
      6.7.1. Use of the 65 Kd Antigen
      6.7.2. Vaccinia Vector Vaccination
         6.7.2.1. Vector Preparation
         6.7.2.2. Chick Immunization

1. TECHNICAL FIELD

This application relates to the use of recombinant DNA technology to produce antigens of Eimeria protozoan parasites. These recombinantly produced antigens can be used, through various routes of administration, to protect poultry against coccidiosis.

2. BACKGROUND OF THE INVENTION

2.1. Prevention of Coccidiosis

Coccidiosis is a costly disease of poultry caused by intracellular protozoan parasites of the genus Eimeria. The disease is endemic in the large, intensive poultry breeding establishments in this country, and the estimated cost of control of the disease through chemotherapy exceeds $100 million each year. Resistance to the anti-coccidial drugs develops, necessitating a continuing development of new agents, at a time when drug development is becoming increasingly expensive and consumer acceptance of drug residues in food animals is diminishing.

Protective immunity to natural coccidiosis infection has been well documented. Controlled, daily administration of small numbers of viable oocysts for several weeks has been shown to result in complete immunity to a challenge infection of a normally virulent dose [Rose et al., Parasitology 73:25 (1976); Rose et al., Parasitology 88:199 (1984)]. The demonstration of acquired resistance to infection suggests the possibility of constructing a vaccine to induce immunity in young chickens, circumventing the need for chemical coccidiostats. In fact, such a concept has been tested in the Coccivac® formulation of Sterwin Laboratories. Opelika, Ala.

With a view to producing a coccidiosis vaccine, Murray et al., European Patent Publication No. 167,443, prepared extracts from sporozoites or sporulated oocysts of Eimeria tenella which contain at least 15 polypeptides, many of which were associated with the surface of the sporozoite. Injection of these extracts into chickens reduced cecal lesions following oral inoculation with virulent E. tenella sporulated oocysts. More recently, Schenkel et al., U.S. Pat. No. 4,650,676, disclosed the production of monoclonal antibodies against E. tenella merozoites. Using these antibodies, Schenkel et al. identified a number of antigens against which the antibodies were directed. By preincubating E. tenella sporozoites with these antibodies and then introducing the treated sporozoites into the ceca of chickens, Schenkel et al. were able to show some reduction in cecal lesion scores, compared to untreated sporozoite controls.

2.2. Recombinant DNA Technology

Advances in recombinant DNA technology have made another approach available, a subunit vaccine. In the application of current recombinant DNA procedures, specific DNA sequences are inserted into an appropriate DNA vehicle, or vector, to form recombinant DNA molecules that can replicate in host cells. Circular double-stranded DNA molecules called plasmids are frequently used as vectors, and the preparation of such recombinant DNA forms entails the use of restriction endonuclease enzymes that can cleave DNA at specific base sequence sites. Once cuts have been made by a restriction enzyme in a plasmid and in the segment of foreign DNA that is to be inserted, the two DNA molecules may be covalently linked by an enzyme known as a ligase. General methods for the preparation of such recombinant DNA molecules have been described by Cohen et al. [U.S. Pat. No. 4,237,224], Collins et al. [U.S. Pat. No. 4,304,863] and Maniatis et al. [Molecular Cloning: A Laboratory Manual, 1982, Cold Spring Harbor Laboratory].

Because they illustrate much of the state of the art, these references are hereby incorporated by reference.

Once prepared, recombinant DNA molecules can be used to produce the product specified by the inserted gene sequence only if a number of conditions are met. Foremost is the requirement that the recombinant molecule be compatible with, and thus capable of autonomous replication in, the host cell. Much recent work has utilized *Escherichia coli* as a host organism, because it is compatible with a wide range of recombinant plasmids. Depending upon the vector/ host cell system used, the recombinant DNA molecule is introduced into the host by transformation, transduction or transfection.

Detection of the presence of recombinant plasmids in host cells may be conveniently achieved through the use of plasmid marker activities, such as antibiotic resistance. Thus, a host bearing a plasmid coding for the production of an ampicillin-degrading enzyme could be selected from unaltered cells by growing the host in a medium containing ampicillin. Further advantage may be taken of antibiotic resistance markers where a plasmid codes for a second antibiotic-degrading activity at a site where the selected restriction endonuclease makes its cut and the foreign gene sequence is inserted. Host cells containing properly recombinant plasmids will then be characterized by resistance to the first antibiotic but sensitivity to the second.

The mere insertion of a recombinant plasmid into a host cell and the isolation of the modified host will not in itself assure that significant amounts of the desired gene product will be produced. For this to occur, the foreign gene sequence must be fused in proper relationship to a signal region in the plasmid for DNA transcription called a promoter. Alternatively, the foreign DNA may carry its own promoter, as long as it is recognized by the host. Whatever its origin, the promoter is a DNA sequence that directs the binding of RNA polymerase and therefore "promotes" the transcription of DNA to messenger RNA (mRNA).

Given strong promotion that can provide large quantities of mRNA, the ultimate production of the desired gene product will be dependent upon the effectiveness of translation from mRNA to protein. This, in turn, is dependent upon the efficiency of ribosomal binding to the mRNA. In *E. coli*, the ribosome-binding site on mRNA includes an initiation codon (AUG) and an upstream Shine-Dalgarno (SD) sequence. This sequence, containing 3-9 nucleotides and located 3-11 nucleotides from the AUG codon, is complementary to the 3' end of *E. coli* 16S ribosomal RNA (rRNA) [Shine and Dalgarno, Nature 254:34 (1975)]. Apparently, ribosomal binding to, mRNA is facilitated by base pairing between the SD sequence in the mRNA and the sequence at the 16S rRNA 3' end. For a review on maximizing gene expression, see Roberts and Lauer, Methods in Enzymology 68:473 (1979).

An alternative expression system has been developed based on the lacZ operon in combination with lambda phage vectors. (Huynh et al., in *DNA Cloning: Volume I*, DM Glover, Ed.). In this system, the structural gene for β-galactosidase along with the inducible promoter controlling its expression have been engineered into the phage vector. A unique cloning site at the 3' end of the gene for β-galactosidase results in a gene fusion upon the insertion of a cDNA copy of an mRNA or a genomic DNA fragment containing a protein-coding region.

Expression of the β-galactosidase gene results in the production of a fusion protein containing 114 kd of β-galactosidase and a carboxy terminal polypeptide encoded by the cDNA insert, provided that the insert contains an open reading frame in the same register as the reading frame for β-galactosidase. A phage containing a gene whose product is recognized by a monoclonal or a polyclonal antiserum can thus be identified by immunologic screening of the library following induction of expression of the fusion protein using β-D-thiogalactopyranoside (IPTG) to inactivate the lacZ repressor. This expression vector system combines the efficiency of the phage system in packaging DNA and introducing it into *E. coli* cells with an increased stability of polypeptide fusions with β-galactosidase.

2.3. Subunit Vaccines

In the vaccine subunit approach, a subunit of the whole infectious organism is delivered to the host animal in an immunologically relevant context. The subunit might be a protein purified from the parasite, a recombinant protein or protein fragment expressed in a heterologous system, a synthetic peptide comprising a single neutralizing determinant or a protein introduced by a viral vector such as vaccinia. The host immune system mounts a specific response to the subunit without ever being exposed to the whole parasite. Upon challenge with a virulent dose of the infectious organism, the host immune system mounts a successful defense, instructed only by the vaccine subunit to which it had been previously exposed.

Evidence can be found in the literature for the involvement of circulating antibodies, secretory IgA in the intestinal epithelium [Davis et al., Immunology 34:879 (1978)], and the cell-mediated immune system [Giambroni et al., Poultry Science 59:38 (1980)] in acquired resistance to coccidiosis. For a review, see P. S. Davis in Avian Immunology, M. E. Rose, Ed., British Poultry Science, Ltd., Edenberg, pp. 361–385 (1981). The probable involvement of various arms of the immune system means that complete and lasting protection may necessitate the ability to mimic specific aspects of the natural infectious process. These aspects include local exposure at the site where protection is desired, evocation of an inflammatory response to marshall antigen processing cells, presentation of an appropriate parasite antigen and possibly association with MHC determinants in a particular membrane configuration.

3. SUMMARY OF THE INVENTION

This invention provides purified proteins or fragments thereof having one or more immunoreactive and/or antigenic determinants of an Eimeria surface antigen.

More particularly, this invention provides proteins or fragments thereof having one or more immunoreactive and/ or antigenic determinants of an Eimeria surface antigen, which surface antigen has an apparent molecular weight of about 28, 37, 120 or greater than 200 kilodaltons and specifically binds to one or more monoclonal antibodies deposited with the American Type Culture Collection and assigned accession Nos. HB 9707 through HB 9712.

This invention further provides the foregoing deposited monoclonal antibodies.

This invention still further provides DNA sequences or fragments thereof encoding proteins or fragments thereof having one or more immunoreactive and/or antigenic determinants of an Eimeria surface antigen, which surface antigen has an apparent molecular weight of about 28, 37, 120 or greater than 200 kilodaltons and specifically binds to one or more monoclonal antibodies deposited with the American Type Culture Collection and assigned accession Nos. HB 9707 through HB 9712; recombinant vectors containing and capable of directing the expression of such DNA sequences or fragments in compatible host organisms; and microorganisms containing such vectors which are capable of expressing the DNA sequences or fragments.

This invention still further provides a method for producing a protein or fragment thereof having one or more immunoreactive and/or antigenic determinants of an *Eimeria tenella* surface antigen, which method comprises:

(a) culturing a microorganism containing a recombinant vector and a DNA sequence or fragment thereof having one or more immunoreactive and/or antigenic determinants of an Eimeria surface antigen, which surface antigen has an apparent molecular weight of 28, 37, 120 or greater than 200 kilodaltons and specifically binds to one or more monoclonal antibodies deposited with the American Type Culture Collection and assigned accession Nos. HB 9707 through HB 9712, under conditions in which the DNA sequence or fragment is expressed; and (b) isolating the protein or fragment from the culture.

This invention still further provides vaccines for protecting poultry against coccidiosis comprising one or more of the proteins or fragments thereof of the invention and a physiologically acceptable carrier.

This invention still further provides vaccines for protecting poultry against coccidiosis comprising a viral vector containing a DNA sequence or fragment thereof coding for a protein or fragment thereof of the invention, which viral vector is capable of expressing the DNA sequence or fragment, and a physiologically acceptable carrier.

This invention still further provides a method for protecting poultry against coccidiosis, which method comprises administering an effective amount of a vaccine of the invention to a young fowl which is susceptible to coccidiosis.

4. BRIEF DESCRIPTION OF THE FIGURES

The present invention can be more readily understood by reference to the following Description of the Invention and Examples, and to the following Figures in which:

FIG. 1 shows the results of an *E. tenella* sporozoite ELISA. Dilutions of immune mouse serum (Ms 107-2; Δ) and control mouse serum (X) were incubated with $4\times10^4$ live purified sporozoites. Specific antibody bound to the sporozoites was detected with a peroxidase-conjugated anti-mouse IgG antibody and the peroxidase substrate o-phenylenediamine. The $OD_{492}$nm was read in a Titertek Multiscan® plate reader.

FIG. 2 shows the results of a Western blot assay performed with proteins solubilized from *E. tenella* sporozoites. Solubilized sporozoite proteins were separated by reducing SDS-polyacrylamide gel electrophoresis in 12.5% gels, transferred to nitrocellulose membranes and reacted with each antibody. The specific proteins recognized by each antibody were visualized with a peroxidase-conjugated anti-mouse IgG antibody and the peroxidase substrate 4-chloro-1-naphthol. The antibody which was reacted with each strip is noted at the top of the strip.

FIG. 3 shows the results of a Western blot assay performed with proteins solubilized from sporozoites and merozoites of *E. tenella*, and from sporozoites of *E. acervulina*. Various monoclonal antibodies and sera were incubated with nitrocellulose bound Eimeria proteins and visualized as explained in the description of FIG. 2. The monoclonal antibodies used included 3A5 (1), 20C6 (2), 7D1 (3), 13A6 (4), 6A5 (5) and a control antibody that was unreactive to the Eimeria proteins. The sera used included mouse No. 107-2 immune serum (7) and control serum (8).

FIG. 4 shows in the left panel the results of an immunoprecipitation assay with $^{125}$I-labeled surface proteins of *E. tenella* sporozoites. Sporozoite surface proteins were labeled by either the IODOGEN or IODOBEADS method, solubilized and visualized following SDS-polyacrylamide gel electrophoresis in 12.5% gels by autoradiography. The right panel shows the results of immunoprecipitation of $^{125}$I-labeled sporozoite surface proteins by serum from mice immunized with live sporozoites. Immune mouse sera (105-1, 105-2, 105-3, 107-1, 107-2 and 107-3) and control mouse serum (Control) were incubated with $^{125}$I-sporozoite surface proteins, and the immune complexes were captured by an anti-mouse antibody coupled to agarose. The immune complexes were solubilized with Laemmli sample buffer, separated by SDS-gel electrophoresis in 12.5% gels and visualized by autoradiography. M represents the molecular weights of standard marker proteins in kilodaltons.

FIG. 5 shows the results of immunoprecipitation of $^{125}$I-sporozoite surface proteins by monoclonal antibodies. The procedure for identifying the $^{125}$I-proteins bound by each antibody is explained in the description of FIG. 4. Specific sporozoite monoclonal antibodies used and control antibody (control) are indicated at the top of each gel lane. Molecular weights of standard marker proteins are shown in kilodaltons.

FIG. 6 shows phase contrast micrographs and immunofluorescence staining pattern micrographs using various monoclonal antibodies, of air-dried *E. tenella* sporozoite slide preparations. The left sides of panels A, B, C and D are phase contrast micrographs showing intact elongated sporozoites with a large posterior refractile body (PRB), a small anterior refractile body (ARB) and the apical end (A) opposite the posterior refractile body. The right sides of panels A, B, C and D show slides which were treated with monoclonal antibodies 14C3 (specific for surface antigens), 6A5 (specific for surface and refractile body protein), 11D2 (specific for sporozoite apical tip) and control antibody, respectively. The antibodies bound to the preparations were localized with rhodamine-conjugated anti-mouse antibodies, visualized by epifluorescence using a Leitz Dialux 22® microscope. All micrographs are 630×.

FIGS. 7(A–D) shows antibody staining of intracellular sporozoites and the developing parasite in chicken kidney cells. Chicken kidney cells were infected with sporozoites, and at the indicated times after infection the cells were processed for antibody staining. The cultures were washed before fixation to remove any extracellular sporozoites. Phase contrast and corresponding immunofluorescence micrographs were made using antibodies 7D4, 8A2, 7B2 and 15A 3 in FIGS. 7A–7D as indicated. The antibodies bound to the preparations were localized with rhodamine-conjugated anti-mouse antibodies, visualized by epifluorescence. All micrographs are 630×.

FIGS. 8(A–B) shows antibody staining of intracellular sporozoites and the developing parasite in chicken kidney cells. Phase contrast micrographs and corresponding immunofluorescence micrographs were made using monoclonal antibodies 14B1 and 19D6 as indicated, immune chick sera and fluorescent second antibodies, at the indicated times.

FIG. 9 shows the neutralization of intracellular sporozoite development by anti-sporozoite antibodies. Purified *E. tenella* sporozoites Were preincubated for 1 hour at 40° C. with either control antibody (X) or anti-sporozoite antibodies 7D4 (□), 8A2 (○), 14B1 (●) or 6A5 (■) and then allowed to infect MDBK cell cultures. Sporozoites were also preincubated with media (Δ) or with the anti-coccidial drug, lasalocid (*).

After infection, the development of the intracellular sporozoite was measured by the incorporation of $^3$H-uracil into the cell cultures. Since lasalocid prevents intracellular development of the sporozoite, cultures pretreated with this drug showed minimal incorporation of $^3$H-uracil.

FIG. 10 shows the results of SDS-polyacrylamide gel electrophoretic/Western Blot analysis of 65 Kd-β-galactosidase fusion protein samples or other samples as noted. The Western Blot analysis was carried out using murine anti-β-galactosidase antibody (panel A) or pooled monoclonal antibodies 7D1, 7D4 and 20C6 (panel B) in conjunction with goat anti-mouse HPOD conjugate. The lanes in both panels represent (1) β-galactosidase, (m) prestained molecular weight markers, the sizes of which are indicated to the left of plate A in kd, (2) total cell pellet protein, (3) protein released from the cell pellet by sonication and (4) protein solubilized by guanidine-HCl from the pellet after sonication.

Figure 13:
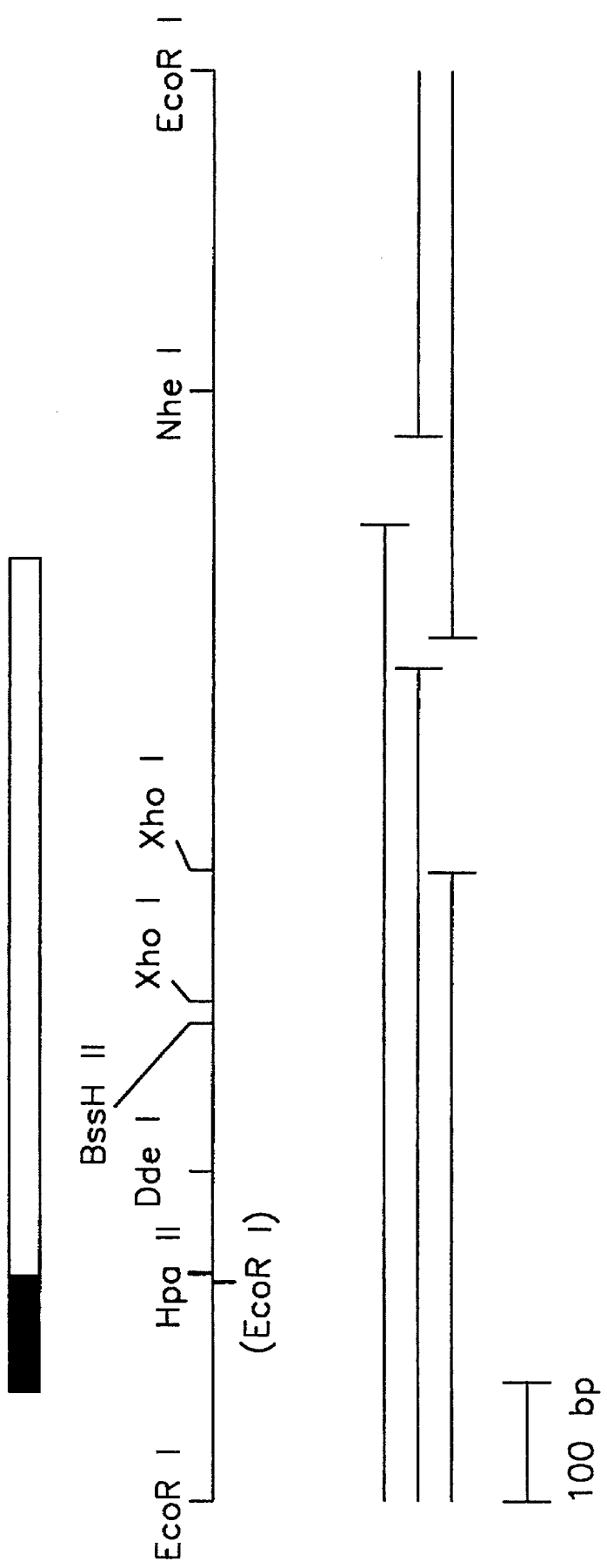

FIG. 13 is a restriction map of cDNA clones encoding proteins recognized by monoclonal antibody 6A5. Restriction endonuclease sites used for Maxam-Gilbert DNA sequence analysis of the 1.1 kb cDNA are shown. The EcoRI site in parentheses is at the end of the 0.9 kb cDNA. The bar above the map shows the open reading frame predicted from the DNA sequence, with the potential signal peptide filled in. The lines below the map indicate the exoIII deletions used for chain-termination sequence analysis.

FIGS. 14(A–B) taken together represent the nucleotide sequence of the 1.1 kb cDNA molecule encoding the 20 kd protein recognized by monoclonal antibody 6A5.

FIG. 15 is the amino acid sequence of the protein of FIG. 14, predicted from the nucleotide sequence of that figure.

FIG. 16 is the nucleotide sequence of the 1.7 kb cDNA molecule encoding the 65 kd protein recognized by monoclonal antibodies 7D1, 7D4 and 20C6.

FIG. 17 is the amino acid sequence of the protein of FIG. 16, predicted from the nucleotide sequence of that figure and confirmed by sequence analysis of tryptic peptides produced from the expressed 65 kd protein. Regions in the overall amino acid sequence corresponding to some of these peptides are shown underlined. The determined sequences of these peptides are overlined.

FIGS. 18(A–B) taken together represent the nucleotide sequence of the 1.1 kb cDNA molecule encoding the 28 kd protein recognized by monoclonal antibody 8A2.

FIG. 19 is the amino acid sequence of the protein of FIG. 18, predicted from the nucleotide sequence of that figure.

FIGS. 20(A–D) taken together represent the nucleotide sequence of the 3.2 kb cDNA molecule encoding the protein recognized by monoclonal antibody 7B2.

FIG. 21(A–C) taken together represent the amino acid sequence of the protein of FIG. 20, predicted from the nucleotide sequence of that figure.

Figure 22:
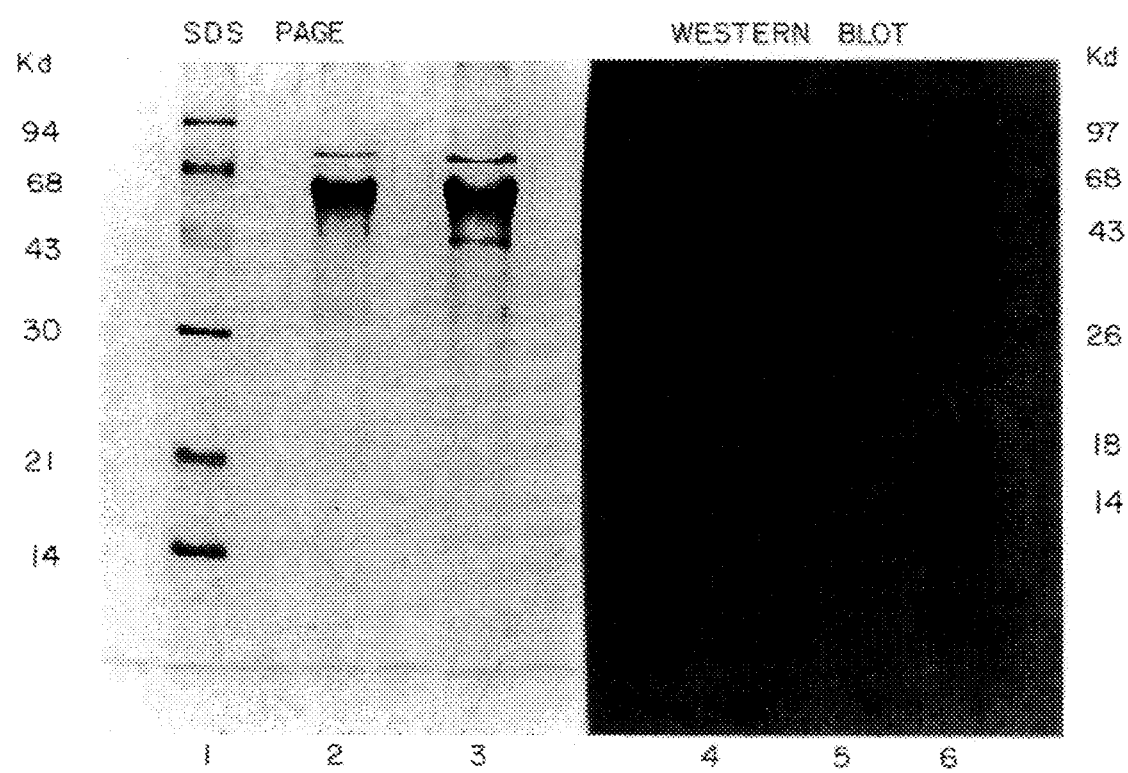

FIG. 22 is an SDS polyacrylamide gel electrophoretic analysis of the immunoaffinity-purified 65 kd protein. The gel was visualized by Coomassie blue stain and by Western blot analysis. Lanes 2 and 4 and 3 and 5 contain the purified protein from two preparations. Lanes 1 and 6 contain a mixture of molecular weight marker proteins having the molecular weights shown to the left and right of the figure.

FIG. 23 is an HPLC elution profile of a β-mercaptoethanol reduced (panel A) and unreduced (panel B) tryptic digest of the 65 kd protein, showing absorbance at 215 mμ as a function of column retention time.

Figure 24:
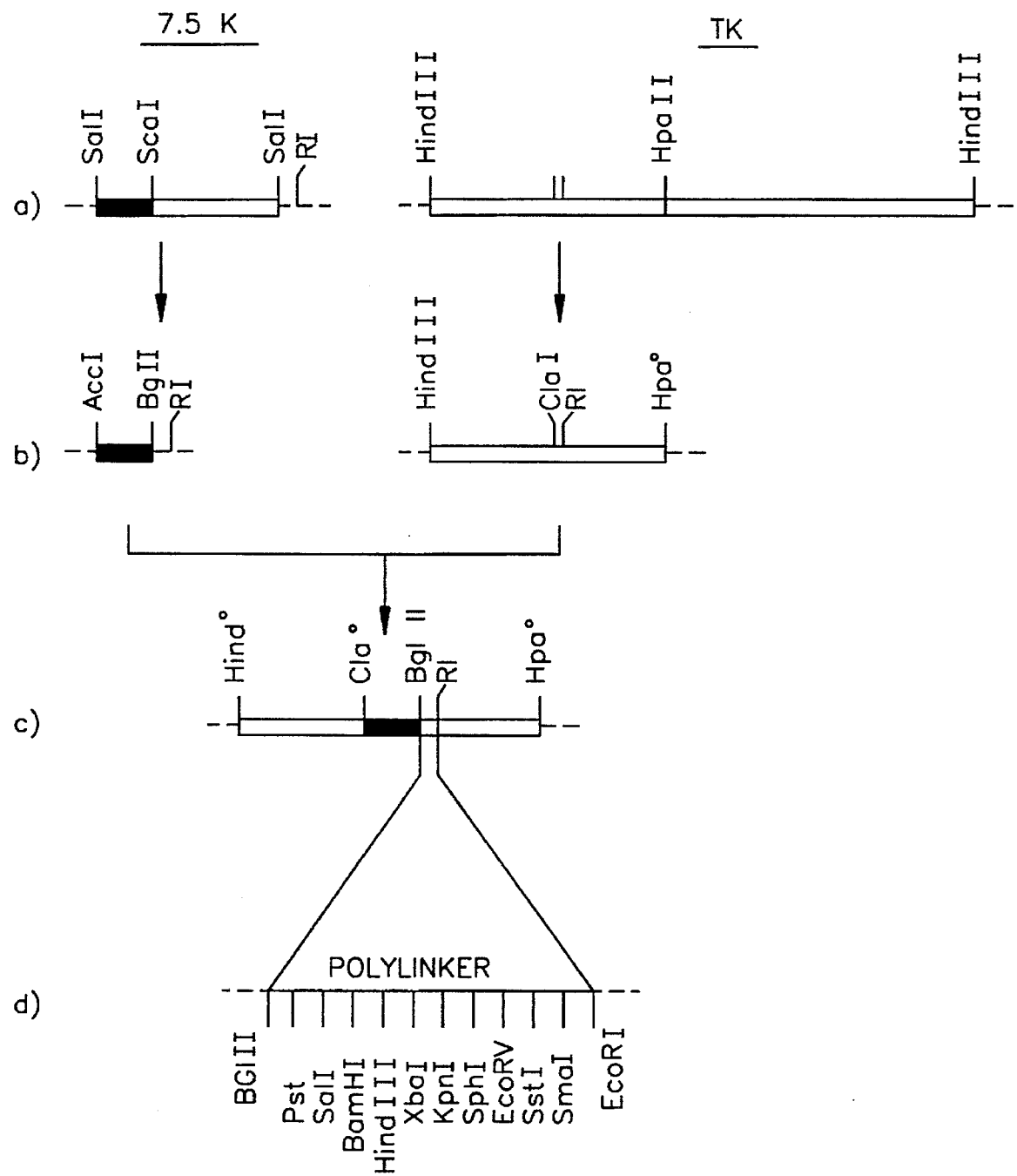

FIG. 24 shows restriction maps of four elements of the basic vector used for recombination of genes coding for coccidial antigens into vaccinia virus. These elements include the 7.5K promoter element (a and b, left), the TK locus (a and b, right), part of plasmid pUC8 (c) and the polycloning site from M13tg131 (d). The direction of transcription of the viral 7.5K and TK promoters is from left to right (i.e., from the BglII to the EcoRI restriction site in the polylinker.

FIG. 25 shows the amino acid sequence of the N-terminus of the Eimeria antigen recognized by monoclonal antibody 8A2 (A) expressed from a construct containing the AUG translation start codon in the polylinker element of the vector of FIG. 24, and (B) fused to the malarial 190 kd leader segment (first 34 amino acids) and the polylinker of the cloning vector of FIG. 24 (next 13 amino acids). During the maturation process of the protein, the first 19 amino acids at the N-terminus may be cleaved at the position indicated by a colon.

In the figures, standard single letter abbreviations are used to represent nucleotides, and standard one or three letter abbreviations are used to represent amino acids. The meanings of these abbreviations can be found in standard biochemistry textbooks, such as Lehninger, Principles of Biochemistry, 1984, Worth Publishers, Inc., New York, pp. 96, 798.

FIG. 26 is the nucleotide sequence of the DNA molecule encoding the approximately 20 kD protein recognized by monoclonal antibody 6A5 (ATCC Accession No. HB9711). This sequence represents the coding sequence only and encodes the amino acid sequence of FIG. 15. FIG. 26 is the subsequence from about nucleotide 91 to about nucleotide 741 of the sequence of FIG. 14. The first seven and last seven nucleotides of the sequence of FIG. 14 are derived from linker sequences used in the cloning procedure.

FIG. 27 is the nucleotide sequence of the DNA molecule encoding the approximately 65 kD protein recognized by monoclonal antibody 7D4 (ATCC Accession No. HB 9707). This sequence represents the coding sequence only and encodes the amino acid sequence of FIG. 17 from about residue 20 to about 325. FIG. 27 is the subsequence from about nucleotide 62 to about nucleotide 982 of the sequence of FIG. 16.

FIG. 28 is the amino acid sequence of the protein of FIG. 27 predicted from the nucleotide sequence of FIG. 27. This sequence is a subsequence of the sequence of FIG. 17 from about residue 20 to about 325. The 1st approximately 20 amino acids of FIG. 17 may result from an artifact during cDNA synthesis which caused "looping back" of a more internal sequence. Therefore, this sequence represents a more accurate sequence of the protein of FIG. 27.

FIG. 29 is the nucleotide sequence of the DNA molecule encoding the approximately 28 to approximately 37 kD protein recognized by monoclonal antibody 8A2 (ATCC Accession No. HB 9710). This sequence represents a resequencing of the DNA molecule from which the sequence of FIG. 18 was derived.

FIG. 30 is the nucleotide subsequence of the sequence of FIG. 29 which represents the coding sequence only as represented by FIG. 31.

FIG. 31 is the amino acid sequence of the protein of FIG. 29 deduced from the nucleotide sequence of FIG. 29. The resequencing suggests that the protein of FIG. 29 is approximately 37 kD.

FIG. 32 is the sequence of FIG. 31 from which the first three amino acids have been deleted. These three amino acids are encoded by nucleotides from linkers and are therefore artifacts of the cloning process.

FIG. 33 is the nucleotide sequence of the DNA molecule encoding the approximately 45 kD protein recognized by monoclonal antibody 7B2 (ATCC Accession No. HB 9712). This sequence represents the coding sequence only and encodes the amino acid sequence of FIG. 21 beginning at residue three. FIG. 33 is the subsequence from about nucleotide 9 to about nucleotide 3005 of the sequence of FIG. 20. The first seven and last seven nucleotides of the sequence of FIG. 20 are derived from linker sequences used in the cloning procedure.

FIG. 34 is the sequence of FIG. 21 from which the first two amino acids have been deleted. These two amino acids are encoded by nucleotides from linkers and are therefore artifacts of the cloning process.

5. DESCRIPTION OF THE INVENTION

5.1. Definitions

As used herein, the following terms shall have the following meanings:

"20 kd protein" means a recombinant or synthetic protein having an apparent molecular weight of about 20 kilodaltons in SDS polyacrylamide gel electrophoresis which binds specifically to monoclonal antibody 6A5. This antibody also specifically reacts with an Eimeria surface antigen (from a whole extract of Eimeria proteins) having an apparent molecular weight of about 28 kilodaltons in SDS gels. This antigen is present in the sporozoite developmental stage. The nucleotide sequence of a cDNA molecule encoding this protein and the amino acid sequence predicted therefrom are shown in FIGS. 14, 15, and 26.

"65 kd protein" means a recombinant or synthetic protein having an apparent molecular weight of about 65 kilodaltons in SDS polyacrylamide gel electrophoresis which binds specifically to monoclonal antibodies 7D1, 7D4 and 20C6. These antibodies also specifically react with a surface antigen from Eimeria extracts having an apparent molecular weight of about 120 kilodaltons in SDS gels. This antigen is present in the sporozoite, schizont and merozoite developmental stages. The nucleotide sequence of a cDNA molecule encoding this protein and the amino acid sequence predicted therefrom are shown in FIGS. 16 and 17, 27 and 28 respectively.

"28 kd protein" means a recombinant or synthetic protein having an apparent molecular weight of about 28 kilodaltons in SDS polyacrylamide gel electrophoresis which binds specifically to monoclonal antibody 8A2. This antibody also specifically reacts with an Eimeria surface antigen having an apparent molecular weight of about 37 kilodaltons in SDS gels. This antigen is present in the sporozoite, schizont and merozoite developmental stages. The nucleotide sequence of a cDNA molecule encoding this protein and the amino acid sequence predicted therefrom are shown in FIGS. 18 and 19, respectively. *

\* This cDNA has been resequenced, and the resulting nucleotide sequence and amino acid sequence predicted therefrom are shown in FIGS. 29, 30, 31, and 32.

"45 kd protein" means a recombinant or synthetic protein having an apparent molecular weight of about 45 kilodaltons in BDS polyacrylamide gel electrophoresis which binds specifically to monoclonal antibody 7B2. This antibody also specifically reacts with an Eimeria surface antigen having an apparent molecular weight of greater than 200 kilodaltons in SDS gels. This antigen is present in the sporozoite developmental stage. The nucleotide sequence of a cDNA molecule encoding this protein and the amino acid sequence predicted therefrom are shown in FIGS. 20 and 21, 33 and 34 respectively.

The term "protein having one or more immunoreactive and/or antigenic determinants of an Eimeria surface antigen" means a protein having one or more regions or epitopes which are capable of eliciting an immune response in an immunologically competent host organism and/or are capable of specifically binding to a complementary antibody.

Because of the degeneracy of the genetic code it will be understood that there are many potential nucleotide sequences (functional equivalents) that could code for the amino acid sequences shown in FIGS. 15, 17, 19, 21, 28, 31, 32, 34 It should also be understood that the nucleotide sequences of the DNA sequences and fragments of the invention inserted into vectors may include nucleotides which are not part of the actual structural genes, as long as the recombinant vectors containing such sequences and fragments are capable of directing the production in an appropriate host organism of a protein or fragment having one or more immunoreactive and/or antigenic determinants of an Eimeria surface antigen.

Moreover, amino acid substitutions in proteins which do not essentially alter biological and immunological activities have been known to occur and have been described, e.g., by Neurath et al. in "The Proteins", Academic Press, New York (1979), in particular in FIG. 6 at page 14. The most frequently observed amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and vice versa.

Such functionally equivalent nucleotide sequence variations and amino acid substitutions of the exemplary embodiments of this invention are within the scope of the invention as long as the resulting proteins retain one or more immunoreactive and/or antigenic determinants of an Eimeria surface antigen.

The term "fragment" means a DNA sequence or protein comprising a subsequence of one of the cDNA's or proteins of the invention. Such fragments can be produced by enzymatic cleavage of the larger molecules, using restriction endonucleases for the DNA and proteases for the proteins. The fragments of the invention, however, are not limited to the products of any form of enzymatic cleavage but include subsequences, the termini of which do not correspond to any enzymatic cleavage points. Such fragments can be made, e.g., by chemical synthesis, using the sequence data provided herein. DNA fragments can be produced by incomplete complementary DNA (cDNA) synthesis from isolated messenger RNA (mRNA). Protein fragments can also be produced by expressing DNA fragments encoding the protein fragments. Such protein fragments can be useful in this invention if they contain a sufficient number of amino acid residues to constitute an immunoreactive and/or antigenic determinant. Generally, at least about 7 or 8 residues are needed. As explained below, it may be necessary to couple such fragments to an immunogenic carrier molecule, to make them immunoreactive.

5.2. Preparation of Coccidial Proteins

The proteins of this invention can be made my methods known in the art such as by recombinant DNA methodology, chemical synthesis or isolation from Eimeria preparations.

5.2.1. Recombinant DNA

DNA needed to make the proteins of this invention could be chemically synthesized, using the nucleotide sequence information provided in FIGS. 14, 16, 18, 20, 26, 27, 29, 33. Such chemical synthesis could be carried out using any of the known methods, although the phosphoramidite solid support method of Matteucci et al. [J. Am. Chem. Soc. 103:3185 (1981)] is preferred.

Alternatively, cDNA can be made from Eimeria mRNA. Messenger RNA can be isolated from Eimeria sporulating oocysts or merozoites using standard techniques. These mRNA samples can then be used to produce double-stranded cDNA as described by Maniatis et al., supra. This cDNA can then be inserted into an appropriate cloning vector which can be used to transform *E. coli*, to produce a cDNA library.

The cDNA library can then be screened using the cloned genes of this invention, or fragments thereof, as probes. Such genes or fragments can be radiolabeled, e.g., by nick-translation using Pol I DNA polymerase in the presence of the four deoxyribonucleotides, one of which contains $^{32}$P in the α position (Maniatis et al., supra, p. 109), for use as probes.

Although *Eimeria tenella* was used as an mRNA source in the Examples below, the cloned genes from this species can be used as probes to isolate genes from other species of Eimeria, due to DNA sequence homology among the various species.

Once identified and isolated, the Eimeria genes of this invention are inserted into an appropriate expression vehicle which contains the elements necessary for transcription and translation of the inserted gene sequences. Useful cloning vehicles may consist of segments of chromosomal, nonchromosomal and synthetic DNA sequences such as various known bacterial plasmids, phage DNA, combinations of plasmids and phage DNA such as plasmids which have been modified to employ phage DNA or other expression control sequences, or yeast plasmids. Specific cloning vehicles which could be used include but are not limited to the pEV-vrf plasmids (pEV-vrf1, -2 and -3); SV40; adenovirus; yeast; lambda gt-WES-lambda B; Charon 4A and 28; lambda-gt-1-lambda B; M13-derived vectors such as pUC8, 9, 18 and 19, pBR313, 322 and 325; pAC105; pVA51; pACY177; pKH47; pACYC184; pUB110; pMB9; colE1; pSC101; pML21; RSF2124; pCR1 or RP4.

The insertion of the Eimeria genes into a cloning vector is easily accomplished when both the genes and the desired cloning vehicle have been cut with the same restriction enzyme or enzymes, since complementary DNA termini are thereby produced. If this cannot be accomplished, it may be necessary to modify the cut ends that are produced by digesting back single-stranded DNA to produce blunt ends, or by achieving the same result by filling in the single-stranded termini with an appropriate DNA polymerase. In this way, blunt-end ligation with an enzyme such as T4 DNA ligase may be carried out. Alternatively, any site desired may be produced by ligating nucleotide sequences (linkers) onto the DNA termini. Such linkers may comprise specific oligonucleotide sequences that encode restriction site recognition sequences. The cleaved vector and the Eimeria genes may also be modified by homopolymeric tailing, as described by Morrow [Methods in Enzymology 68:3 (1979)].

Many of the cloning vehicles that may be used in this invention contain one or more marker activities that may be used to select for desired transformants, such as ampicillin and tetracycline resistance in pBR322, ampicillin resistance and β-galactosidase activity in pUC8, and ampicillin resistance in pEV-vrf2. Selection of host cells into which such vectors have been inserted is greatly simplified when the host cells otherwise lack the activities contributed by the vectors.

It should be understood that the nucleotide sequences of the Eimeria genes inserted at a selected site in a cloning vehicle may include nucleotides which are not part of the actual structural genes. Alternatively, the gene may contain only part of the complete wild-type gene. All that is required is that the gene fragments inserted into the cloning vehicle be capable of directing the production in an appropriate host organism of a polypeptide or protein having at least one immunoreactive and/or antigenic determinant of an Eimeria surface antigen.

The selection of an appropriate host organism is affected by a number of factors known in the art. These factors include, for example, compatibility with the chosen vector, toxicity of proteins encoded by the hybrid plasmid, ease of recovery of the desired protein, expression characteristics, biosafety and costs. A balance of these factors must be struck, and it must be understood that not all hosts will be equally effective for expression of a particular recombinant DNA molecule.

Suitable host unicellular organisms which can be used in this invention include but are not limited to plant, mammalian or yeast cells and bacteria such as *Escherichia coli*, *Bacillus subtilis*, *Bacillus stearothermophilus* and Actinomyces. Especially preferred is *Escherichia coli* strain MC1061, which has been described by Casadaban et al. [J. Mol. Biol. 138:179 (1980)]. This strain can be used, or any other strain of *E. coli* K-12 containing the plasmid pRK248cIts. Plasmid pRK248cIts for use in other *E. coli* K-12 strains is available from the American Type Culture Collection and has accession No. ATCC 33766. *E. coli* strain MC1061 has also been deposited and has accession No. ATCC 53338.

Transfer of the recombinant cloning vector into the host cell may be carried out in a variety of ways. Depending upon the particular vector/host cell system chosen, such transfer may be effected by transformation, transduction or transfection. Once such a modified host cell is produced, the cell can be cultured and the protein expression product may be isolated from the culture.

5.2.1.1. Identification of Clones

Clones producing the Eimeria proteins of the invention can be identified using suitably labeled antibodies specific for the proteins. Monoclonal antibodies, which are preferred, can be prepared using standard methods as follows.

Antigenic proteins from *Eimeria tenella* are used to immunize animals such as mice, rats, horses, sheep, pigs, rabbits, etc., to obtain antibody producing somatic cells for fusion to myeloma cells.

Somatic cells with the potential for producing antibody, particularly B cells, are suitable for fusion with a myeloma cell line. These somatic cells may be derived from the lymph nodes, spleens and peripheral blood of primed animals. In the preferred embodiment of this invention mouse spleen cells are used, in part because these cells produce a relatively high percentage of stable fusions with mouse myeloma lines. It would be possible, however, to use rat, rabbit, frog or other cells instead.

Specialized myeloma cell lines have been developed from lymphocytic tumors for use in hyridoma-producing fusion procedures [Kohler and Milstein, Eur. J. Immunol. 6:511 (1976): Shulman et al., Nature 276:269 (1978): Volk et al., J. Virol. 42:220 (1982)]. These cell lines have been developed for at least three reasons. The first is to facilitate the selection of fused hybridomas among unfused and similarity indefinitely self-propogating myeloma cells. Usually this is accomplished by using myelomas with enzyme deficiencies that render them incapable of growing in certain selective media that support the growth of hybridomas. The second reason arises from the inherent ability of lymphocytic tumor cells to produce their own antibodies. The purpose of using monoclonal techniques is to obtain fused hybrid cell lines with unlimited lifespans that produce the desired single antibody under the genetic control of the somatic cell component of the hybridoma. To eliminate the production of tumor cell antibodies by the hybridomas, myeloma cell lines incapable of producing light or heavy immunoglobulin chains or deficient in antibody secretion mechanisms are used. A third reason for selection of these cell lines is for their suitability and efficiency for fusion.

Many myeloma cell lines may be used for the production of fused cell hybrids, including, e.g., P3/X63-Ag 8, P3/NSI/1-Ag 4-1, SP2/0-Ag-14 and S194/5.XXO.BU.1. The P3/X63-Ag 8 and P3/NSI/1-Ag 4-1 cell lines have been described by Kohler and Milstein [Eur. J. Immunol. 6:511, (1976)]. Shulman et al. [Nature 276:269 (1978)] developed the Sp2/0-Ag14 myeloma line. The S194/5.XXO.BU.1 line was reported by Trowbridge [J. Exp. Med. 148:313 (1979)]. In the example of the present invention, the PAI-O mouse cell line (a non-Ig-producing subclone of P3/X63-Ag 8) was used.

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promote the fusion of cell membranes. It is preferred that the same species of animal serve as the source of the somatic and myeloma cells used in the fusion procedure. Fusion methods have been described by Kohler and Milstein [Nature 256:495 (1975) and Eur. J. Immunol. 6:511 (1976)], by Gefter et al. [Somatic Cell Genet. 3:231 (1977)], and by Volk et al. (J. Virol. 42:220 (1982)]. The fusion-promoting agents used by those investigators were Sendai virus and polyethylene glycol (PEG). The fusion procedure for the example of the present invention uses PEG.

Because fusion procedures produce viable hybrids at very low frequency (e.g., when spleens are used as a source of somatic cells, only one hybrid is obtained for roughly every $1 \times 10^5$ spleen cells), it is essential to have a means of selecting the fused cell hybrids from the remaining unfused cells, particularly the unfused myeloma cells. A means of detecting the desired antibody-producing hybridomas among other resulting fused cell hybrids is also necessary.

Generally, the selection of fused cell hybrids is accomplished by culturing the cells in media that support the growth of hybridomas but prevent the growth of the myeloma cells, which normally would go on dividing indefi-
nitely. (The somatic cells used in the fusion do not maintain long-term viability in in vitro culture and hence do not pose a problem). In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody so that they may subsequently be cloned and propagated. Generally, around 10% of hybrids obtained produce the desired antibody, although a range of from 1 to 30% is not uncommon. The detection of antibody-producing hybrids can be achieved by any one of several standard assay methods, including enzyme-linked immunoassay and radioimmunoassay techniques which have been described in the literature [see, e.g., Kennet et al. (editors), Monoclonal Antibodies and Hybridomas: A New Dimension in Biological Analyses, pp. 376–384, Plenum Press, New York (1980)]. Several detection methods were used in the example of the present invention.

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation.

5.2.1.2. Cell Disruption

As produced in *E. coli*, the Eimeria proteins remain in the cytoplasm, or in inclusion bodies. To free the proteins it is thus necessary to disrupt the outer membrane. This is preferably accomplished by sonication, or by other mechanically disruptive means, such as a French pressure cell or Gaulin homogenizer.

Cell disruption could also be accomplished by chemical or enzymatic means. Since divalent cations are often required for cell membrane integrity, treatment with appropriate chelating agents such as EDTA or EGTA might prove sufficiently disruptive to facilitate the leakage of the proteins from the cells. Similarly, enzymes such as lysozyme have been used to achieve the same result. That enzyme hydrolyzes the peptidoglycan backbone of the cell wall.

The application of osmotic shock could also be employed. Briefly, this could be accomplished by first placing the cells in a hypertonic solution which would cause them to lose water and shrink. Subsequent placement in a hypotonic "shock" solution would then lead to a rapid influx of water into the cells with an expulsion of the desired proteins.

Once freed from the cells, the Eimeria proteins may be concentrated by precipitation with salts such as sodium or ammonium sulfate, ultrafiltration or other methods well known to those skilled in the art. Further purification could be accomplished by conventional protein purification techniques including but not limited to gel filtration, ion-exchange chromatography, preparative disc-gel or curtain electrophoresis, isoelectric focusing, low temperature organic solvent fractionation, or countercurrent distribution. Purification is preferably carried out, however, by immunoaffinity chromatography as described below.

5.2.2. Chemical Synthesis

The proteins of this invention or fragments thereof can also be chemically synthesized by a suitable method such as by exclusive solid phase synthesis, partial solid phase methods, fragment condensation or classical solution synthesis. Solid phase synthesis as described by Merrifield [J. Am. Chem. Soc. 85:2149 (1963)] is preferred.

Such synthesis is carried out with amino acids that are protected at the alpha-amino-terminus. Trifunctional amino acids with labile side-chains are also protected with suitable groups which will prevent a chemical reaction from occurring at that site during the assemblage of the peptide. The alpha-amino protecting group is selectively removed to allow subsequent reaction to take place at the amino-terminus. The conditions for the removal of the alpha-amino protecting group do not cause deprotection of the side-chain protecting groups.

The alpha-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarbonyl (Cbz) and substituted benzyloxycarbonyl), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). The preferred protecting group is Boc. The side-chain protecting groups for Tyr include tetrahydropyranyl, tert.-butyl, triyl, benzyl, Cbz, 4-Br-Cbz and 2,6-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group for Asp is cyclohexyl. The side-chain protecting groups for Thr and Ser include acetyl, benzoyl, trityl, tetrahydropyranyl, benzyl, 2,6-dichlorobenzyl and Cbz. The preferred protecting group for Thr and Ser is benzyl. The side-chain protecting groups for Arg include nitro, Tos, Cbz, adamantyloxycarbonyl or Boc. The preferred protecting group for Arg is Tos. The side-chain amino group of Lys may be protected with Cbz, 2-ClCbz, Tos or Boc. The 2-Cl -Cbz group is the preferred protecting group for Lys. The selection of the side-chain protecting group is based on the following: The side-chain protecting group remains intact during coupling and is not split off during the deprotection of the amino-terminus protecting group or during coupling conditions. The side-chain protecting group must be removable upon the completion of the synthesis of the final peptide, using reaction conditions that will not alter the target peptide.

Solid phase synthesis is usually carried out from the carboxy-terminus by coupling the alpha-amino protected (side-chain protected) amino acid to a suitable solid support. An ester linkage is formed when the attachment is made to a chloromethylated or hydroxymethyl resin and the resultant target peptide will have a free carboxyl group at the C-terminus. Alternatively, a benzhydrylamine or p-methylbenzhydrylamine resin is used in which case an amide bond is formed and the resultant target peptide will have a carboxamide group at the C-terminus. These resins are commercially available and their preparation is described by Stewart et al., "Solid Phase Peptide Synthesis" (2nd Edition, Pierce Chemical Co., Rockford, Ill., 1984).

The C-terminal amino acid, Arg, protected at the side-chain with Tos and at the alpha-amino function with Boc is coupled to the benzhydrylamine resin using various activating agents including dicyclohexylcarbodiimide (DCC), N,N'-diisopropylcarbodiimide and carbonyldiimidazole. Following the attachment to the resin support the alpha-amino protecting group is removed by using trifluoroacetic acid (TFA) or HCl in dioxane at a temperature between 0° and 25° C. Dimethylsulfide is added to the TFA after the introduction of methionine (Met) to suppress possible S-alkylation. After removal of the alpha-amino protecting group, the remaining protected amino acids are coupled stepwise in the required order to obtain the desired peptide sequence.

Various activating agents can be used for the coupling reactions including DDC, N,N'-diisopropylcarbodiimide, benzotriazol-1-yl-oxy-tris-(dimethylamino)-phosphonium hexafluorophosphate (BOP) and DCC-hydroxybenzotriazole (HOBt). Each protected amino acid is used in excess (>2.5 equivalents), and the couplings are usually carried out in DMF, $CH_2Cl_2$ or mixtures thereof. The extent of completion of the coupling reaction is monitored at each stage by the ninhydrin reaction as described by Kaiser et al., Anal. Biochem. 34:595 (1970). In cases where incomplete coupling is determined the coupling reaction is repeated. The coupling reactions can be performed automatically on a Vega 250, Applied Biosystems synthesizer or other commercially available instrument. After the entire assemblage of the target peptide, the peptide-resin is deprotected with TFA/dithioethane and then cleaved with a reagen such as liquid HF for 1–2 hours at 0° C. which cleaves the peptide from the resin and removes all side-chain protecting groups.

Side-chain to side-chain cyclization on the solid support requires the use of an orthogonal protection scheme which enables selective cleavage of the side-chain functions of the acidic amino acids (e.g., Asp) and the basic amino acids (e.g., Lys). The 9-fluorenylmethyl (OFm) protecting group for the side-chain of Asp and the 9-fluorenylmethoxycarbonyl (Fmoc) protecting group for the side-chain of Lys can be used for this purpose. In these cases the side-chain protecting groups of the Boc-protected peptide-resin are selectively removed with piperidine in DMF. Cyclization is achieved on the solid support using various activating agents including DCC, DCC/HOBt or BOP. The HF reaction is carried out on the cyclized peptide-resin as described above.

Purification of the synthetic proteins can be carried out as described above for the recombinantly produced proteins.

5.2.3. Immunoprecipitation and Immunoaffinity Chromatography

Eimeria proteins can also be recovered from extracts of membrane proteins from E. tenella or other Eimeria species by immunoprecipitation or immunoaffinity chromatography. As already noted, such methods can produce the complete, wild-type proteins. In some cases, these proteins are larger than the proteins produced by recombinant DNA methodology. Monoclonal antibodies for this purpose can be produced as described above, using synthetic or natural Eimeria proteins as the antigen.

5.2.4. Anti-Idiotype Antibodies

Other useful proteins which have the necessary immunoreactive and/or antigenic determinants are antibodies or fragments thereof which are anti-idiotypic toward the active determinant or determinants on the proteins of the invention. Such anti-idiotypic antibodies can be raised against other antibodies which are specific for the determinants on the proteins of the invention (i.e., the anti-idiotypic antibodies are anti-antibodies). Preferably, monoclonal anti-idiotypic antibodies are used. Such antibodies can be administered as a vaccine, in the same manner that the Eimeria proteins themselves can be used.

5.3. Poultry Vaccination

5.3.1. Use of Eimeria Proteins and Anti-Idiotype Antibodies

One or more of the Eimeria proteins and anti-idiotype antibodies of this invention can be formulated into vaccines comprising the proteins and a physiologically acceptable carrier. Suitable carriers include, e.g., 0.01 to 0.1M phosphate buffer of neutral pH or physiological saline solution.

Enhanced immunity against coccidiosis can be produced in one of two ways. First, an adjuvant or immunopotentiator can be added to the vaccine. Secondly, the proteins of the invention can be presented to an animal that is to be immunized in a larger form, either as a cross-linked complex or conjugated to a carried molecule.

Suitable adjuvants for the vaccination of animals include but are not limited to Adjuvant 65 (containing peanut oil, mannide monooleate and aluminum monostearate); mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The proteins could also be administered following incorporation into liposomes or other microcarriers.

Incorporation into liposomes or other microcarriers provides a means by which the release of the vaccines can be sustained over a prolonged period of time. A pump such as an Alza pump could be used for the same purpose.

The immunogenicity of the proteins of the invention, especially the smaller fragments, can be enhanced by cross-linking or by coupling to an immunogenic carrier molecule (i.e., a macromolecule having the property of independently eliciting an immunological response in a host animal, to which the proteins and protein fragments of the invention can be covalently linked). Cross-linking or conjugation to a carrier molecule may be required because small protein fragments sometimes act as haptens (molecules which are capable of specifically binding to an antibody but incapable of eliciting antibody production, i.e., they are not immunogenic). Conjugation of such fragments to an immunogenic carrier molecule renders the fragments immunogenic through what is commonly known as the "carrier effect".

Suitable carrier molecules include, e.g., proteins and natural or synthetic polymeric compounds such as polypeptides, polysaccharides, lipopolysaccharides etc. A useful carrier is a glycoside called Quil A, which has been described by Morein et al., Nature 308:457 (1984). Protein carrier molecules are especially preferred, including but not limited to mammalian serum proteins such as keyhole limpet hemocyanin, human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the Eimeria proteins are to be elicited.

Covalent coupling to the carrier molecule can be carried out using methods well known in the art, the exact choice of which will be dictated by the nature of the carrier molecule used. When the immunogenic carrier molecule is a protein, the proteins or fragments of the invention can be coupled, e.g., using water soluble carbodiimides such as dicyclohexylcarbodiimide, or glutaraldehyde.

Coupling agents such as these can also be used to cross-link the proteins and fragments to themselves without the use of a separate carrier molecule. Such cross-linking into protein or protein fragment aggregates can also increase immunogenicity.

Administration of an effective amount of the vaccines of this invention can protect poultry against infection by E. tenella. Monoclonal antibodies against the E. tenella antigens cross-react with E. acervulina and E. maxima in vitro, indicating that protection may also be conferred against these species. An effective dose of the proteins or protein fragments ranges from about 10 to about 50 micrograms/kg of body weight of the vaccinated animal. A dose of about 25–50 µg/kg is preferred. Initial vaccinations are preferably followed by booster vaccinations given from one to several weeks later. Multiple boosters may be administered. The dosages of such boosters generally range from about 5 to 50 µg/kg, preferably about 20–50 µg/kg. Standard routes of administration can be used such as subcutaneous, intradermal, intramuscular, oral, anal or in ovo administration.

5.3.2. Vector Systems

The presentation of the coccidial antigens of the invention to the immune systems of fowl can be achieved by cloning genes coding for the antigens into bacteria (e.g., E. coli or Salmonella) or into viruses (e.g., poxviruses or herpesviruses) and administering the live vector systems to the birds orally, by injection or by other commonly used routes. Carbit et al. [in: Vaccines, 1987, Cold Spring Harbor Laboratory, pp. 68–71] have described the use of E. Coli, while Clements [Pathol. Immunopathol. Res. 6:137 (1987)] has described the use of Salmonella. Moss et al. [Ann. Rev. Immunol. 5:305 (1987)] have reviewed the use of viral vector systems employing recombinant poxviruses.

One kind of poxvirus, vaccinia virus, can be used to test the delivery of coccidial antigens in cell culture and in animals. For analytical studies, vaccinia virus has been found to be more efficient than fowlpox virus, another poxvirus carrier that can be used. This is because vaccinia virus multiplies more rapidly than the arian virus and has a host range that is not restricted to chicken cells. Large amounts of heterologous DNA can be inserted into the vaccinia viral genome without inhibiting viral maturation and infectivity [Smith et al., Gens 25:21 (1983)]. The insertion and expression of multiple heterologous genes using the virus elicits antibody production against expressed antigens in infected animals [Perkus et al., Science 229:981 (1985)].

The techniques used to produce recombinant vaccinia viruses can be readily adapted by routine procedures to fowlpox or herpesvirus systems. The use of such recombinant viruses as carriers in vaccines against coccidiosis is especially advantageous in that vaccinated fowl develop immunity against both the coccidial antigen and the viral carrier (i.e., such vaccines are bivalent). The utility of such vaccines can be further enhanced by inserting additional genes into the carrier virus. For example, parts of the Newcastle disease viral genome can be inserted together with a coccidial antigen gene into a fowlpox virus, thereby conferring immunity against Newcastle disease, coccidiosis and fowlpox, all with a single vaccine.

The administration of the live vector vaccines of the invention can be carried out by numerous methods well known in the art. For example, the "stick" method commonly used to vaccinate poultry against fowlpox virus can be used. This method consists of sticking or pricking the skin of the wing web with a sharp needle dipped into the vaccine. The needle usually has an eye near the tip like a sewing machine needle which carries a drop of vaccine. Alternatively, the live vaccines can be injected subcutaneously or intradermally into the wing web or any other site.

The recombinant live vector vaccines can also be added to drinking water or even sprayed over chicks that are to be vaccinated. They can also be administered in feed, preferably after protective encapsulation [Balancou et al., Nature 322:373 (1986)], or in ovo. In the latter method, the viral vaccines are injected directly into chicken embryos [Sharma, Avian Dis. 25:1155 (1985)].

6. EXAMPLES

Unless otherwise specified, percentages given below for solids in solid mixtures, liquids in liquids, and solids in liquids are on a wt/wt, vol/vol and wt/vol basis, respectively.

6.1. Preparation of Monoclonal Antibodies Against Eimeria Antigens

6.1.1. Parasite Preparation

Sporozoites of *E. tenella*, *E. acervulina*, *E. brunetti*, and *E. maxima* were isolated from sporulated oocysts by standard procedures. Briefly, sporulated oocysts were washed with distilled water and 20% bleach and then with distilled water. The oocysts were disrupted in a tissue homogenizer and insoluble material, including sporocysts, was recovered by centrifugation. The released sporocysts and other material in the pellet were resuspended in 0.25% trypsin and chicken bile in Hank's salt solution, pH 8, and incubated for 2 hours at 40° C. The excising solution was removed by two washes with RPMI-1640 medium containing 10% fetal bovine serum (FBS), followed by two washes with PBS at pH 7.4.

The sporozoites were then purified over a metrazimide gradient [Wisher et al., Parasitiology 88:515 (1984)]. Briefly, the sporozoites were resuspended in 2 ml of PBS, pH 7.0, and 1 ml of the suspension was layered over a 15 ml metrizamide gradient. The gradient was composed of 5 ml of each of 12%, 18% and 24% metrazimide in PBS, pH 7.0. The sporozoites were sedimented by centrifugation at 900×g for 40 minutes. Purified sporozoites were isolated from the interface between the 18% and 24% metrizamide by insertion of a 21 gauge needle through the side of the tube and aspirating the sporozoites into a syringe.

The purified sporozoites were washed 3 times with PBS, pH 7.0 and used immediately for immunizations, infection studies, surface labeling with $^{125}I$, immunofluorescence assays or SDS-polyacrylamide gel electrophoresis [Laemmli, Nature 227:680 (1970)] and Western blotting studies.

Merozoites of *E. tenella* were isolated as described below in Section 6.2.3. The purified merozoites were used for immunizations and were solubilized with Laemmli sample buffer for SDS-polyacrylamide gel electrophoresis and Western blotting studies.

6.1.2. Immunizations

Eight female Balb/c mice (Charles River, Wilmington, Mass.) were immunized with purified live sporozoites according to the following schedule.

Figure 1:
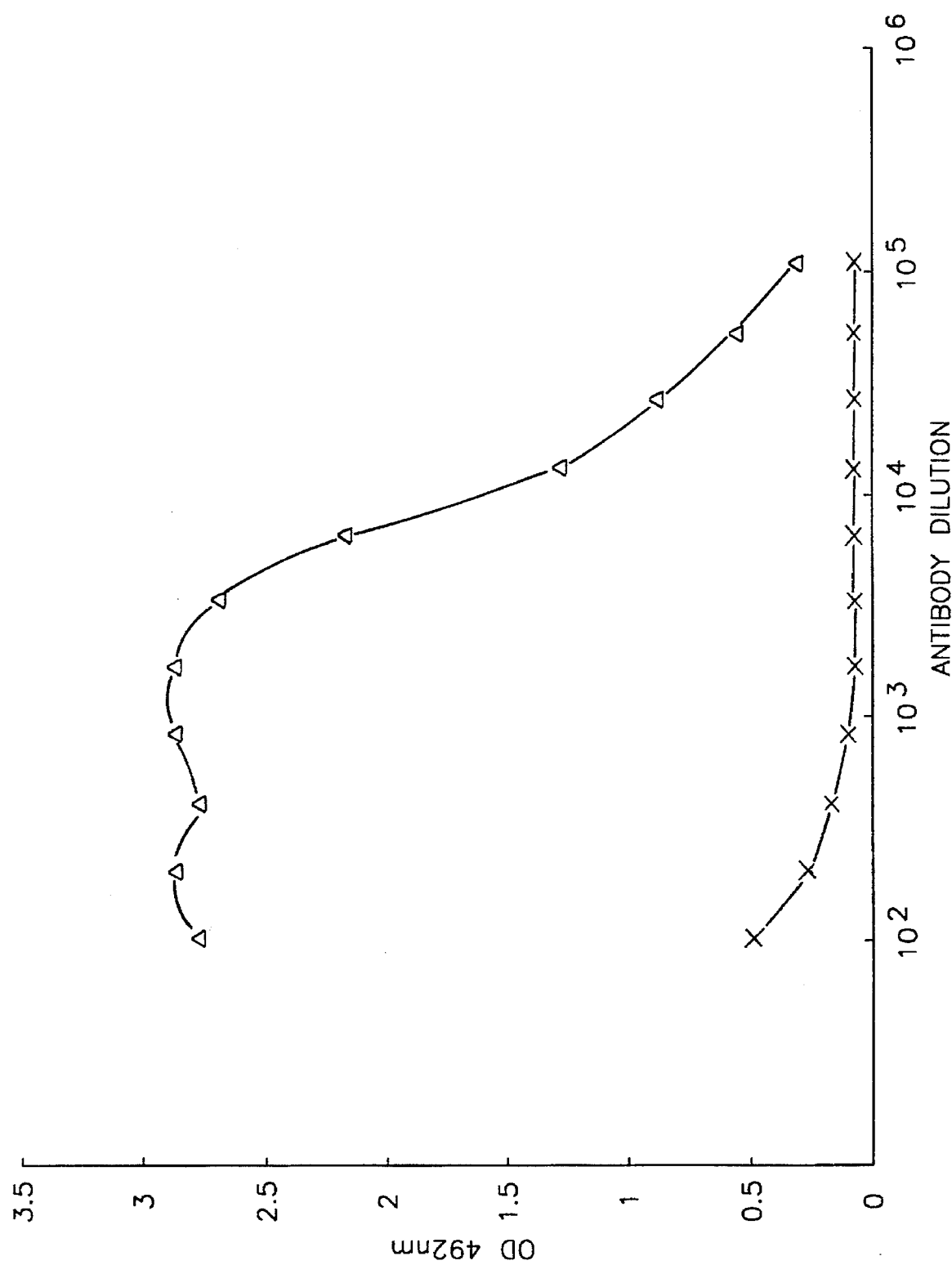

Day 1 1×10$^7$ sporozoites intravenously (i.v.)
Day 7 6×10$^6$ sporozoites intraperitoneally (i.p.)
Day 85 6×10$^6$ sporozoites i.p.
Day 120 3×10$^7$ sporozoites i.p.
Day 244 Pre-fusion immunization boosters
Day 1 5×10$^6$ sporozoites i.v., 5×10$^6$ sporozoites i.p.
Day 2 same as Day 1
Day 5 fusion of hyperimmune splenocytes and myeloma cells The serum from each mouse was tested for anti-sporozoite antibodies by ELISA with purified sporozoite proteins, by Western blotting assays with solubilized sporozoite proteins, by immunoprecipitation of $^{125}I$-labeled sporozoite surface proteins, and by immunofluorescence assays with purified sporozoites. The mouse with the highest sporozoite antibody reactivity (mouse 107-2) was chosen for the pre-fusion immunization boosters (see FIG. 1 for ELISA analysis of this antiserum). On the fifth day, the mouse was killed and the spleen was removed for the preparation of splenocytes.

6.1.3. Cell Culture and Cell Fusions

Two days before fusion, splenocyte feeder cells were prepared from naive mice in complete medium [Iscove's modified Dulbecco's medium (IMDM, Gibco) with 10% FBS, glutamine (2.0 mM), and 2-mercaptoethanol (100 µM)] plus HAT (100 µmM hypoxanthine, 0.4 µM aminopterin and 16 µM thymidine). Using a modification of the procedure of de St. Groth et al. [J. Immunol. Methods 35:1 (1980)], 10$^8$ spleen cells were fused with 10$^8$ PAI-O mouse myeloma cells.

The cells were mixed, pelleted by centrifugation and resuspended under constant gentle agitation in 1.0 ml of 35% (vol/vol) polyethylene glycol in IMDM at 37° C. over 1 minute. After 3 minutes of incubation at 37° C., the cells were pelleted again and gently resuspended in 10 ml of IMDM+HAT. The cells were then diluted to 1×10$^6$ cells/ml in complete medium +HAT and dispersed into 24-well microtiter plates (1 ml/well) containing 5×10$^5$ splenocyte feeder cells in 1 ml of complete medium.

Hybridoma supernatants were assayed for anti-sporozoite antibodies by ELISA with purified sporozoites, by Western blotting with sporozoite proteins, by immunoprecipitation with $^{125}I$-labeled sporozoite surface proteins and by immunofluorescence with purified sporozoites and with sporozoite-infected cells. The hybridomas were cloned by limiting dilution.

6.1.4. Sporozoite Elisa

Purified sporozoites (4×10$^4$) were added to each well of a 96-well U-bottom PVC plate which had previously been blocked with 1% BSA in PBS, pH 7.0. The sporozoites were sedimented to the bottom of the wells by centrifugation at 1000×g for 5 minutes. The sporozoites were resuspended in 100 µl of diluted antiserum or hybridoma supernatants and incubated for 2 hours at room temperature with constant agitation. The sporozoites were then washed with 1% BSA in PBS, pH 7.0, to remove unbound antibody.

To detect specific antibody bound to the sporozoites, 100 µl of peroxidase-conjugated goat anti-mouse IgG were added to the resuspended sporozoites, and the suspension was incubated for 2 hours at room temperature. The sporozoites were washed, and bound antibody was visualized by adding substrate solution (o-phenylenediamine, 0.4 mg/ml in 0.1M citrate buffer, pH 4.5., 0.12% hydrogen peroxide) for 30 minutes at room temperature. The reaction was stopped by the addition of 2.5M $H_2SO_4$ containing 50 mM sodium metabisulfite. The amount of bound antibody was determined by reading the OD$_{488}$ of the substrate color.

From a total of 480 wells plated from the cell fusion, 432 were positive for hybridoma growth. Of these, 358 hybridomas tested positive for antibody production in the primary sporozoite ELISA. During expansion and passage of these original parental hybridoma cells, 104 died or stopped producing antibody and thus were negative in subsequent screenings with the sporozoite ELISA and Western blot assays. The sporozoite ELISA identified 205 hybridomas which were producing antibody at 10×background levels.

6.1.5. Western Blotting of Sporozoite Proteins

Purified sporozoites (approximately $5 \times 10^7$ sporozoites per ml per gel) were solubilized in Laemmli sample buffer, separated by SDS-polyacrylamide gel electrophoresis in either a 12.5% gel or a 7.5 to 20% gradient gel (Laemmli, supra) and electrophoretically transferred to nitrocellulose sheets. The sheets were blocked in 3% gelatin buffer (3% gelatin, Tris-HCl, pH 7.5, 0.15M NaCl) and cut into strips, and the strips were allowed to react with diluted antiserum or hybridoma supernatant for 12 hours at 4° C. in 1% BSA buffer (1% BSA, 50 mM sodium phosphate, pH 6.5, 0.5M NaCl, 0.05% Tween-20). The strips were washed in PBS, pH 7.4, 0.05% Tween-20 and the specifically bound antibody was detected with a peroxidase-conjugated anti-mouse antibody. The bound antibodies were visualized by adding substrate solution [4-chloro-1-naphthol (30 mg dissolved in 10 ml of ice cold methanol and 50 ml of Tris-HCl, pH 7.5), 0.15M NaCl, 0.015% final concentration $H_2O_2$] for 30 minutes at room temperature. The reaction was terminated by extensive washing with distilled water.

Of the antibodies that were positive in the sporozoite ELISA, 160 were also positive by Western blotting analysis using solubilized sporozoite proteins.

Figure 2:
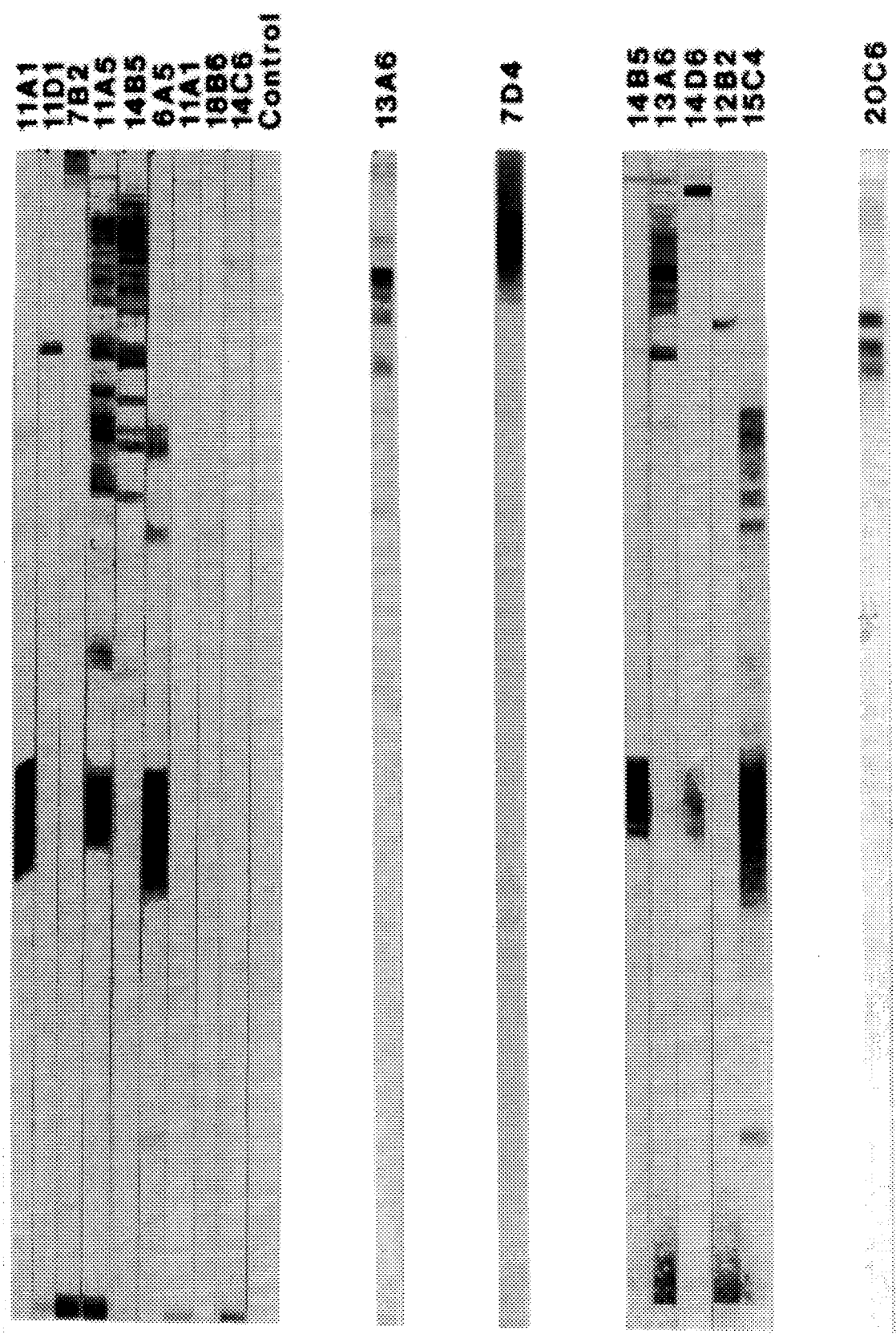

Western blot analysis (see FIG. 2) showed that the monoclonal antibodies fell into one of three reactivity patterns: (a) those which bind single Eimeria proteins (e.g., 11A1 and 11D1), (b) those which bind to 2 or 3 proteins (e.g., 6A5 and 20C6) and (c) those which bind to multiple proteins (e.g., 11A5, 13A6 and 14B5).

Figure 3:
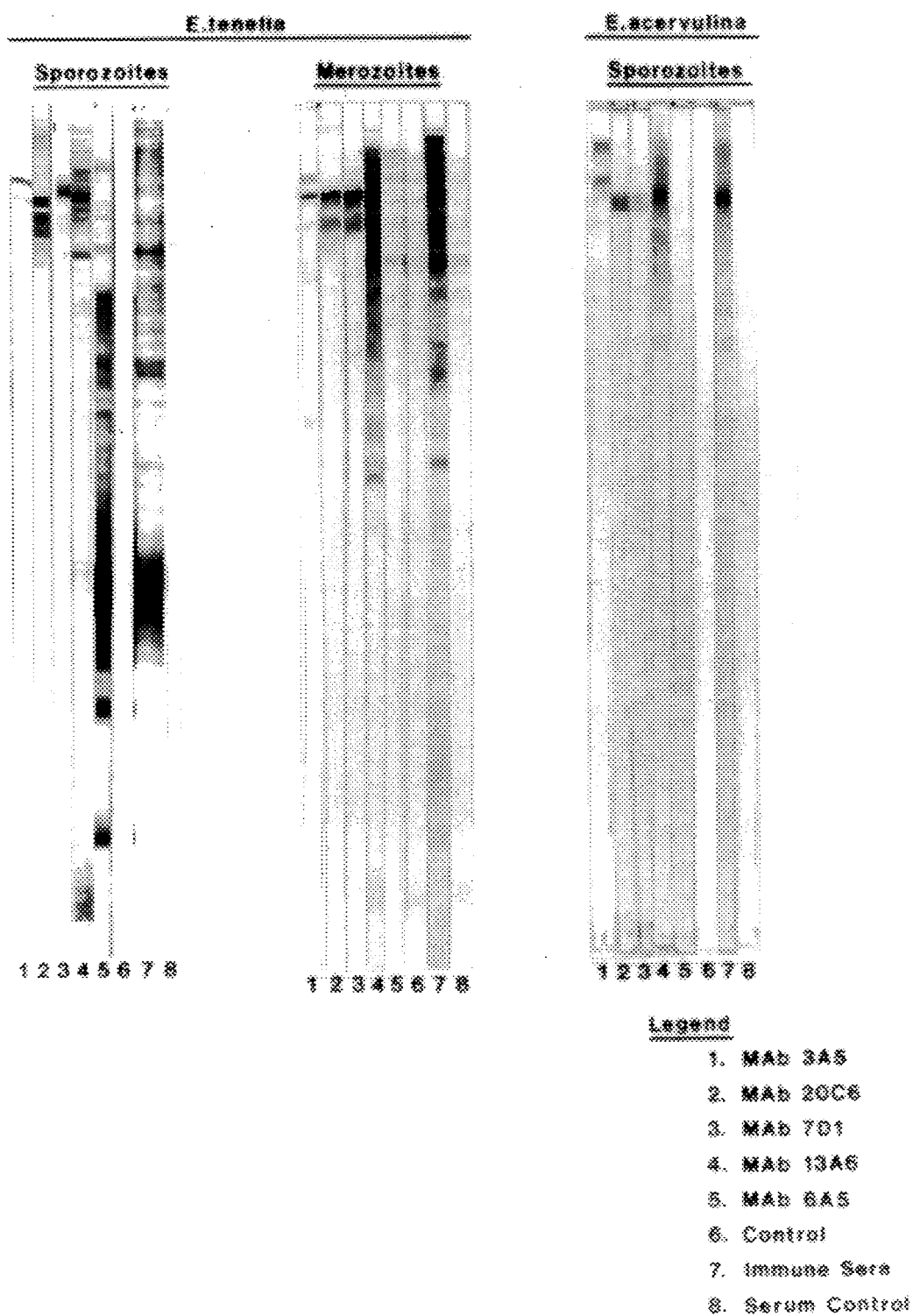

The antibodies were further characterized by Western blot analysis using *E. tenella* merozoite and *E. acervulina* sporozoite proteins (FIG. 3). A number of antibodies, including 3A5, 13A6, 7D1 and 20C6, recognized proteins isolated from sporozoites of *E. tenella* and *E. acervulina* and from merozoites of *E. tenella*. Other antibodies, such as 6A5, were shown to be species and stage specific and to bind only to proteins from *E. tenella* sporozoites.

A summary of results obtained on some of the antibodies is shown in Table 1, in which the specificity of the antibodies is shown both in terms of (a) the origin and size of the protein(s) in the gels to which the antibodies bound and (b) the size of $^{125}$I-labeled *Eimeria tenella* proteins precipitated by the antibodies (right column). The antibodies are further characterized in the Table by isotype.

TABLE 1

WEST BLOT ANALYSIS

| Anti-body | Isotype | Eimeria Protein (gel size in kd) | | | | Size of Protein Ppt. (kd) |
|---|---|---|---|---|---|---|
| | | Tenella | | Acervulina | Maxima | |
| | | Spz | Mrz | Spz | Spz | |
| 7B2 | $G_2$a | >200 | — | — | — | — |
| 7D4 | $G_1$ | 120 | 120 | 120 | — | 110 |
| 7D1 | $G_1$ | 120 | 120 | 120 | N.D. | 110 |
| 20C6 | $G_1$ | 120 | 120 | 120 | N.D. | 110 |
| 3A5 | M | 120 | 120 | 120 | 17 | 120 |
| 19D6 | $G_3$ | 180 | 180 | — | — | 120 |
| 8A2 | $G_{2a}$ | 37 | 37 | — | — | 37 |
| 6A5 | $G_{2b}$ | 28/26 | — | — | — | 25 |

TABLE 1-continued

WEST BLOT ANALYSIS

| Anti-body | Isotype | Eimeria Protein (gel size in kd) | | | | Size of Protein Ppt. (kd) |
|---|---|---|---|---|---|---|
| | | Tenella | | Acervulina | Maxima | |
| | | Spz | Mrz | Spz | Spz | |
| 14B5 | N.D. | >150 | N.D. | | | N.D. |
| 15B3 | N.D. | >150 | N.D. | | | N.D. |
| 14B1 | $G_3$ | 6 | 6 | — | — | 24/17 |
| 12B2 | $G_3$ | 28/26 | — | — | — | 24/17 |
| 15A3 | $G_1$ | 28/6 | — | — | — | 17/15/6 |
| 15C4 | M | 28/26 | — | — | — | 105/15/6 |
| 12C3 | $G_3$ | 28 | — | N.D. | N.D. | 25 |
| 5B6 | $G_3$ | — | N.D. | | | 6 |
| 3C4 | M | m | m | m | — | 70 |
| 16D2 | M | m | m | m | — | 70/85 |
| 13A6 | M | m | m | m | — | 110 |
| 11B6 | $G_3$ | m | m | m | — | 105 |
| 12A3 | $G_3$ | m | m | m | — | 24/17 |
| 12D4 | $G_1$ | m | N.D. | | | N.D. |

Spz and Mrz are abbreviations for sporozoite and merozoite, respectively.
G and M refer to IgG and IgM, respectively.
m indicates that the antibodies bound to multiple proteins ranging from 24 to more than 200 kd in size.
Values indicated by N.D. were not determined.

6.1.6. Immunoprecipitation of $^{125}$I-Labeled Sporozoite Surface Proteins

The surface proteins of purified sporozoites were labeled with $^{125}$I by the IODOGEN method (Pierce Chemical Co.) or by use of IODOBEADS (Pierce Chemical Co.). For the latter procedure, 4 IODOBEADS were washed 3× with 0.2M sodium phosphate, pH 7.5, and 1–3 mCi of $^{125}$I-Na were added and incubated for 5 minutes at room temperature. Purified sporozoites ($3 \times 10^8$) in 200 µl of PBS, pH 7.0, were added to the reaction vial, and the incubation was continued for 15 minutes. At the end of the incubation, phenylmethanesulfonyl fluoride (PMSF) was added to a final concentration of 0.5 mM.

The sporozoites were recovered from the incubation mixture by centrifugation at 12,000×g for 30 seconds and solubilized in 1 ml of either 2% sodium dodecysulfate (SDS) or 1% Triton X-100 in PBS, pH 7.0. Insoluble material was removed by centrifugation for 3 minutes at 12,000×g. The solubilized sporozoite proteins were dialyzed against 3 liters of PBS, pH 7.0, at 4° C. using a 3,500 molecular weight cutoff membrane to remove any residual free $^{125}$-I. The $^{125}$I-labeled sporozoite proteins (typically $1.5 \times 10^8$ cpm incorporated into protein) were stored at 4° C. until used. The TCA precipitable radioactivity was typically in excess of 95% of the total radioactivity. SDS polyacrylamide gel electrophoretic analysis of the $^{125}$I-labeled sporozoite proteins is shown in FIG. 4, left panel.

Immunoprecipitation was carried out by adding 300 µl of hybridoma supernatant or diluted antiserum to 250 µl of $^{125}$I-labeled sporozoite proteins ($1 \times 10^5$ cpm) in Buffer I (0.25% NP-40, 10 mM Tris-HCl, pH 7.5, 0.15M NaCl). Following incubation for 16 hours at 4° C., 100–200 µl of a 50% suspension of goat anti-mouse IgG coupled to agarose (Sigma Chemical Co.) were added, and the mixture was incubated on a rotating mixer for 2 hours at room temperature. The beads were pelleted by centrifugation for 1 minute at 12,000×g and washed 3× in Wash Buffer (0.1% SDS, 0.5% NP-40, 0.2% sodium deoxycholate, 10 mM PMSF, 10 mM Tris-HCl, pH 8.5, 0.15M NaCl).

The $^{125}$I-labeled proteins bound to the solid phase antibodies were released and denatured by adding 60 µl of 2× Laemmli sample buffer and heating for 3 minutes at 95° C.

The immunoprecipitated $^{125}$I-labeled sporozoite proteins were separated by SDS-polyacrylamide gel electrophoresis in a 12.5% gel and visualized by autoradiography.

Figure 5:
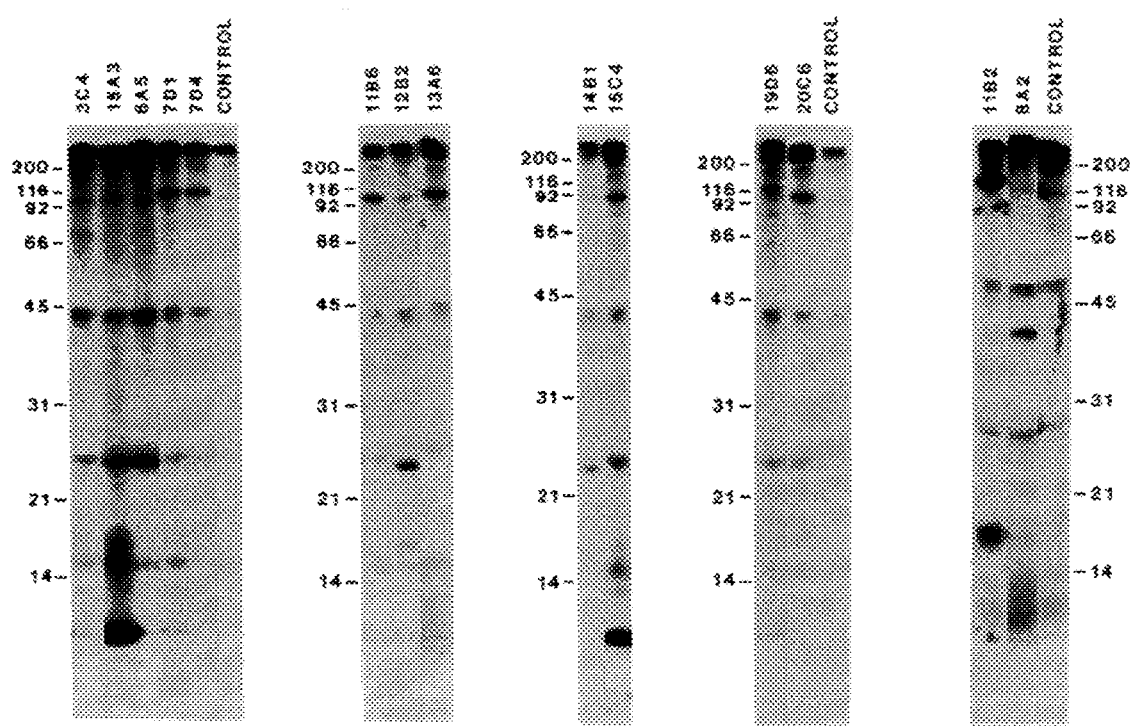

The results of the immunoprecipitation assay with the immune mouse serum are shown in FIG. 4, right panel. Of the hybridoma antibodies that were positive by sporozoite ELISA, 74 were positive by immunoprecipitation assay. As shown in FIG. 5, the hybridoma antibodies fell into two categories, those which precipitated only single proteins (e.g., 3C4, 6A5, 7D4, 8A2, 11D2 and 20C6), and those which precipitated two or more proteins (e.g., 12B2, 15A3, 15C4 and 19D6).

6.1.7. Immunofluorescence Assys with Purified Sporozoites

Sporozoites ($1\times10^5$) were added to 8-chambered slides (Lab Tek) in PBS, pH 7.0, and air dried at 37° C. for 12 hours. The slides were blocked with 10% normal goat serum for 2 hours at 37° C. Diluted antiserum or hybridoma supernatant were added to each chamber and incubated for 2 hours at room temperature. The slides were washed, and a rhodamine-conjugated anti-mouse antibody (diluted in PBS, pH 7.0, 0.3% Triton X-100) was added for 1 hour at room temperature. After washing the slides, the bound antibody was visualized by fluorescence.

Most of the antibodies showed specific immunofluorescence either to the surface membrane and/or to the refractile body of air-dried sporozoites (FIG. 6, panels A and B). Some antibodies intensely stained the apical tip of the sporozoite and only lightly stained the remaining sporozoite surface (FIG. 6, panel C). A representation of the air-dried purified sporozoites can be seen in FIG. 6, left hand slides of panels A, B, C and D. The purified sporozoites were intact and elongated and showed the prominant large posterior refractile body (PRB) and the smaller anterior refractile body (ARB). The apical end (A) of the sporozoite was opposite the posterior refractile body. There was also slight contamination of the preparations by intact sporocysts (panel B, left slide) and broken sporocyst membranes.

6.1.8. Summary of Elisa, Western Blot, Immunoprecipitation and Immunofluorescence Results A summary of results from the above analyses of 55 monoclonal antibodies is shown in Table 2.

TABLE 2

SUMMARY OF MONOCLONAL ANTIBODY ANALYSES

| | WESTERN BLOT | | | | |
|---|---|---|---|---|---|
| Antibody | E. tenella Spz.[a] | Low Spz.[b] | E. acervulina Spz.[c] | E. tenella Mz.[d] | IFA[e] | Immuno-ppt.[f] |
| 3C4 | M[1] | | | | — | 60–80 |
| 11B6 | M[1] | + | + | + | 1,2,4 | 105 |
| 12A5 | M[1] | − | − | − | 1 | — |
| 14D4 | M[1] | + | + | + | 1,3,4 | 66 |
| 15B6 | M[1] | | | | 1,4,7 | 20–24 |
| 17A5 | M[1] | + | + | + | 1 | 150/83 |
| 18B6 | M[1] | + | + | + | — | 25/20, 66/60 |
| 19C6 | M[1] | + | + | + | 1,2 | 25/20 |
| 20A2 | M[1] | + | + | + | 5 | 66/60 |
| 20B4 | M[1] | + | + | + | 1,4 | 86/60 |
| 11C4 | M[2] | | + | − | 1,6 | — |
| 12A3 | M[2] | − | − | − | 1,4,7 | 22/24 |
| 13A6 | M[2] | + | + | | 1,5 | 110 |
| 14B6 | M[2] | | | | 1,4,7 | 105–120 |
| 14D1 | M[2] | | | | — | 120 |
| 9B2 | M[3] | + | + | + | 5 | 66/45 |
| 12B1 | M[3] | + | − | − | 6 | 26–28 |
| 14C6 | M[3] | − | − | − | | 105 |
| 15C4 | M[3] | + | − | − | 6 | 105 |

TABLE 2-continued

SUMMARY OF MONOCLONAL ANTIBODY ANALYSES

| | WESTERN BLOT | | | | |
|---|---|---|---|---|---|
| Antibody | E. tenella Spz.[a] | Low Spz.[b] | E. acervulina Spz.[c] | E. tenella Mz.[d] | IFA[e] | Immuno-ppt.[f] |
| 16D2 | M[3] | | | | — | 60–80 |
| 20C3 | M[3] | + | + | + | 3 | 14–17 |
| 3A5 | 120 | + | + | + | 3 | — |
| 6A4 | 120 | | | | — | — |
| 7D1 | 120 | | + | + | 1,2,4 | 110 |
| 7D4 | 120 | | + | + | 5,1 | 110 |
| 10A6 | 120 | + | − | − | 1,2,6 | 105 |
| 11D2 | 120 | − | − | − | 4,1,2 | 105 |
| 14A1 | 120 | − | − | − | 6,1 | 110 |
| 17B6 | 120 | − | − | − | 1,6,7 | 120 |
| 17C6 | 120 | | | − | 8,1 | 105 |
| 19D6 | 120 | + | − | − | 3 | 120 |
| 20C6 | 120 | + | + | + | 1,2 | 110 |
| 10A5 | >150 | | − | − | 7,5 | 105 |
| 11A6 | >150 | − | − | − | 3 | — |
| 7B2 | >200 | + | | | — | >200 |
| 11B1 | >150,200 | − | − | − | 1,7,6 | 27 |
| 11D4 | 120/24 | + | − | − | 1 | 27 |
| 11D6 | 120/24 | + | − | − | 2 | — |
| 12C3 | 120/24 | + | − | − | 1,8,2 | 25 |
| 15B2 | 120/24 | + | + | + | 3 | — |
| 15A3 | 90/10–14 | + | − | − | 1,6 | 28/14–17 |
| 14C3 | 60 | − | − | − | 1,4 | 6 |
| 14A5 | 120/6 | − | − | − | 1,3,6 | 6 |
| 8A2 | 37 | + | + | − | 1,4 | 37 |
| 6A5 | 28, 10–14 | + | − | − | 1,6 | 25–28 |
| 11A1 | 24 | + | − | − | 1,6 | — |
| 11C1 | 24 | + | − | − | | — |
| 12B2 | 24 | + | − | − | 1,5 | 24/120 |
| 12C6 | 24 | + | − | − | — | — |
| 16B1 | 24 | + | − | − | 1,4 | 6/14–17 |
| 18D5 | 24 | + | − | − | 1,6 | 48/25/6 |
| 20C4 | 24 | | | | 1,3 | 5/14–7 |
| 14B1 | <6 | + | − | − | 1,6 | 20–24 |
| 10A2 | — | − | | | 1,2,4 | 6/105 |
| 5B6 | — | | | | 1,6 | 6/17/15 |

[a]Values shown are the molecular weights of E. tenella sporozoite (Spz.) proteins recognized by the antibodies in Western blots or groups of recognized proteins having molecular weights of 40–150 kd (M[1]), 120 and 80–150 kd (M[2]) and 25 and 40–150 kd (M[3]).
[b]Western blot assays, were performed with 1/5 the usual amount of E. tenella sporozoite (Spz.) protein. Antibodies showing a positive (+) reaction are thus of higher affinity.
[c]Western blot reactivity is shown against E. acervulina sporozoite (Spz.) proteins.
[d]Western blot reactivity is shown against E. tenella marozoite (Mz.) proteins.
[e]Immunofluorescence assay (IFA) staining pattern results are summarized for indirect assay of air-dried E. tenella sporozoites as (1) surface, (2) tip, (3) patchy surface, (4) bright surface, (5) light surface, (6) diffuse surface, (7) refractile body and (8) punctate staining.
[f]Molecular weights of $^{125}$I-labeled E. tenella sporozoite proteins captured by the antibodies in immunoprecipitation (Immunoppt.) assays are shown.

Monoclonal antibodies 7D4, 7D1, 20C6, 8A2, 6A5 and 7B2, which are preferred, have been deposited with the American Type Culture Collection under the provisions of the Budapest Treaty and assigned accession Nos. HB 9707, HB 9708, HB 9709, HB 9710, HB 9711 and HB 9712, respectively.

6.1.9. In Vitro Infection Assays

Primary chicken kidney epithelial cells were established according to the method of Doran et al., J. Protozool. 25:544 (1978) and grown to 40–50% confluency in 4-chambered Lab-Tek slides. MDBK (Madin-Darby bovine kidney) cells (ATTC-CCL 22) were also used in place of the chicken kidney epithelial cells.

The cells were inoculated with 50,000 or 200,000 purified sporozoites. At 16 hours post-infection, the cell monolayers were washed several times to remove any sporozoites which had not penetrated the cells. Representative inoculated cell cultures were fixed in 100% methanol (room temperature for 5 minutes) at 3, 16, 24, 48, 64, 96 and 120 hours post-infection Fixed slides were stored in 1% BSA in PBS, pH 7.0, at 4° C. until processed for immunofluorescence as described above. Staining patterns obtained with various antibodies are shown in FIG. 7.

Between 3 and 24 hours after infection, the fixed cultures revealed intracellular sporozoites (FIG. 7, 7D4 at 3 hours and 8A2 at 19 hours). At later times, the sporozoites degenerated to refractile bodies only (7D4, 60 hrs). The surface and apical tip of the intracellular sporozoites stained brightly with antibody 7D4 (FIG. 7, 7D4 at 3 hours), but this antibody did not stain the surface of the infected cells.

After 24 hours, the sporozoites began to degenerate and develop into schizonts that matured during the following 48 hours. Antibody 7D4 continued to react with the degenerating sporozoites but did not react with the immature schizonts (FIG. 7, 7D4, 60 hrs). As the schizonts matured, however, 7D4 began to react with structures within the schizonts (FIG. 7, 7D4, 100 hrs). These structures were the developing merozoites, and antibody 7D4 continued to react with a surface antigen of the mature and released merozoites (FIG. 7, 7D4, 120 hrs).

Thus, 7D4 identified a 120 kd membrane antigen which was present on *E. tenella* sporozoites and merozoites. This antigen was not expressed during the schizont stage of parasite development until immature merozoites developed within the schizonts.

Antibody 14B1 showed a pattern of reactivity similar to that of antibody 7D4, staining the surface and tip of the intracellular sporozoites (FIG. 8, 14B1, 16 hrs) and showing diffuse staining of the cytoplasm in the immediate vicinity of the intracellular sporozoite. The antigen recognized by 14B1 is present on the apical tip of the immature merozoite within the mature schizont (FIG. 8, 14B1, 100 hrs) and the apical tip of the mature released merozoites (FIG. 8, 14B1, 120 hrs). The staining patterns exhibited by antibodies 7D4 and 14B1 are similar, but the proteins these antibodies recognize have very different molecular weights of about 120 and 6 kd, respectively.

Although antibodies 7D4 and 14B1 reacted with most stages of parasite development, other antibodies reacted only with surface antigens (FIG. 7, 15A3) or with the refractile body (FIG. 7, 7A2) of intracellular sporozoites and not with the schizont or merozoite stages of the parasite.

Two unique antibodies, 8A2 and 19D6, were identified by the infection assay. Antibody 8A2 reacted with a 37 kd protein present on the surface of sporozoites (FIG. 7C, 8A2, 19 hrs), in all stages of the developing schizont (FIG. 7C, 8A2, 120 hrs) and on the surface of released merozoites (FIG. 7C, 8A2, 120 hrs). Unlike the proteins recognized by antibodies 7D4 and 14B1, the 37 kd protein was synthesized throughout the intracellular development of the parasite.

Antibody 19D6 reacted not only with a 180 kd sporozoite surface protein but also with a protein in the cytoplasm of the sporozoite-infected cells (FIG. 8, 19D6 at 3 hours). The cytoplasmic protein recognized by antibody 19D6 might have been shed by the sporozoite after cell infection, since the protein disappeared during immature schizont development and reappeared in the mature schizont and in the released merozoites (FIG. 8B, 19D6, 120 hrs).

Serum antibodies from chickens which have survived an *E. tenella* infection stain the apical tip and surface of intracellular sporozoites (FIG. 8B, Immune Chick Sera, 3 hrs) in a pattern similar to the staining pattern of antibody 7D4, but not the refractile bodies of the intracellular sporozoite.

The immunofluorescence studies with sporozoite-infected chicken kidney cells identified antigens which were (a) specific to the sporozoite (e.g., the greater than 200 and 28 kd proteins recognized by antibodies 7B2 and 6A5, respectively), (b) found in all stages of the intracellular parasite (e.g., the 37 kd protein recognized by 8A2) and (c) specific to sporozoites and merozoites but not to the schizont (e.g., the 120 and 6 kd proteins recognized by antibodies 7D4 and 14B1, respectively).

6.1.10. In Vitro Sporozoite Neutralization Assays

In a modification of the method of Schmatz et al., J. Protozool. 33:109 (1986), MDBK cells were trypsinized and suspended in Minimal Essential Medium (Gibco) supplemented with 1% FBS at a density of $7.5 \times 10^4$ cells/ml. To each well of a microtiter plate (tissue culture treated 96-well), $1.5 \times 10^4$ cells were added and incubated for 48 hours at 40° C. Purified sporozoites were either pretreated with antibody for 1 hour at 40° C. or left untreated prior to infecting the cell monolayers. The antibodies (either tissue culture supernatants, ascites fluid or antiserum) were extensively dialyzed against PBS, pH 7.0, heat inactivated at 56° C. for 30 minutes and sterile filtered before use.

Immediately after infection, [5,6]-$^3$H-uracil was added to all wells to give a final level of 5 µCi/ml. At 19 hours post-infection, the medium was removed and the cultures were washed once with FBS. The cells are released with trypsin-EDTA for 15 minutes at 40° C. and harvested onto glass fiber filters. The filters were dried, placed in scintillation fluid (READY-SOLV®, New England Nuclear) and counted for bound radioactivity. The ability of the antibodies to inhibit sporozoite penetration and/or development was determined by the radioactivity incorporated into cells infected with untreated sporozoites, compared to cells infected with antibody-treated sporozoites.

Sporozoites were also preincubated with control antibodies, buffer or lasalocid, a coccidiostatic drug. Lasalocid completely blocks sporozoite development within the MDBK cells and greatly reduces the incorporation of $^3$H-uracil.

Figure 9:
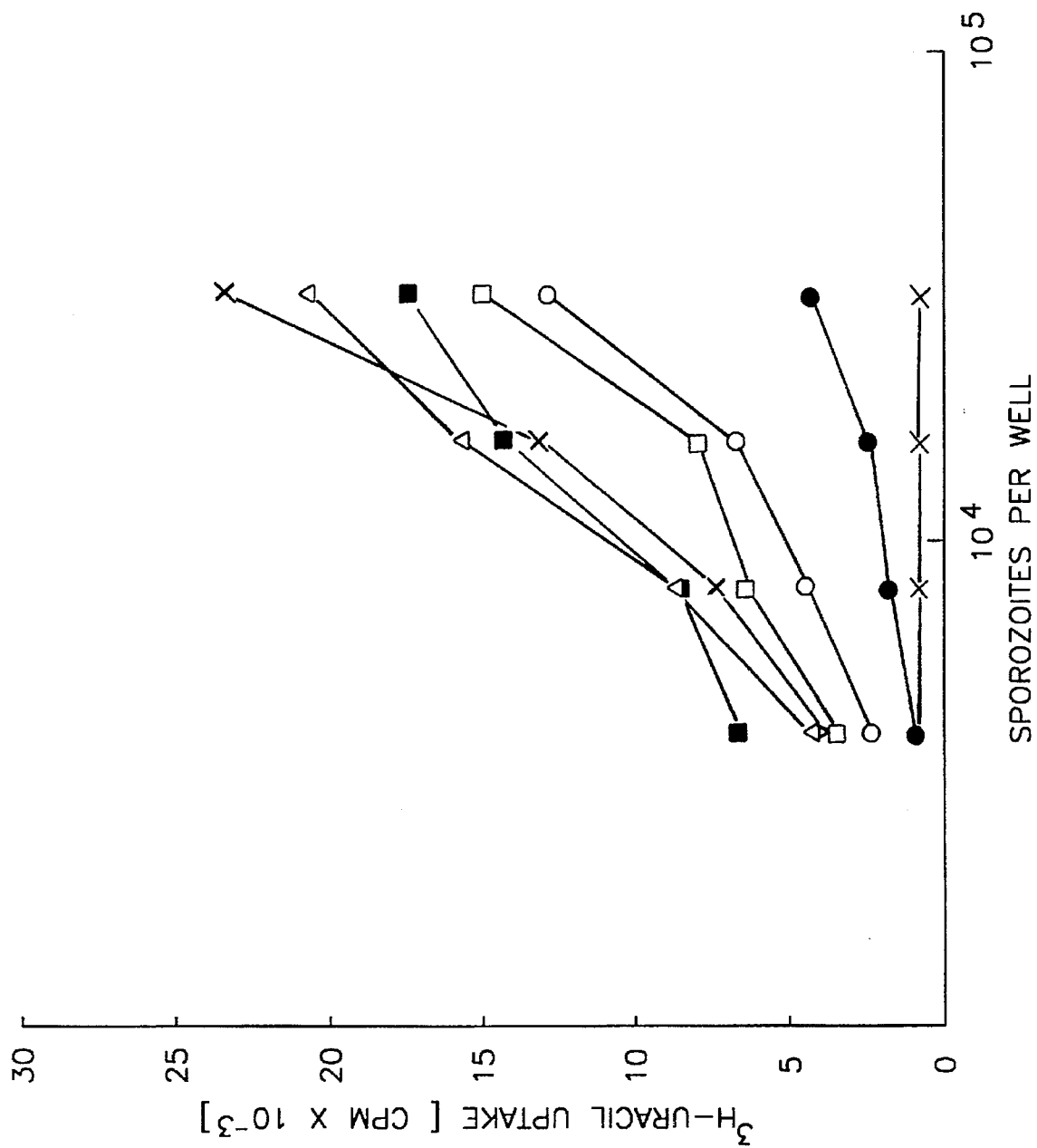

The results are shown in FIG. 9, where it can be seen that antibodies 7D4 (□), 8A2 (○) and 14B1 (●) significantly inhibited $^3$H-uridine incorporation into the infected MDBK cultures. Antibody 6A5 (■) was less effective but showed some inhibition. Treatment with buffer (Δ) and control antibody (X) produced no inhibition, while lasalocid (*) produced essentially complete inhibition.

6.2. Construction of cDNA Expression Libraries 6.2.1. Preparation of Sporulating Oocysts Ceca were removed from 3-week-old chicks (Hubbard Cross: Avian Services, Frenchtown, N.J.) 7 days after oral inoculation with 50,000*E. tenella* (New Hampshire Strain: kindly supplied by Dr. R. Strout, University of New Hampshire) sporulated oocysts/bird and ground in a Waring blender with distilled water for 1 minute. The volume was adjusted to 1 liter with distilled water, and Pepsin (Sigma Chemical Co., St. Louis, Mo.) was added to 3 g/l. The pH was adjusted to 2.0 with concentrated HCl, and the mixture was incubated and stirred for 2 to 3 hours at 39° C., or until a single oocyst suspension was observed. After digestion, the pH was adjusted to 8.0 with 10N NaOH, and 3 liters of distilled water were added. The mixture was allowed to settle overnight. The supernatant was then removed and the sediment was washed with water until the supernatant was clear. The oocysts were sporulated by bubbling air through the suspension in distilled water at room temperature. Sporulation was stopped after 24 hours for RNA preparation.

6.2.2. Isolation of Sporulating Oocyst mRNA

Total RNA was prepared by a modification of the guanidinium/cesium chloride method described by Maniatis et al., supra, page 196. The oocysts were washed with PBS (0.15M NaCl, 20 mM sodium phosphate, pH 7.9) and resuspended by gentle vortex mixing in 10 ml of a solution containing 5M guanidinium isothiocyanante, 50 mM Tris-HCl, 10 mM ethylenediaminetetraacetic acid (EDTA), 0.5% Sarkosyl (sodium N-lauroyl sarcosine, Sigma Chemical Co.) and 0.1M β-mercaptoethanol, pH 7.4, with 5 μl of Antifoam A (Union Carbide. Danbury, Conn.) or another antifoaming agent preferably added. The cell suspension was homogenized until good oocyst breakage was observed microscopically.

Insoluble cellular debris was removed by low speed centrifugation, and the homogenate was divided into 4 aliquots and layered onto 1.2 ml of 5.7M CsCl, 0.1M EDTA, pH 7.5, in 12-ml polycarbonate tubes. The tubes were centrifuged at 40,000 rpm in a Beckman SW 50.1 rotor for 17 hours at 15° C. The supernatant fluid was discarded, the walls of the tubes were dried, and the pellets were resuspended in 1.25 ml of 10 mM Tris-HCl, 1 mM EDTA, 1% sodium dodecyl sulfate (SDS), pH 7.5, with 200 μg/ml of Proteinase K (Boehringer-Mannheim). After incubation at 37° C. for 30 minutes, the solution was extracted 3 times with phenol. The RNA in the final aqueous phase was precipitated 3 times with ethanol and then dissolved in 1 ml of water.

Polyadenylated [poly(A)$^+$] RNA was prepared by twice passing about 2 mg of total RNA over an oligo(dT)-cellulose column (Pharmacia Fine Chemicals) as described by Maniatis et al., supra, page 197. The poly(A)$^+$ RNA was precipitated twice with ethanol and dissolved in 200 μl of water. The yield was about 26 μg, as calculated from the optical density at 260 nm.

6.2.3. Preparation of Merozoites

Merozoites of *E. tenella* were harvested from the ceca of 50 infected chickens (3 week old Hubbard Cross; Avian Services, Frenchtown, N.J.) 5 days after infection with 50,000 of the above sporulated oocysts/bird. The ceca were removed and washed with phosphate buffered saline (PBS) for 15 minutes on a magnetic stirrer. The epithelial debris was partially removed by low speed centrifugation (50×g), and the crude merozoites were recovered by centrifugation at 2,000×g at 4° C. for 10 minutes. The pellet was resuspended in Lysing Buffer (8.29 g/1NH$_4$Cl, 0.372 g/1 Na$_2$EDTA, 1.0 g/1KCO$_3$, pH 7.6) and incubated on ice for 30 minutes. The merozoites were collected by centrifugation, washed once in PBS and passed over a column containing 1.0 g of spun nylon fiber (Scrub Nylon Fiber, Fenwall Laboratories, Deerfield, Ill.) in a separatory funnel. The merozoites were collected by centrifugation as before and frozen on dry ice for RNA isolation, or further purified in diethylaminoethyl cellulose (DEAE, Whatman DE52) for Western blot analysis.

For purification in DEAE cellulose, approximately 1×10$^9$ merozoites were applied in PBS to a 10-ml bed volume column and eluted with PBS. The merozoites were recovered in the first 100 ml of flow-through, essentially free of red blood cells and other cellular debris.

6.2.4. Isolation of Merozoite mRNA

Frozen merozoite pellets containing 1×10$^9$ to 1×10$^{10}$ organisms were thawed into 10 ml of TEL/SDS buffer (0.2M Tris HCl, 0.1M LiCl, 25 mM EDTA, 1% (w/v) sodium dodecyl sulfate (SDS), pH 8.8) containing 1 mM dithiothreitol (DTT) and 300 units of RNasin (Promega Biotec, Madison, Wis.) and homogenized with 10–12 strokes in a teflon-coated tissue homogenizer. Insoluble debris was separated by centrifugation in the cold at 3,000×g. The supernatant fluid was extracted twice with phenol:chloroform:isoamyl alcohol (24:24:1,v/v) which had been equilibrated with the TEL buffer.

The aqueous phase was digested with 100 μg/ml proteinase K at 37° C. for 30 minutes and reextracted with an equal volume of phenol:chloroform (1:1), and the nucleic acid was precipitated with two volumes of ethanol for 1 hour on dry ice, or overnight at −20° C. The pellet, after centrifugation at 10,000×g for one hour, was resuspended in TE (10 mM Tris, pH 7.5, 2 mM EDTA) and spun through a 4 ml CsCl cushion (5.7M CsCl, 0.1M EDTA) at 150,000×g for 20 hours at 15° C. The RNA pellet was reprecipitated from 0.2M potassium acetate with 2.5 volumes of ethanol. This total RNA was passed once over oligo-dT cellulose to enrich for poly(A)$^+$ RNA, as described by Maniatis, supra, page 197. A typical yield of 1.9 mg of total RNA from 5×10$^9$ merozoites contained approximately 20 μg of poly(A)$^+$ RNA.

6.2.5. Synthesis of Oocyst and Merozoite CDNAs, and Insertion Into Phahe Vectors Double-stranded cDNA was synthesized from 6 μg of the sporulating oocyst poly (A)$^+$ENA as described by Gubler et al., Gene 25:263 (1983), using reverse transcriptase (BRL) to elongate from an oligo(dT) primer and RNase H (BEL) and *E. coli* DNA polymerase I (New England Biolabs) to synthesize the complementary strand. The double-stranded cDNA was then blunt-ended with T4 DNA polymerase (BRL), and Eco RI linkers (GGAATTCC, Collaborative Research) were added after treatment with EcoRI methylase (New England Biolabs), following the manufacturers' protocols.

After digesting the thus prepared cDNA with EcoRI, a library was prepared in λgt11 (Stratagene Cloning Systems, San Diego, Calif.) as described by Huynh et al., in D. Glover (ed.), DNA Cloning Vol. I: A Practical Approach, 1985, IRL Press, Washington, D.C., pp. 49–78. The EcoRI cDNA fragments were ligated to EcoRI digested, dephosphorylated λgt11 arms (Stratagene Cloning Systems), and the resulting DNA was packaged into phage with the Gigapack® kit (Stratagene Cloning Systems), following the manufacturer's protocol.

The resulting library was amplified by plating on Y1088 host cells (ATCC No. 37195). The percentage of recombinants was estimated from the ratio of blue to colorless plaques on X-gal plates (Maniatis, supra, page 24) in the presence of isopropyl thiogalactoside (IPTG, Sigma Chemical Co.) to be about 90%.

Double-stranded cDNA copies of the merozoite poly(A)$^+$RNA were synthesized essentially as described above. The double-stranded cDNA used in the construction of the library contained from about 200 to 4,500 base pairs (bp), as judged by migration in denaturing gels [Bailey et al., Anal. Biochem. 70:75 (1976)].

The merozoite cDNA was methylated and ligated to EcoRI linkers as described above, except that CCGAATTCGG linkers (Collaborative Research) were used. Following digestion with EcoRI, the cDNAs were fractionated in Biogel A-50M to remove excess linker molecules and cDNAs smaller than approximately 300 bp, as described by Huynh et al., supra.

The cDNAs were ligated to λgt11 arms, and the DNA was packaged into phage as described above. The resulting library, which contained about 50,000 phage, was amplified by plating on Y1088 host cells. Plaque analysis on X-gal plates in the presence of IPTG showed about 90% recombinants.

6.3. Immunological Screening of cDNA Libraries

The λgt11 merozoite cDNA expression library was plated on Y1090 cells (ATCC No. 37197) at a density of about 10,000 plaques per 150 mm plate. Six such plates were incubated for 3.5 hours at 42° C., overlayered with nitrocellulose filters previously soaked in 10 mM IPTG to induce the expression of the β-galactosidase fusion protein, and incubated for an additional 4–5 hours to overnight at 37° C. The filters were removed from the plates and subjected to several batchwise washes with TBS (20 mM Tris, pH 8.0, 0.15M NaCl). Non-specific protein binding sites were blocked by incubation in 20% fetal calf serum (FCS) in TBS for 2–4 hours on a rotary shaker, at 4° C.

Ascites fluid for nine monoclonal antibodies known to react with merozoite antigens (designated 7D4, 7D1, 20C6, 13A6, 20C1, 11B6, 3A5, 13A1 and 15B2) was pooled, adjusted to 20% FCS and 0.15M NaCl in a final volume of 100 ml and applied to each of the filters in petri dishes, two filters per dish. The filters were incubated with the primary monoclonal antibody pool at 4° C. overnight on a rotary shaker. Unbound antibody was removed by washing the filters 5–6 times with TBS at room temperature. Bound antibody was detected by incubating the filters with goat anti-mouse horseradish peroxidase (HPOD) conjugate (Boehringer-Mannheim), followed by color development using 3 mg/ml 4-chloro-1-naphthol (Bio Rad) and 0.018% $H_2O_2$, as described by Hawkes et al., Anal. Biochem. 119:142 (1982).

Positive plaques identified in the initial high density screen were plaque-purified in a secondary screen using the same monoclonal antibody pool. Each positive was assigned to an individual monoclonal from the pool by plating the positives in multiple grid arrays, each of which was induced with IPTG, transferred to nitrocellulose and incubated with one of the monoclonals from the pool. One positive phage designated λm2-4 was identified which was recognized by three of the eight antibodies in the pool, antibodies 7D1, 7D4 and 20C6.

Similar methods were used to screen the sporulating oocyst cDNA library, except that a pool of monoclonal antibodies containing antibodies 6A5, 7B2, 15A3 and 20C6 was used for the initial screening; 7B2, 15A3, 20C6 and 8A2 were used in a second screening; and 15A3, 7B2 and 20C6 were used in a third screening: and the incubation buffer contained in addition 0.05% Tween-20 [polyoxyethylene (20) sorbitan monolaurate]. In this way, plaques designated λS1-3, λS1-4 and λS1-7; λS2-1, λS2-4 and λS2-5; and λS3-1 which were recognized by monoclonal antibodies 6A5, 8A2 and 7B2, respectively, were identified in the oocyst cDNA library. DNA made from the phage producing protein that reacted with the 6A5 antibody was analyzed by digestion with EcoRI and electrophoresis in agarose gels (Maniatis et al., supra, page 150). Three different inserts having sizes of approximately 1150, 890 and 615 bp were thus found.

6.4. Expression of Eimeria Genes In *E. Coli*

The 1.1 kb and 0.9 kb EcoRI DNA molecules from phages λS1-7 and λS1-3, respectively, were isolated and inserted into the EcoRI site of each of three variable reading frame expression vectors, pEV-vrf1, pEV-vrf2 and pEV-vrf3, constructed as described by Crowl et al., Gene 38:31 (1985). Plasmids containing the inserts in both possible orientations were transformed as described by Mandel et al. [J. Mol. Biol. 53:159 (1970)] into *E. coli* strain MC1061 carrying the compatible plasmid pRK248cIts described by Bernard et al. [Methods in Enzymology 68:482 (1979)]. Strain MC1061 and plasmid pRK248cIts have been deposited with the American Type culture Collection and assigned accession Nos. ATCC 33766 and 53238, respectively.

The bacterial transformants were grown at 30° C. in M9 medium [Maniatis et al., supra, page 68] with 0.5% glucose and 0.5% Casamino acids and shifted to 42° C. at an O.D. (550 mµ) of 0.5 as described by Crowl et al., supra, to induce transcription at the $\lambda P_L$ promoter. After incubating for 2–3 hours, 1-ml samples were taken, and the cells in the samples were collected by centrifugation. The cell pellets were treated as described by Crowl et al., supra, and the lysates were subjected to sodium dodecyl sulfate (SDS) polyacrylamide gel electrophoresis as described by Laemmli, Nature 227:680 (1970). Following electrophoresis, the proteins in the gels were either stained with Coomassie brilliant blue or transferred to nitrocellulose membranes for Western blot analysis [Towbin et al., Proc. Natl. Acad. Sci. USA 76:4350 (1979); Burnetti, Anal. Biochem. 112:195 (1981)], using the 6A5 monoclonal antibody and goat anti-mouse HPOD conjugate for detection.

This analysis showed that the 0.9 kb cDNA molecule in one orientation in vector pEV-vrf1 produced a 20 kd protein that reacted with the 6A5 antibody. No expression was observed with the 1.1 kb molecule, probably because it contained 5′ noncoding sequences. To optimize the yield of this protein, various expression media were examined. It was found that the preferred medium contained per liter (±10%) 6.0 g $KH_2PO_4$, 4.0 g $K_2HPO_4$, 5.0 g $(NH_4)_2SO_4$, 3.5 g $MgSO_4$-$7H_2O$, 21.0 g Yeast Extract, 3.5 g Bacto Tryptone, 1.0 ml LB625 Antifoam, 25 g glucose, 70 mg Thiamine-HCl, 2.5 ml vitamin solution [GIBCO MEM (100X) Vitamin Solution] and 1.0 ml trace elements. LB625 Antifoam, a product of Union Carbide, is a linear polymer of ethylene and polypropylene oxide having a viscosity of 625 Saybolt Universal Seconds at 37.8° C.

Vitamins per liter of fermentation broth included 0.25 mg each of D-Ca pantothenate, choline chloride, folic acid, nicotinimide, pyridoxal-HCl and additional thiamine-HCl; 0.50 mg of i-inositol; and 0.025 mg of riboflavin. Trace elements per liter of broth included 2.7 mg of $FeCl_3$-$6H_2O$; 0.8 mg each of $ZnSO_4$-$7H_2O$ and $CuSO_4$-$5H_2O$; 0.7 mg each of $CoCl_2$-$6H_2O$ and $Na_2MoO_4$-$2H_2O$; 0.2 mg of $H_3BO_3$; and 0.5 mg of $MnSO_4$-$H_2O$.

The nature of the immunoreactive protein expressed by phage λm2-4 was investigated first in a lysogen isolated from an infection of Y1090 cells by differential growth at the permissive (30° C.) and non-permissive (42° C.) temperatures. For Western blot analysis of the proteins synthesized by this lysogen, a 50 ml culture was grown at 30° C. in LB medium [Maniatis et al., supra, page 69] to an O.D. (550 mµ) of 0.5, and shifted to 42° C. to induce replication of the phage. After 15 minutes at 42° C., IPTG was added to 10 mM, and incubation was continued at 37° C. for 30 minutes. The cells were harvested by centrifugation at 4° C. and lysed by boiling for 5 minutes in Laemmli sample buffer (0.125M Tris, pH 6.8, 1% (w/v) SDS, 1.4M β-mercaptoethanol, 001% Bromophenol Blue (w/v), 20% (v/v) glycerol).

The equivalent of 1.0 ml of culture was resolved by electrophoresis in a 12.5% SDS-polyacrylamide gel, transferred electrophoretically to nitrocellulose and probed as described above with a pool of the three monoclonal antibodies (7D1, 7D4 and 20C6) which identified the λm2-4 phage. Development of the Western blot revealed a fusion protein of greater than 150 kd size which was present in the induced lysogen (FIG. 10, panel B, Lane 2). Antibody specific for β-galactosidase also reacted with this high molecular weight protein, and to a protein of approximately 114 kd, the expected size of β-galactosidase alone (see FIG. 10, panel A, lane 2).

The phage λm2-4 DNA was digested with EcoRI to produce a 1.7 kb DNA molecule. This molecule was subcloned into an EcoRI-linearized plasmid pool containing plasmids pEV-VRF1, 2 and 3 [Crowl et al. supra] and transformed into E. coli I strain MC1061 containing plasmid pRK248clts, as described above. Transformants were screened for expression of an immunoreactive protein upon temperature induction, using the pool of three monoclonal antibodies shown to react with the fusion protein in the λm2-4 1 lysogen. The immunoreactive recombinant protein was further characterized by Western blot analysis of the E. coli lysates, employing one of the three monoclonal antibodies, 7D4, from the pool. Each of the positive colonies was found to contain plasmid DNA with the expected 1.7 kb insert, and to direct the synthesis of a protein of approximately 65 kd upon induction, as determined by SDS-polyacrylamide gel electrophoretic analysis.

The expression of this 65 kd protein was found to be relatively insensitive to variations in growth medium and induction protocol. The protein was recovered quantitatively in the supernatant following sonic disruption of the cell pellet.

Figure 11:
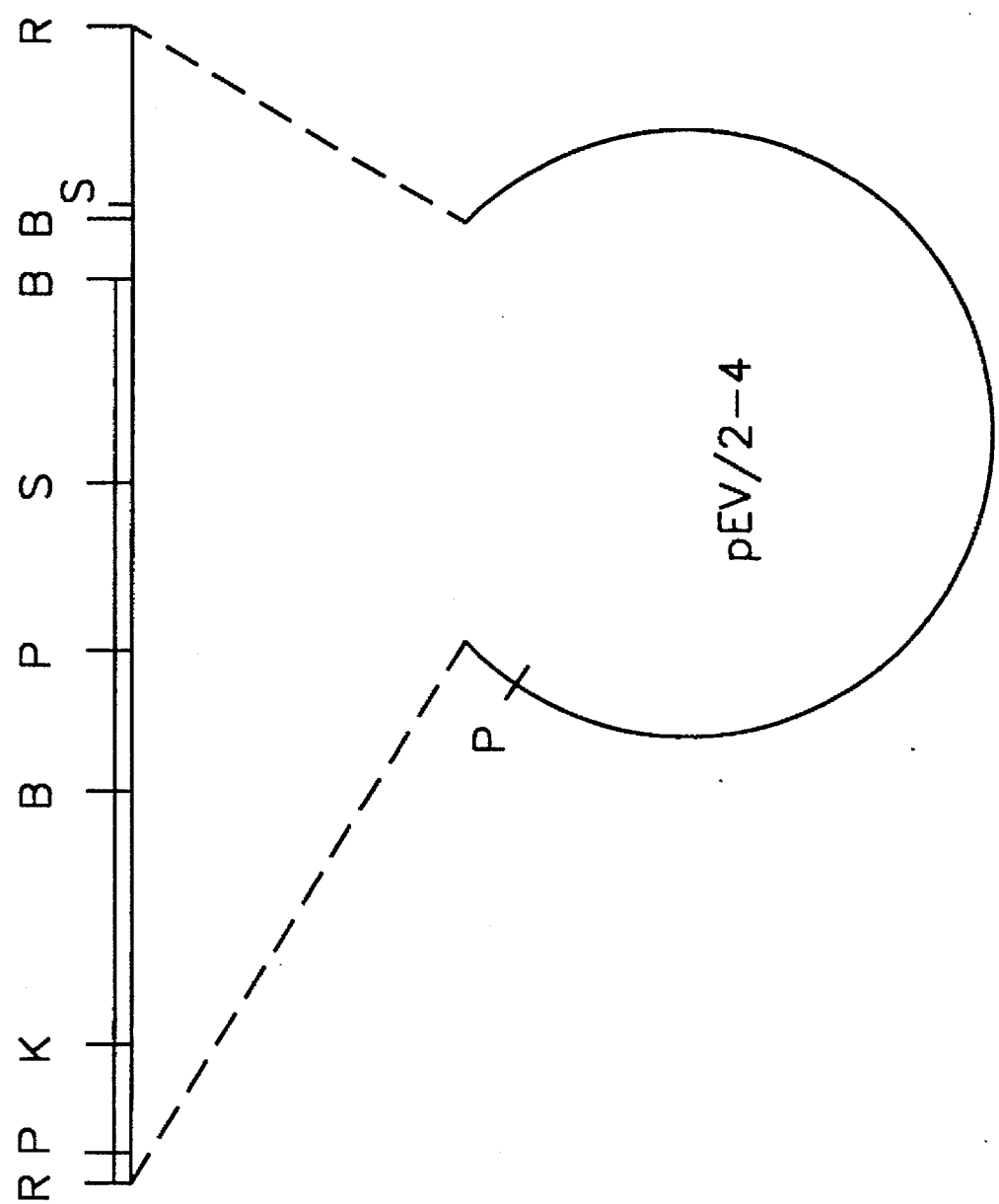
FIG. 11 is a schematic representation of plasmid pEV/2-4, a 65 kd protein expression plasmid containing a 1.7 kb EcoRI DNA insert from phage λm2-4. Positions of various restriction enzyme sites in the insert are shown relative to the EcoRI site, including PstI (P, at bp 53 and 776), KpnI (K, at bp 202), BstNI (B, at bp 584, 1303 and 1412) and Sau3A (S, at bp 1017 and 1439).

The expression plasmid containing the 1.7 kb insert was used in the subsequent production of recombinant protein and is shown schematically in FIG. 11. This plasmid was propagated in MC 1061 host cells lysogenic for λcI857 (prepared using standard methods for the generation of λ phage lysogens described by Arber et al., in Cold Spring Harbor Monograph, Lambda II, 1983, Hendrix et al., Eds., Cold Spring Harbor Laboratories, Cold Spring Harbor, p. 450) at 30° C., to maintain the repressed state of the $P_L$ promoter in the plasmid.

Using similar methods, expression of a 28 kd protein encoded by a sporulating oocyst cDNA segment having about 1.1 kb was carried out. This protein bound specifically to monoclonal antibody 8A2. Expression of a 45 kd protein encoded by a sporulating oocyst cDNA of about 1.2 kb was also carried out. This protein bound specifically to monoclonal antibody 7B2.

6.5. DNA Sequence Analysis

In general, small scale isolation of plasmid DNA from 1 ml of saturated overnight cultures was carried out using the procedure of Birnboim et al. [Nucleic Acids Research 7:1513 (1979)]. This procedure allows the isolation of a small quantity of DNA from a bacterial colony for analytical purposes. Larger amounts of plasmid DNA were prepared using 1-liter cultures following a standard protocol with cesium chloride centrifugation. [Maniatis et al., supra, page 93].

The DNA sequences of the cDNAs from the sporulating oocyst library were determined by the chemical cleavage method of Maxam et al., Methods in Enzymology 65:499 (1980) and by the chain-termination method of Sanger et al., Proc. Natl. Acad. Sci. USA 74:5463 (1977), as modified for double-stranded plasmid DNA by Smith et al., Cell 16:753 (1979) and Wallace et al., Gene 16:21 (1981). In the chain termination protocol, 7-deaza-dGTP [Bart et al., BioTechniques 4:428 (1986)] Was substituted for dGTP to eliminate G-C compression artifacts.

Figure 12:
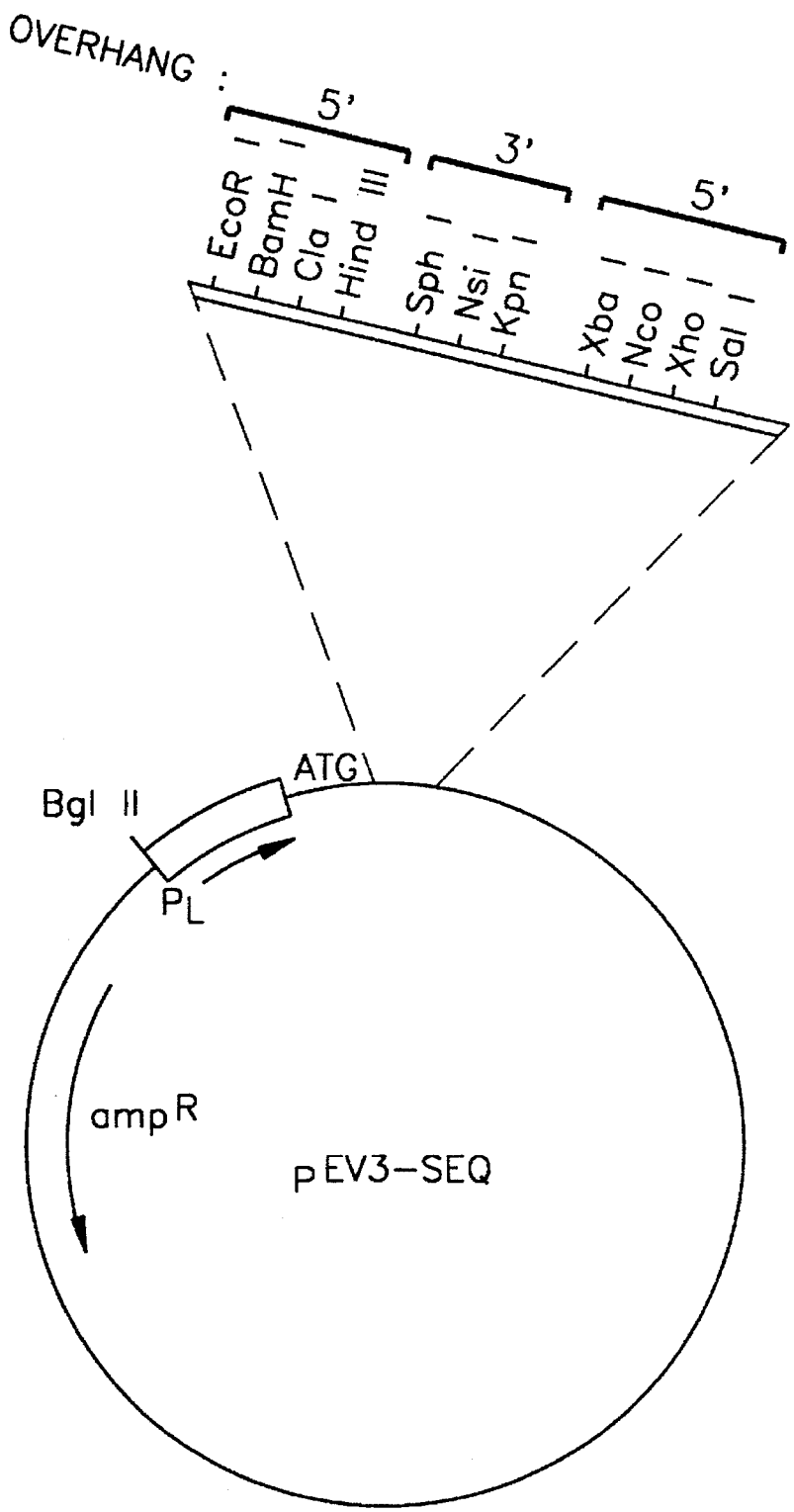
FIG. 12 is a map of pEV3-SEQ, containing a polylinker with the indicated sites inserted between the EcoRI and SalI sites of pEV-vrf3. The synthetic oligonucleotide CGGTCGACTCGAGCCA, indicated by the dashed arrow, was used as a primer for chain-termination DNA sequence analysis.

To facilitate sequence analysis, the 1.1 kb EcoRI molecule from λS1-7 was transferred to plasmid pEV3-SEQ (FIG. 12), which has a polylinker next to the EcoRI site of pEV-vrf3. This polylinker was used to linearize the plasmid at the BamHI and KpnI sites to generate unidirectional deletions with exonuclease III [Henikoff, Gene 28:351 (1984)]. The XbaI site in the polylinker was used for 3'-end labeling for Maxam-Gilbert sequencing of the deletions, and the primer CGGTCGACTCGAGCCA was used for Sanger sequencing. This primer was $^{32}$P labeled at its 5' end using [λ-$^{32}$P]ATP (ICN) and polynucleotide kinase as described by Maniatis et al., supra, page 122.

FIG. 13 shows the restriction sites in the 1.1 kb EcoRI molecule used for Maxam-Gilbert sequencing. The position of the EcoRI sites in the 0.9 kb molecule are also shown, since these were also used. The end points of deletions made with exoIII are also shown. These were sequenced either from the XbaI site in the pEV3-SEQ polylinker by the Maxam-Gilbert method or with a primer extension (FIG. 12) by the Sanger method. Both stands of the entire cDNA were sequenced by one or both of these methods. Due to a high G-C content in the DNA, the Maxam-Gilbert reactions were usually fractionated in both 8% and 15% polyacrylamide-urea gels.

Primer extension was carried out by incubating 1.5 μg of poly(A)$^+$ RNA with 2 pmoles of the 5'-end labeled synthetic oligonucleotide primer, GAGGTCTGCCATTTTGC, for 60 minutes at 42° C. in 50 mM Tris-HCl, pH 8.0, 8 mM MgSO$_4$, 0.1M NaCl, 2 mM dithiothreitol, 2 mM of each deoxynucleotide triphosphate (dNTP, Pharmacia Fine Chemicals), 20 units RNasin (Promega Biotec, Madison, Wis.) and 20 units AMV reverse transcriptase (Pharmacia, Piscataway, N.J., FPLCpure). The products were analyzed in the 8% polyacrylamide-urea gels used for sequence analysis, with $^{32}$p-labeled HpaII digested pBR322 DNA as a molecular size marker.

For sequence analysis, the primary products were eluted from the gel and analyzed by the chemical cleavage method of Maxam et al., supra, or ddNTPs were used in the extension reaction [Tolan et al., J. Biol. Chem. 259:1127 (1984); Graves et al., J. Biol. Chem. 261:11409 (1986)]. The reactions were analyzed in 8% polyacrylamide-urea gels.

The nucleotide sequence of the 1.1 kb cDNA molecule is shown in FIG. 14. The sequence of the 0.9 kb molecule extends from base 188 to base 1082 within this larger molecule. The amino acid sequence predicted from open reading frame analysis of this nucleotide sequence is shown in FIG. 15. The correctness of the predicted amino acid sequence shown in FIG. 15 was confirmed as follows.

Synthetic polypeptides were prepared having amino acid sequences corresponding to residues 41–54 and 145–164 of FIG. 15. Rabbit antisera raised against both of these polypeptides were used in Western blot analysis of both total sporozoite proteins and a lysate of the E. coli transformant expressing the 0.9 kb cDNA. The antibodies against both of the polypeptides bound to proteins in both of the Western blots.

Using similar methods, the nucleotide sequence of the 1.7 kb insert encoding the 65 kd protein in phage λm2-4 was determined, with the results shown in FIG. 16 and 27. The predicted amino acid sequence of the protein encoded by this DNA sequence is shown in FIG. 17 and 28. This sequence was confirmed by amino acid sequence analysis performed on polypeptides produced by tryptic digestion of the expressed 65 kd protein, as described below. Regions in the overall amino acid sequence corresponding to some of these peptides are underlined in FIG. 17 and 28.

Curiously, the DNA sequence open reading frame for the 1.7 kb molecule would be expected to encode a protein of about 33,349 daltons. Yet, the expression product from this DNA fragment migrates in SDS gels with an apparent molecular weight of about 65 kd. The reason for this discrepancy between the predicted and observed protein size is unknown. This protein is referred to herein as the "65 kd" protein.

In a similar fashion, the nucleotide and predicted amino acid sequences of the cDNA molecule encoding the 28 kd protein recognized by monoclonal antibody 8A2 were determined, with the results shown in FIGS. 18 and 19, respectively.

The cDNA molecule encoding the 28 kD protein recognized by monoclonal antibody 8A2 has been resequenced using the standard sequencing techniques described above. The resulting sequence is provided in FIG. 29 and FIG. 30. The deduced amino acid sequence is provided in FIG. 31. Based on this amino acid sequence, the weight of the protein recognized by 8A2 is probably around 37 kD. The same sequence with the first three amino acids removed is provided in FIG. 32. These three amino acids were probably encoded by linker sequences described above and used in the cloning procedure described, and as such would therefore be artifacts and not part of the protein. Similarly, FIGS. 26, 27, 33, 34 represent sequences from which linker code has been removed.

Similarly, the nucleotide and predicted amino acid sequence of the 1.2 kb 7B2 cDNA were determined. Since a continuous open reading frame was found and the protein isolated from sporozoites by immunoprecipitation is larger than 200 kd, the library was screened for larger cDNAs, using the 1.2 kb cDNA as a probe. A 3.2 kb cDNA was thus obtained, having the nucleotide and predicted amino acid sequences shown in FIGS. 20 and 21, 33 and 34.

6.6. Purification and Characterization of the 65 KD Protein

6.6.1. Protein Purification

High cell density fermentation of *E. coli* MC1061 (pRK248cIts) containing the pEV/2-4 expression plasmid was carried out in 10-liter fermenters in 1.5×M-9 medium, using standard protocols of temperature induction as described above after approximately 4 hours of growth at the permissive temperature. The cell mass was harvested 5 hours after induction, yielding 500 grams of cell paste.

Fifty grams of the *E. coli* cell paste were uniformly suspended in 500 ml of 10 mM Tris-HCl, 5 mM EDTA, pH 8.0, and stirred at 2°–8° C. for two hours. The suspension was passed through a Gaulin homogenizer (APV Gaulin, Everett, Mass.) two to three times at 7,000 psi. The cell lysate was centrifuged at 24,000×g for one hour in a Sorvall RC-5 centrifuge, and the pellet was discarded. Solid ammonium sulfate was added to the supernatant (final concentration 80%). This was kept at 4° C. for two hours, and then centrifuged at 24,000×g for one hour. The pellet was dissolved in 20 mM potassium phosphate, pH 6.8. After centrifugation, the supernatant was dialyzed against 20 mM potassium phosphate, pH 6.8.

A Pharmacia glass column (5 cm diameter×10 cm length) was packed with NuGel P-DE 200® (200 Angstrom, 40–60 µm, weak anion exchange, Separation Industries, Metuchen, N.J.) silica support. The gel was equilibrated with 20 mM potassium phosphate, pH 6.8. The sample was loaded (10 ml/min), washed with equilibration buffer and eluted with 20 mM potassium phosphate containing 0.4M NaCl, pH 6.8. The column fractions were analyzed by Western blotting with antibody 7D4 to detect the 65 kd protein.

An immunoaffinity column was used to further purify the 65kd protein. The adsorbent for this column was prepared by immobilizing monoclonal antibody 7D4 on NuGel P-polyaldehyde® (500 Angstrom, 40–60 µm, Separation Industries, Metuchen N.J.) silica support. The immobilization procedure involved the following: 10 grams of polyaldehyde support were suspended and washed with 0.1M potassium phosphate, 0.1M NaCl, pH 6.8, and transferred quantitatively into an Ehrlenmeyer flask containing 20 ml of monoclonal antibody 7D4 at a protein concentration of 8 mg/ml. Sodium cyanoborohydride (4 mg) was then added to the suspension. The mixture was shaken gently at 4° C. for 16 hours. The gel was filtered and washed with 0.1M potassium phosphate, 0.1M NaCl, pH 6.8. Pooled filtrates were checked for unbound antibody. Binding density was 8 mg/g of support. Uncoupled activated sites were blocked by suspending the gel in 20 ml of 1M ethanolamine, pH 7.5 Sodium cyanoborohydride (4 mg) was added to the suspension, which was then agitated at 4° C. for 16 hours. The gel was collected and washed thoroughly with cold coupling buffer.

To carry out the immunoaffinity chromatography, a column (1 cm×10 cm) was packed with the immobilized 7D4 antibody and equilibrated with cold phosphate buffered saline (PBS) containing 0.1% Triton x-100. A pool of fractions from the NuGel P-DE 200® column containing the 65 kd protein was diluted 2× with PBS containing 0.1% Triton X-100 and loaded onto the column at a flow rate of 10 ml/min. After loading, the gel was washed with PBS to remove unadsorbed material. The adsorbed immunoreactive material was eluted with 0.3M acetic acid, 0.1M NaCl, pH 2.7, buffer. The protein was then concentrated in an Amicon Stircell® apparatus using a YM 10 membrane.

The purity of the protein was determined by SDS polyacrylamide gel electrophoresis as described by Laemmli [Nature 227:680 (1970)]. The gel was stained with Coomassie blue. Western blot analysis was also carried out, using the 7D4 monoclonal antibody with goat anti-mouse horseradish peroxidase conjugate. The results are shown in FIG. 22. Lanes 2, 3, 4 and 5 contain purified protein from preparations. Lanes 1 and 6 contain a mixture of molecular weight marker proteins having the molecular weights shown to the left and right of the figure. Ten micrograms of protein were run in each lane.

In FIG. 22, it can be seen that the purified protein migrated in the SDS gel as a major band having an apparent molecular weight of about 65 kd, with minor bands having higher and lower mobility.

6.6.2. Isoelectric Point Determination

Ten micrograms of the purified 65 kd protein were subjected to isoelectric focusing in a preformed isoelectric focusing gel obtained from LKB Instruments, Gaithersburg, Md. A mixture of standard proteins having known isoelectric points was run at the same time. The gel was run for about 2 hours at 50 mA, 1,500 V according to the manufacturer's instructions, using a 3.5–9.5 pH gradient.

Upon completion of electrofocusing, the gel was stained with Coomassie blue dye to detect the protein bands. The isoelectric point of the purified protein was then determined by measuring the position of the band within the pH gradient in relation to the positions of the protein standards. The isoelectric point of the protein thus determined was 4.6.

6.6.3. Amino Acid Composition Analysis

Amino acid composition analysis was carried out using post column reaction with fluorescamine as described by Pan et al., in Methods of Protein Microcharacterization, 1986, Shively, ed., The Humana Press, pp. 105–119.

Samples containing 3 μg of the 65 kd protein were hydrolyzed in 6N HCl containing 4% thioglycolic acid at 110° C. for 20 to 24 hours in vacuo, and 10% of the hydrolysate was used for analysis. Cysteine values were determined after performic acid oxidation. The results are shown in Table 3.

TABLE 3

AMINO ACID COMPOSITION ANALYSIS OF THE 65 KD PROTEIN

| AMINO ACID | MOLE PERCENT |
| --- | --- |
| Asp | 6.06 |
| Thr | 6.07 |
| Ser | 7.27 |
| Glu | 18.24 |
| Pro | 5.35 |
| Gly | 16.76 |
| Ala | 11.71 |
| Cys | 4.45 |
| Val | 4.88 |
| Met | 2.08 |
| Ile | 2.17 |
| Leu | 3.22 |
| Tyr | 2.20 |
| Phe | 2.13 |
| His | 1.07 |
| Lys | 2.72 |
| Arg | 3.61 |
| Trp | ND |

ND = Not Determined 6.6.4. N- and C-Terminal Sequence Analysis

Two hundred picomoles of the protein (as determined by amino acid composition analysis) were subjected to N-terminal analysis, using the method of Hewick et al.; J. Biol. Chem. 256:7990 (1981) and an Applied Biosystems model 470A sequencer (Applied Biosystems, Inc., Foster City, Calif.). The N-Terminal sequence thus determined was M-N-K-N-S-?-L-G-G-F-?-S-M-Q-E-S-P-P-P-. The identities of the amino acid residues at positions indicated by question marks are uncertain because the recovery of PTH-Cys was low, and cysteine residues might be involved in disulfide linkages [Hewick et al., J. Biol. Chem. 256:7990 (1981)].

C-Terminal analysis was performed on 1200 picomoles of the 65 kd protein by time course carboxypeptidase Y digestion as described by Hayashi, Methods in Enzymology 47:84 (1977). Carboxypeptidase Y (Boehringer Mannheim, Indianapolis, Ind.) was used at a concentration of 0.8 μg/350 μl in 0.05M sodium acetate buffer, pH 5.9, and sample aliquots were taken after 0, 2, 5, 10, 20 and 30 minutes for analysis. The sample aliquots were acidified with HCl to stop further reaction and then subjected to amino acid analysis as described above. This analysis showed that the amino acid sequence at the C-terminus is probably (Met, Trp)-Ala-Ser. Tryptophan was observed to increase simultaneously with the methionine, but Trp is difficult to quantify in the fluorescamine analyzer because it has a low reactivity with fluorescamine. Therefore, the relative positions of Trp and Met could not be determined with certainty by this analysis.

6.6.5. Tryptic Peptide Analysis

In part to verify the amino acid sequence predicted from the nucleotide sequence of the cDNA encoding the 65 kd protein, some of the protein was digested with trypsin (Cooper Biomedical, Philadelphia, Pa.) and the resulting peptides were sequenced as described below.

Figure 23A:
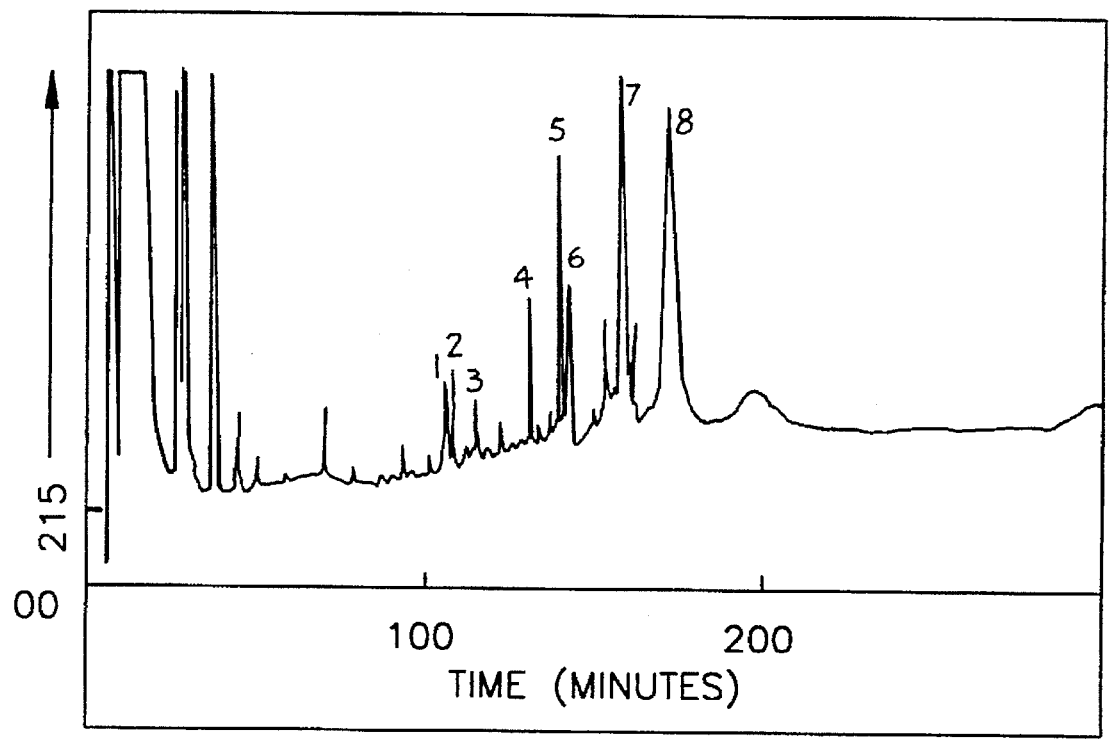

Tryptic digestions were carried out overnight at 37° C. on 148 μg of protein in 0.2M ammonium bicarbonate, pH 8, using an enzyme-to-substrate ratio of 1:30 (weight or molar basis?). Peptides thus generated were separated in a Waters HPLC system using an Altex ultrasphere 250×4.6 mm C-18 column (Beckman Instruments, Fullerton, Calif.) with a 0 to 55% gradient of increasing acetonitrile in 0.1% (basis) trifluoroacetic acid. Prior to the HPLC separation, the digest was reduced with β-mercaptoethanol for 30 minutes at 37° C. to break any disulfide bonds in the peptides. Column effluent was monitored at 215 mμ using a laboratory Data Control detector (Laboratory Data Control, Rivera Beach, Fla.). The HPLC column resolved 8 major peaks, as shown in FIG. 23A.

Each peak was first analyzed by amino acid analysis as described above to determine both the quantity and the composition of the peptides. Then, most of the peptide peaks from the HPLC column were sequenced by automated Edman degradation, using an Applied Biosystems Model 470A gas phase sequencer. Phenylthiohydantoin (PTH) amino acid derivatives were identified in a Waters HPLC system using an Altex ultrasphere C-18 column as described by Hawke et al. [Anal. Biochem. 120:302 (1982)], or in an Applied Biosystems Model 120A on-line PTH amino acid analyzer.

The amino acid sequences of some of these peptides are shown under the underlined regions of FIG. 17. The number of each of these peptides (corresponding to the HPLC peak numbers) is shown circled beside the corresponding sequence. Uncertainly in the identity of some of the residues in the peptide sequences is indicated by a question mark at those positions, although the amino acid composition analyses of the peptides showed that the amino acids indicated in the corresponding positions of the predicted sequence were present in the peptides. The uncertainly in the identity of some of the peptide residues was due to the low reactivity of tryptophan with fluorescamine.

Peptide 6, which corresponds to the N-terminus of the complete 65 kd protein, contains 4 residues at its N-terminus which are encoded by nucleotides in the expression plasmid. Analysis of peptide 8 produced an amino acid sequence similar to that of peptide 3 but lacking the 4 C-terminal residues, suggesting that it was probably the result of incomplete tryptic digestion. Peptide 5 was not sequenced, because amino acid composition analysis of this peptide showed that it was the same as peptide 6, less the first 3 amino acid residues at the N-terminus.

Figure 23B:
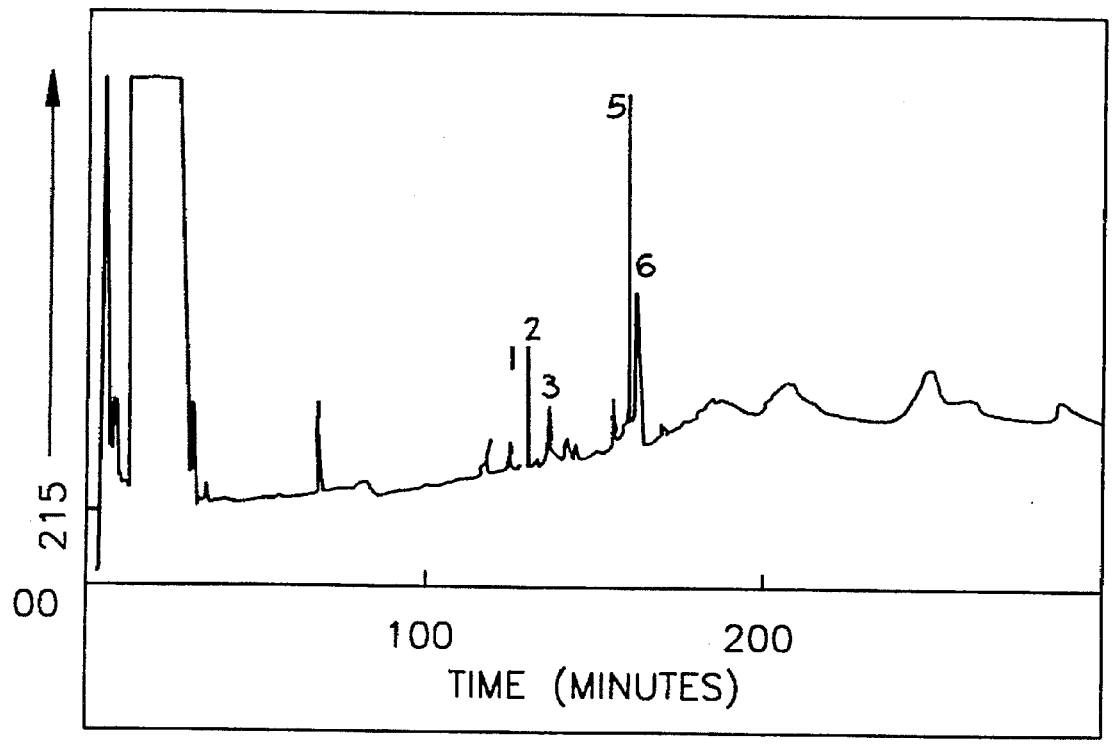

HPLC analysis of the tryptic digest carried out as described above but without prior mercaptoethanol reduction produced an elution profile in which peaks 4, 7 and 8 were absent (FIG. 23B). This observation suggests that these cysteine-containing peptides were probably involved in disulfide bond formation in the unreduced protein.

6.7. Poultry Immunization 6.7.1. Use of the 65 Kd Antigen

To determine whether administration of the purified recombinant 65 kd protein could protect chickens against challenge by *Eimeria tenella* sporulated oocysts, a series of immunization experiments was performed. In these experiments, one day to three week old Leghorn chickens (Avian Services, Frenchtown, N.J.) were maintained in a clean room and cared for by attendants who did not have contact with other birds up to the time of challenge. The birds were kept in electrically heated brooder cages until they were 3 or 4 weeks old, after which they were transferred to grow-out cages.

Non-medicated broiler starter feed and water were supplied ad libitum throughout the experiments. At the time of challenge with oocysts, the birds were transferred to another building where they were kept until the end of the experiments. The clinical conditions of the animals were checked at least three times weekly before immunization and on a daily basis after immunization. The birds were individually identified by means of wing bands at 3 or 4 weeks of age before random assignment into various test groups.

Various lots of the 65 kd protein purified by immunoaffinity chromatography as described above were used as the immunogen. These lots of immunogen contained bacterial endotoxin activity ranging from about 0.3 to about endotoxin units per µg of protein, with activity determined and defined as described in the United States Pharmacopeia, 21st Revision, 1985, United States Pharmacopeial Convention, Inc., Rockville, Md., pp. 1165–1167. The protein was dissolved in 0.02M $K_2HPO_4$ buffer, pH 6.8, before use and diluted with the same buffer as required.

Bovine serum albumin (BSA, Pentex) was used as a control. Because pyrogenic activity was present in the immunogen used, approximately equal amounts of such activity were added to all BSA controls, to account for any nonspecific effects that might be due to this activity. This pyrogenic activity was added to the BSA in the form of an untransformed E. coli lysate which was prepared by disrupting E. coli by sonication and then filtering the material through a 0.45 µ Millipore filter.

Diluted samples of control BSA or the Eimeria antigen were combined with an equal volume of adjuvants and mixed thoroughly in glass syringes fitted with 18 gauge needles prior to administration. Freund's complete and incomplete adjuvant were used for primary and booster immunizations, respectively. Both adjuvants were obtained from GIBCO, Grand Island, N.Y.

Primary immunizations were made subcutaneously on the posterior portion of the body at the base of the neck, when the birds were 4 weeks old. Some birds also received booster immunizations at 6 weeks of age. The volume of injected material ranged from about 0.4 to 2.4 ml. For the larger volumes, the dose was divided between 2 injections. Two or three weeks after the last vaccination, birds were challenged with 25,000 or 50,000 sporulated oocysts of E. tenella, administered orally. Seven days post infection, the surviving birds were sacrificed, necropsied and scored for gross lesions. All birds that died during the experiments were also necropsied. Diagnoses were made, and the intestinal lesions were scored as 0=normal, 1=slight infestation, 2=moderate infestation, 3=severe infestation and 4=death. The readings obtained were summarized as the average degree of infection for each group of birds. The birds were also weighed at the time of infection and 7 days post infection. Some birds were not vaccinated with BSA or coccidial antigen but were treated as infected or uninfected, unvaccinated controls.

The results of two such experiments are shown in Table 4.

TABLE 4

EFFECT OF SUBCUTANEOUS IMMUNIZATION OF CHICKS GIVEN ONE OR TWO VACCINATIONS WITH PURIFIED RECOMBINANT 65 KD ANTIGEN

| No. Birds | Treatment[a] | Dose (µg) at Age 4 Weeks | Dose (µg) at Age 6 Weeks | Lesion Score[b] | Weight Gain/Loss[c] (grams) |
|---|---|---|---|---|---|
| | | Experiment 1 | | | |
| 10 | IUC | — | — | 2.8 | −25 |
| 8 | Antigen | 3.15 | — | 2.4 | −44 |
| 10 | Antigen | 12.25 | — | 2.5 | −10 |
| 6 | BSA | 17.5 | — | 3.0 | +40 |
| 10 | UUC | — | — | 0 | +107 |
| 10 | IUC | — | — | 2.9 | −40 |
| 8 | Antigen | 3.15 | 1.6 | 2.0[e] | −15 |
| 10 | Antigen | 17.5 | 13.2 | 1.8[e] | +5 |
| 8 | BSA | 12.25 | 13.2 | 2.5 | −13 |
| 10 | UUC | — | — | 0 | +87 |
| | | Experiment 2 | | | |
| 8[d] | IUC | — | — | 2.6 | −11 |
| 10 | Antigen | 4 | — | 2.2 | +65 |
| 10 | Antigen | 20 | — | 2.0 | +19 |
| 9 | Antigen | 100 | — | 2.9 | +14 |
| 10 | BSA | 100 | — | 2.4 | −7 |
| 10 | IUC | — | — | 2.5 | +15 |
| 10 | Antigen | 4 | 4 | 2.1 | +35 |
| 10 | Antigen | 20 | 20 | 2.0 | +74 |
| 8 | Antigen | 100 | 100 | 2.1 | +81 |
| 10 | BSA | 100 | 100 | 2.4 | +69 |
| 4 | UUC | — | — | 0 | −3 |

[a]IUC, Antigen, BSA and UUC refer to infected (with oocysts) unimmunized controls, purified 65 kd protein, bovine serum albumin and uninfected unimmunized controls, respectively.
[b]In Experiment 1, birds given a single immunization were challenged 3 weeks later with 50,000 sporulated oocysts of E. tenella; those given a booster vaccination were challenged 2 weeks after that with 25,000 of the oocysts. In Experiment 2, the timing of oocyst challenges was the same, but 25,000 oocysts were given to both singly vaccinated and boosted birds. Infected unimmunized controls were maintained for each experiment and given identical numbers of sporulated oocysts at the same age, seven days prior to sacrifice. Results are based on a score of 0–4, as described in the text.
[c]Values shown are the difference between weight at time of infection and weight 7 days post infection.
[d]This group originally contained 9 birds, but one died after 1 week.
[e]$P \leq 0.05$ compared to IUC.

The data of Table 4 show that vaccination with the 65 kd protein generally produced numerically lower lesion scores, compared to infected but unimmunized controls. Two groups of birds given booster vaccinations in Experiment 1 (denoted by superscript e in the Table) showed reduced lesion scores that were statistically significant. In other cases, the degree of reduction in lesion scores was not as great, but weight gain was nevertheless generally improved in the vaccinated birds.

To determine whether a third vaccination would further enhance protection, an experiment was carried out in which groups of 8 birds were treated as infected or uninfected, unvaccinated controls or vaccinated with BSA or the merozoite protein at 3 and 5 weeks of age or at 3, 5 and 7 weeks of age. The first two vaccinations were made with Freund's complete adjuvant. Where a third vaccination was given, it was given with Freund's incomplete adjuvant. Inoculations were given subcutaneously as described above.

Two weeks after the last vaccination, each bird was challenged with 25,000 sporulated oocysts of E. tenella by the oral route. Body weights were measured at the time of challenge and 7 days thereafter, at which time the birds were sacrificed and cecal lesions were scored. The results are shown in Table 5.

TABLE 5

EFFECT OF SUBCUTANEOUS IMMUNIZATION OF CHICKS GIVEN TWO OR THREE VACCINATIONS WITH PURIFIED RECOMBINANT 65 KD ANTIGEN

| Treatment[a] | Dose (mg) at Age | | | Lesion Score[b] | Weight Gain/Loss[c] (grams) |
|---|---|---|---|---|---|
| | 3 Weeks | 5 Weeks | 7 Weeks | | |
| IUC | — | — | — | 2.13 | +59 |
| Antigen | 4 | 4 | — | 1.75 | +122 |
| Antigen | 4 | 4 | — | 2.88 | +128 |
| Antigen | 20 | 20 | — | 1.88 | +87 |
| Antigen | 20 | 20 | — | 1.88 | +69 |
| BSA | 20 | 20 | — | 3.13 | +106 |
| BSA | 20 | 20 | — | 2.38 | +131 |
| UUC | — | — | — | 0 | +131 |
| IUC | — | — | — | 2.25 | +23 |
| Antigen | 4 | 4 | 4 | 2.25 | +91 |
| Antigen | 20 | 20 | 20 | 2.25 | +86 |
| BSA | 20 | 20 | 20 | 1.75 | +78 |

[a]IUC, Antigen, BSA and UUC refer to infected (with oocysts) unimmunized controls, purified 65 kd protein, bovine serum albumin and uninfected unimmunized controls, respectively.
[b]Birds were challenged 2 weeks after the last vaccination with 25,000 *E. tenella* sporulated oocysts, or seven days prior to sacrifice for infected unimmunized controls. These controls were seven and nine weeks old for double and triple immunization studies, respectively, when infected. Results are based on a score of 0–4, as described in the text.
[c]Values shown are the difference between weight at time of infection and weight 7 days post infection.

The data in Table 5 show that immunity was not improved by administering a third vaccination. Greater protection, as shown by reduced cecal lesion scores, was conferred by the antigen, compared to untreated infected controls or birds vaccinated with BSA.

To determine whether routes of administration other than subcutaneous injection might produce better results, two dosage levels of the 65 kd protein were administered three times, two weeks apart, to groups of 8 3-week-old Leghorn chicks, using intradermal, subcutaneous, intramuscular, oral and anal routes of administration. Two weeks after the last immunogen administration, the birds were challenged with 25,000 sporulated oocysts of *Eimeria tenella* given orally. The birds were sacrificed one week after challenge, and cecal lesion scores were determined.

Subcutaneous injections were administered as described above. Intramuscular injections were made deeply into the exterior side of the left thigh. Intradermal injections were administered into the anterior side of the right wing. Oral administration was delivered using a 5 cm long 18 gauge ball-tipped needle, depositing the inoculum into the crop of the bird. Anal administration was made using a 5 cm long 18 gauge olive-tipped needle, introduced to its maximum length into the cloacal opening. After oral and anal administration, the birds were held in standing and inverted positions, respectively, for several minutes, to avoid possible expulsion of the inoculum.

The subcutaneous dosage form was as described above, with Freund's complete adjuvant used for the primary injection and Freund's incomplete adjuvant used for the booster injections. Dosage forms for the other routes of administration contained protein at the indicated levels in 0.02M $K_2HPO_4$ buffer, pH 6.8.

The results of this experiment are shown in Table 6.

TABLE 6

EFFECT OF VARIOUS ROUTES OF ADMINISTRATION ON CHICK VACCINATION WITH THE 65 KD ANTIGEN

| Treatment/ Route[a] | Dose (μg) at Age | | | Lesion Score[b] | Weight Gain/Loss[c] (grams) |
|---|---|---|---|---|---|
| | 3 weeks | 5 Weeks | 7 Weeks | | |
| IUC | — | — | — | 2.9 | +58 |
| Antigen/SC | 5 | 5 | 5 | 2.3 | +66 |
| Antigen/SC | 25 | 25 | 25 | 2.8 | +68 |
| BSA/SC | 25 | 25 | 25 | 2.8 | +47 |
| Antigen/IM | 5 | 5 | 5 | 2.3 | +33 |
| Antigen/IM | 25 | 25 | 25 | 2.3 | +72 |
| Antigen/A | 5 | 5 | 5 | 2.5 | +53 |
| Antigen/A | 25 | 25 | 25 | 2.6 | +50 |
| Antigen/O | 5 | 5 | 5 | 1.8[d] | +67 |
| Antigen/O | 25 | 25 | 25 | 2.5 | +87 |
| Antigen/ID | 5 | 5 | 5 | 2.1 | +26 |
| Antigen/ID | 25 | 25 | 25 | 1.9[d] | +114 |
| UUC | — | — | — | 0 | +114 |

[a]IUC, Antigen, BSA and UUC refer to infected (with oocysts) unimmunized controls, purified 65 kd protein, bovine serum albumin and uninfected unimmunized controls, respectively. SC, IM, A, O and ID refer to subcutaneous, intramuscular, anal, oral and intradermal routes of administration, respectively.
[b]Birds were challenged 2 weeks after the last vaccination with 25,000 *E. tenella* sporulated oocysts, or seven days prior to sacrifice for infected unimmunized controls. These controls were 9 weeks old when infected. Results are based on a score of 0–4, as described in the test.
[c]Values shown are the difference between weight at time of infection and weight 7 days post infection.
[d]$p < 0.05$ compared to IUC.

Table 6 shows that the lowest cecal lesion scores were observed in birds immunized with 5 μg of antigen by the oral route and with 25 μg of antigen by the intradermal route. These results were statistically significant. Numerically lower lesion scores were seen for other routes of administration and other dosage levels, indicating a protective trend. The differences between these scores and those of the IUC birds, however, were not statistically significant.

Failure to observe linear dose responses in the foregoing experiments may have been due to differences in trace contaminants and/or pyrogenic content in the 65 kd antigen preparations, or to other factors.

6.7.2. Vaccinia Vector Vaccination

To produce a more effective means of immunizing chicks with the *E. tenella* antigens of this invention, the 1.1 kb cDNA encoding the 20 kd protein recognized by monoclonal antibody 6A5 (FIG. 14) and the 1.1 kb cDNA molecule encoding the 28 kd protein recognized by monoclonal antibody 8A2 (FIG. 29) were cloned into vaccinia virus and used to vaccinate chicks, as described below.

6.7.2.1. Vector Preparation

All recombinants made were based on homologous recombination into the viral thymidine kinase (TK) locus as described by Mackett et al. [Proc. Natl. Acad. Sci. USA 79:7415 (1982)]. The TK locus has been mapped to the vaccinia virus (W) HindIII J fragment [Hruby et al., J. Virol. 43:403 (t982)], and part of this fragment has been sequenced [Weir et al., J. Virol. 46:530 (1983)].

To construct a vector for recombination, the W HindIII J fragment was subcloned into pUCB (FIG. 24a). This construct was cleaved with HpaII. The fragments were treated with *E. coli* DNA polymerase Klenow fragment (Klenow) and recleaved with HindIII, and the piece containing the viral TK gene was isolated from low melting agarose. The isolated fragment was ligated into the HindIII and blunt ended (S1 treatment) EcoRI site of a pUC8 vector (FIG. 24b, right). Subsequently, the HindIII site was eliminated by treating the HindIII digested DNA with Klenow and religating the vector fragment. For the insertion of the VV promoter (designated the 7.5K promoter), the vector was cleaved by ClaI and EcoRI.

The VV 7.5K promoter is located in one of the smallest SalI fragments of the virus [Venkatesan et al., Cell 25:805 (1981)]. The corresponding fragment was cloned into M13mp8. A clone was selected in which the direction of transcription was toward the EcoRI site of M13mp8 (FIG. 24a, left). The DNA was cleaved with ScaI and SmaI, BglII linkers were added and the DNA was religated (FIG. 24b). The EcoRI-AccI fragment containing the viral promoter segment was isolated from the M13 construct and ligated into the pUC8-TK fragment described above. This new vector was digested with BglII and EcoRI.

To create a vector with multiple cloning sites, an appropriate polylinker was included in the above construct. For this purpose the polylinker contained in the M13tg131 (Amersham) was chosen (FIG. 24d). The polylinker fragment was isolated by digesting the phage DNA with BglII and EcoRI, and the fragment was inserted into the pUC8-TK-7.5K construct, resulting in the final basic vector for recombination of foreign antigens into vv (FIG. 24c).

The EcoRI fragment coding for the 28 kd protein which binds to monoclonal antibody 8A2 does not contain the sequence for the N-terminal part of the protein. The original start codon and the leader sequence for the protein are missing.

To compensate for these missing regions, two different constructs were made and tested for expression. In the first construct, an in-frame start codon was generated by deleting part of the polylinker in the recombination vector. The vector was digested with EcoEV and SmaI, deleting part of the polylinker (FIG. 24*d*), and then religated. By this manipulation, the ATG codon contained in the SphI restriction site was placed in the correct reading frame for the coding region of the oocyst protein on the EcoRI fragment. The successful manipulation was confirmed by sequencing the new polylinker fragment.

To compensate in the DNA sequence not only for the start codon but also for the missing leader sequence, the EcoRI fragment was placed in the correct reading frame behind a leader sequence of a malarial antigen. The malarial antigen used to isolate the leader sequence was the 190 kd protein described as Ro-33 [Certa et al., EMBO J. 6:4137 (1987)]. It must be noted, however, that other leader sequences such as coccidial leader sequences could be used for the same purpose.

To isolate the DNA fragment containing the leader sequence, the Ro-33 DNA was digested with DraI. The fragment containing the recognition sites for the restriction enzymes PvuII and HindIII was isolated and digested with HindIII. The original vector construct (FIG. 10*c*) was cleaved with SalI, treated with Klenow and then digested with HindIII. In this vector fragment, the isolated DraI-HindIII malarial antigen leader fragment was cloned. This construct was used to express a fusion protein between the *F. falciparum* 190 kd protein and the *E. tenella* antigen recognized by antibody 8A2 and encoded by the EcoRI fragment.

The EcoRI fragment encoding the 28 kd protein was cloned into the EcoRI site of the polylinker contained in the basic vector (FIG. 24*c*). Constructs containing the fragment in the correct orientation were propagated and used for recombination into the vaccinia virus.

Because of the way that the initiation site for translation of the fragment was engineered into the basic vector (see above), two different N-terminal sequences were expected for the gene to be expressed by the recombinant vaccinia virus (FIG. 25). While only 3 additional amino acids (Met, Arg, and Trp) are added to the original sequence in the first construct (FIG. 25A), in the second a total of 47 amino acids are fused to the N-terminus of the polypeptide (FIG. 25B). By processing at the potential cleavage site of the leader sequence, 19 of the additional amino acids are removed, leading to a maturated protein starting with Val, Thr, His.

The EcoRI fragment coding for the 20 kd protein recognized by monoclonal antibody 6A5 contains the entire sequence. This fragment, without further manipulation, was cloned into the EcoRI site of the W vector as described above.

Recombination of the above genes coding for coccidial antigens into a strain WE vaccinia virus was carried out using a two-step procedure for selection of the recombinant virus.

In the first step, CV1 monkey cells were grown in medium I [Eagle's Minimal Essential Medium (MEM), 5% fetal calf serum (FCS: from Amimed), Penicillin/Streptomycin (100 units/ml and 100 μg/ml, respectively) and 2 mM glutamine: all reagents from Gibco] in 8 $cm^2$ culture plates to 80–90% confluency. The medium was removed and replaced with 0.2 ml of a virus suspension containing the temperature sensitive vaccinia virus strain ts N7 [Drillen et al., Virology 131:385 (1983)] at 0.1 plaque forming units (pfu)/cell. The plates were left at room temperature for 1 hour, after which 2 ml of Medium I were added to each plate and the plates were incubated for 2 hours at 33° C. (the growth permissive temperature for this virus) in a $CO_2$ incubator [Kieny et al., Nature 312:163 (1984)].

One half hour before the end of the above incubation period, a DNA-containing calcium-phosphate precipitate was prepared. This contained HeBS buffer [280 mM NaCl, 1.5 mM sodium-hydrogen-phosphate, 50 mM HEPES], 200 ng of purified vaccinia strain WR virus DNA and 200 ng of purified coccidial antigen-gene containing plasmid DNA, in a total volume of 0.55 ml. Each DNA was added in 1 μl of TE-buffer (10 mM Tris-HCl, pH 7.5, 1 mM EDTA). To this solution was added, drop-wise and with gentle swirling, 0.55 ml of a 250 mM calcium-chloride solution. This mixture was left at room temperature for 20 minutes.

After the 2 hour incubation, the medium from the culture plates was aspirated and replaced with 0.25 ml of the above DNA-containing calcium precipitate and left at room temperature for one hour. Subsequently, 2 ml of Medium I was added to each plate, and the plates were incubated for 2 hours at 39.5° C. in a 5% $CO_2$ incubator (Kieny et al., supra). At this temperature, the ts N7 virus cannot replicate, resulting in a selection for viruses which have recombined at least in the ts7 locus. Because the calcium-phosphate is eventually inhibitory to cell growth, the medium was removed after the above 2 hour incubation, and the cells were washed 3 times with 1 ml of PBS under gentle swirling. The final PBS solution was aspirated, and 2 ml of Medium I were added to each plate. Incubation at 39.5° C. in a $CO_2$ incubator was continued for 2 days.

After the two-day incubation, the culture plates with the medium and cells were placed at −30° C. for a short time and then thawed, the still attached cells were scraped from the bottom of the plate and the suspension was sonicated as described above. This homogenate was used for the second selection step.

In this step, medium from a nearly confluent lawn of human 143B TK cells (ATCC CRL 8303) growing in 8 $cm^2$ culture plates was removed and replaced with 0.2 ml of undiluted homogenate or homogenate diluted 1:5 or 1:30 (vol/vol) with PBS. Infection of the TK⁻ cells was allowed to proceed at room temperature for 1 hour.

After the incubation, 2 ml of semi-solid Medium II (Medium I with NEAA, vitamins (explain) and 1% agarose) containing 0.1 mg/ml bromodeoxyuridine (BUdR, Sigman Chemical Co. were added to the cells. The plates were then incubated for 16–24 hours at 37° C. in a $CO_2$ incubator. A second layer of semi-solid Medium II, containing 0.2% neutral red in addition to the above components, was placed over the cells and the plates were incubated for another 16–24 hours. Colorless plaques appeared which were clearly visible, and the virus was recovered as individual clones by piercing the plaque region with a Pasteur pipette (plaque purification). Virus recovered in this way was grown on CV1 cells as described above and subjected to a second and third round of plaque purification on 143B TK⁻ cells. These plaque-purified viruses were grown and purified as described above.

To test for the expression of the coccidial antigen by the recombinant virus, CV1 cells infected with recombinant virus were sedimented in a table-top centrifuge (Hettich Mikrorapid K, 100% for 3 minutes at 20° C.), and the pellet was washed twice with PBS, recentrifuged and resuspended in PBS. The cell suspension was applied to a glass microscope slide (Flow) and allowed to dry. A second method consisted of growing the CV1 cells directly on microscope slides (Miles Lab-Tek 4808), infecting the cells with virus and incubating for 1–2 days. The cells were then washed free of growth medium with PBS and allowed to dry on the slides at room temperature. To fix the cells, the slides were submerged in acetone for at least one hour at –30° C. and allowed to dry at room temperature.

Mouse anti-coccidial antigen monoclonal antibodies diluted in PBS were layered onto the microscope slides so that the cells were evenly covered with liquid. The slides were placed in a humid chamber at 37° C. for one hour and subsequently washed several times with PBS. Without allowing the slides to dry, a second antibody (FITC labeled goat anti-mouse IgG, Nordic) also diluted in PBS was layered onto the slides, and the slides were placed in a humid chamber at 37° C. for one hour to allow the antibodies to react. After several washes with PBS, the slides were allowed to dry completely. A few drops of 20% (vol/vol) glycerine in water were pipetted onto the slide, and a covet glass (Menzel 24×60) was placed on top. The fluorescence of the cell preparation was then monitored under UV light in a microscope (Zeiss ICM 405, F10 or Planapo 63 objective).

The WR strain virus can multiply in almost all cell types [Drillen et al., J. Virology 28:843 (1978)], and its multiplication can be observed directly through the formation of plaques. In most cases, however, chicken embryo fibroblast (CEF) cells were used to prepare large stocks of the virus.

To obtain CEF cells, 11-day old embryos were isolated from eggs, freed from their extremities, cut into small pieces and resuspended in a 0.25% trypsin solution (Difco) for 2 hours at room temperature. This suspension was diluted with one volume of Medium I and filtered through a cell sieve (Bellco, 150 mesh), and the cells were sedimented (Hermie table-top centrifuge, 5 minutes, 2,000 rpm, room temperature). The cell pellet was resuspended in ¼ of the original volume of Medium I and this CEF cell suspension inoculated into cell culture plates. Depending on the starting cell density, the cultures were allowed to grow 1–2 days and used for infection directly or after 1–2 further passages. A synopsis for the establishment of such primary cultures can be found in Frehney, Culture of Animal Cells, Alan R. Liss Verlag, New York 1983, Chapter 11, p. 99.

For infection, the medium was removed from 80–90% confluent CEF cells growing in 175 cm culture flasks (Falcon 3028), and the cells were incubated in a PBS solution containing virus (0.1 pfu/cell, 0.01 ml/cm²) for one hour at room temperature (20° C.) (PBS/Dulbecco, Amimed). Medium I was then added (0.2 ml/cm²), and the flasks were incubated at 37° C. for 2–3 days until about 80% of the cells had lysed. The resulting stock solution was stored directly with cells and medium in the original culture flasks at –30° C. before virus purification.

The purification steps for obtaining a virus preparation free of all host cell specific components were identical for both MVA and WR virus strains. Infected cell cultures which had been stored at –30° C. were thawed and the remaining cells were freed from the surface of the flask by shaking or scraping. The cells and virus were centrifuged out of the medium (Sorvall centrifuge, GSA rotor, 1 hour at 5,000 rpm, 10° C.). The pellet of cells and virus particles was resuspended in PBS (10–20×the volume of the pellet) and recentrifuged as above. This pellet was then resuspended in a 10-fold volume of RSB buffer (10 mM Tris-HCl, pH 8.0, 10 mM KCl, 1 mM $MgCl^2$).

To lyse the remaining intact cells and free the virus from the cell membranes, the above suspension was subjected to sonification (twice, 10 seconds at 60 watts, room temperature, Labsonic 1510 with 4 mm probe). The mixture was then centrifuged in a Sorval GSA rotor for 3 minutes at 3,000 rpm, 10° C. A virus suspension free from cell nuclei and large cell debris was thus produced. The supernatant was carefully removed, and the pellet was resuspended in RSB buffer, resonicated and centrifuged as above.

The second supernatant was combined with the first, layered onto a 10 ml 35% sucrose cushion (Fluka, in 10 mM Tirs-HCl, pH 8.0) and centrifuged for 90 minutes at 14,000 rpm in a Kontron TST 28.38/17 rotor (Beckman SW 27 analog) at 10° C. The supernatant was decanted and the pellet of virus particles was resuspended in 10 ml of 10 mM Tris-HCl, pH 8.0, sonicated to homogenize the mixture (2 times for 10 seconds at room temperature as described above) and loaded onto a step gradient for further purification.

The step gradient consisted of 5 ml aliquots of sucrose in 10 mM Tris-HCl, pH 8.0, of the following concentrations: 20%, 25%, 30%, 35% and 40%. This gradient was centrifuged in a Kontron TST 28.38/17 rotor for 35 minutes at 14,000 rpm, 10° C. Several bands containing virus particles were visible in the 30%–40% sucrose region. This region of the gradient was removed (10 ml), the sucrose solution was diluted with PBS (20 ml) and the virus particles were sedimented (Kontron rotor, 90 minutes at 14,000 rpm, 10° C.). The pellet contained almost exclusively virus particles (as judged by comparison of OD measurement and plague assay, see below). This pellet was resuspended in PBS so that the virus concentration was on the average $1-5 \times 10^9$ pfu/ml. This virus stock was used either directly or diluted with PBS.

To determine the virus concentration and the purity of the virus stock, two methods were used. The absolute concentration of virus particles was conveniently obtained by measuring the optical density (OD) of the stock solution in a spectrophotometer (Uvikon 860) at 260 nm (OD/260), where 1OD/260 equals about $1.2 \times 10^{10}$ particles per ml [Joklik, Virology 18:9 (1962)]. Virus concentration was also obtained by titrating the virus on cells (plaque assay), assuming that only one out of 60 virus particles can infect a cell.

To titer the virus concentration on cultured cells, CEF cells were grown in Medium I on 8 cm² plastic culture plates (Falcon 3001). When the cells had reached 80–90% confluency, the medium was removed, replaced with 0.2 ml of a diluted virus solution in PBS, and left at room temperature for 1 hour. The virus stock solution was diluted in 10-fold steps. After the room temperature incubation, 2 ml of semi-solid Medium I (Medium I +1% agarose) were added to each plate, and the plates were placed for 16–24 hours in a $CO_2$ incubator. Subsequently, 2 ml of semi-solid Medium I containing 0.2% neutral red (Fluka 72210) was layered on to stain the living cells, and the plates were incubated for an additional 16–24 hours. The colorless plaques were then counted under a microscope.

6.7.2.2. Chick Immunization

To determine whether vaccinia viral vectors harboring genes coding for the *E. tenella* proteins which specifically bound to monoclonal antibodies 8A2 and 6A5 could protect chicks against challenge by sporulated oocysts of a pathogenic strain of *E. tenella* (strains T2-750/7, T7-776/1 or T6-771), the following tests were carried out.

All tests were conducted using cockerels of a layer breed (Warren) supplied by the hatchery E. Wuthrich, Belp, Switzerland. Day-old chicks were reared in heated battery-brooders until the indicated ages, after which they were divided into various test groups and maintained coccidiosis-free in wire-floored cages. Throughout the tests, a commercial broiler-grower diet, based on maize, wheat and soybean meal (crude protein 21.7%) was fed.

In the first test, on day 42 chicks of equivalent weight were randomly divided into three groups of six birds each. Three days later, the chicks were immunized with either recombinant or wild type Vaccinia virus by means of two injections of 50 µl each of the respective virus suspension ($10^{10}$ pfu/ml in PBS) given subcutaneously into the right wing web. Two recombinant vaccinia viruses were used, both of which contained DNA coding for the *E. tenella* protein which specifically bound to antibody 8A2. One of the viruses (designated 37K M3) contained the leader sequence of the 190 kd malarial antigen; the other virus (designated 37K K3) lacked this leader sequence. The wild type vaccinia strain WR served as a negative control.

One week after the first injection, a booster injection was made into the left wing web of the chicks under identical conditions, using the same type of vaccinia virus used previously.

Four weeks after the first injection (day 73) the chicks were challenged with 50,000 of the sporulated oocysts. The inoculum of coccidial, which was suspended in 1 ml of physiological saline, was administered orally into the crop of the chicks by means of a blunt needle on a calibrated syringe. On day 80, all of the chicks were sacrificed, necropsied and scored for gross lesions in the ceca (score 0=normal, 1=slight infestation, 2=medium infestation, 3=severe lesions, 4=chick died from coccidiosis). The droppings were collected quantitatively over the last two days of the infectious cycle, and the number of excreted oocysts was determined in a representative sample of feces. The results are shown in Table 7.

TABLE 7

VACCINATION OF 45 DAY OLD CHICKS WITH VACCINIA VIRUSES EXPRESSING THE 28 KD PROTEIN

| Virus[a] | Number of Chicks | Cecal Lesion Score | Daily Oocyst Excretion/Chick ($\times 10^{-6}$) |
|---|---|---|---|
| 37 K3 | 6 | 1.33 | 149 |
| 37 M3 | 4[b] | 1.50 | 107 |
| Wild-Type | 6 | 2.67 | 271 |

[a]Virus 37 M3 contained the leader sequence of the 190 kd malarial antigen; virus 37 K3 did not. The wild-type virus was vaccinia strain WR.
[b]Two chicks were sacrificed prior to coccidiosis challenge.

Table 7 shows that compared to the wild-type control virus, both viruses containing DNA coding for the 28 kd protein conferred some protection against oocyst challenge, both in terms of a reduction of cecal lesion score and reduced oocyst excretion. The two viruses were equally effective, showing that the malarial leader sequence was not a factor.

In the second test, cockerels were reared and immunized as described above but beginning at day 22. A viral dose of $2 \times 10^8$ pfu in 100 µl of PBS was administered at that time. The viruses used were from different preparations of vaccinia virus containing DNA coding for the 28 kd protein without (designated 37 K5) or with (designated 37M19) the malarial leader sequence. The same wild-type strain WR virus was used as a control. Booster injections into the right wing webs at the same doses were given either one or 2 weeks after the first injections.

On day 57 (5 weeks after the first injection), all of the chicks were challenged with 50,000 of the sporulated oocysts. One week later, the chicks were sacrificed, necropsied and scored as described above. Daily weight gain following infection and oocyst excretion during the final two days were also determined. The results are shown in Table 8.

TABLE 8

VACCINATION OF 22 DAY OLD CHICKS WITH VACCINIA VIRUSES EXPRESSING THE 28 KD PROTEIN

| Virus[a] | Time to Booster (Weeks) | Number of Chicks | Daily Weight Gain (g) | Cecal Lesion Score | Daily Oocyst Excretion/ Chick ($\times 10^{-6}$) |
|---|---|---|---|---|---|
| 37 K5 | 1 | 8 | 11.45 | 2.38 | 21.0 |
| 37 M19 | 1 | 8 | 15.61 | 2.13 | 24.0 |
| Wild-Type | 1 | 8 | 8.77 | 2.50 | 33.1 |
| 37 K5 | 2 | 8 | 5.14 | 2.25 | 22.3 |
| 37 M19 | 2 | 8 | 11.79 | 2.13 | 32.7 |
| Wild-Type | 2 | 8 | 8.34 | 2.63 | 37.0 |

[a]Virus 37 M19 contained the leader sequence of the 190 kd malarial antigen. Virus 37 K5 did not. The wild-type virus was vaccinia strain WR.

Table 8 shows that, compared to the wild-type control virus, both viruses containing the coccidial DNA conferred some protection against the pathogenic oocyst challenge, in terms of weight gain, cecal lesion score and oocyst excretion. Both viruses were about equally effective. Administration of the booster 1 week after the primary injection produced somewhat better weight gain and lower oocyst excretion, but cecal lesion scores were about the same for both booster schedules.

In the third test, the effect of three vaccinations was examined. Chicks were injected (right wing web) with two 50 μl aliquots (3×10$^9$ pfu/ml) of suspensions of wild-type vaccinia virus or virus containing DNA coding for the 20 kd protein which bound specifically to monoclonal antibody 6A5, at 21 days of age. All chicks were given same dose booster injections at day 28 into the left wing webs. Some chicks were given additional same-dose booster injections into the wing webs of both sides at day 35. Other chicks were maintained with no vaccinations, as further controls.

On day 49 (4 weeks after the first injections), all of the chicks were challenged with 50,000 of the sporulated oocysts. One week later, the chicks were sacrificed, necropsied and scored for gross cecal lesions as described above. Body weight was recorded weekly for calculation of daily weight gain, and the droppings were collected over the last two days of the infectious cycle to determine oocyst excretion. The results are shown in Table 9.

protection. Therefore, the protection conferred by the virus harboring the coccidial DNA was specific and not due to a generalized immune stimulation caused by exposure to the vaccinia virus itself. Three vaccinations were more effective than two.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. An isolated and purified DNA molecule derived from Eimeria tenella, wherein the DNA molecule consists of the DNA sequence of FIGS. 20(A–D) and encodes the antigenic polypeptide consistive of the amino acid sequence of FIGS. 21(A–D).

2. An isolated and purified DNA molecule derived from Eimeria tenella, wherein the DNA molecule consists of the DNA sequence of FIG. 33 and encodes the antigenic polypeptide consisting of the amino acid sequence FIG. 34.

3. A recombinant vector comprising the DNA molecule of claim 1, which encodes the antigenic polypeptide of FIG. 21(A–D).

TABLE 9

VACCINATION OF 21 DAY OLD CHICKS WITH VACCINIA VIRUS EXPRESSING THE 20 KD PROTEIN

| Virus | No. of Injections | Number of Chicks | Daily Weight Gain (g) | Cecal Lesion Score | Oocyst Excretion/g Feces(× 10$^{-6}$) |
|---|---|---|---|---|---|
| With Coccidial DNA | 2 | 6 | 2.9 | 2.33 | 1.69 |
| With Coccidial DNA | 3 | 6 | 4.2 | 1.67 | 1.32 |
| Wild-Type | 3 | 6 | −4.1 | 2.67 | 2.09 |
| None | — | 6 | −3.8 | 2.83 | 1.75 |

The data of Table 9 show that the virus producing the coccidual antigen provided some protection against oocyst infection in terms of enhanced weight gain, reduced cecal lesion score and lowered oocyst excretion. Comparison of the results obtained with unvaccinated controls shows that vaccination with the wild-type vaccinia virus did not confer 4. A recombinant vector the DNA molecule of claim 2, which encodes the antigenic polypeptide of FIG. 34.

5. A host cell transformed with the recombinant vector of claim 3 or claim 4.

* * * * *

UNITED STATES PATENT AND TRADEMARK OFFICE
CERTIFICATE OF CORRECTION

PATENT NO. : 5,661,015
DATED : August 26, 1997
INVENTOR(S) : BINGER ET AL.

It is certified that error appears in the above-indentified patent and that said Letters Patent is hereby corrected as shown below:

<u>In Column 48:</u>

Claim 1, line 16, replace "consistive" with -- consisting --.

Claim 1, line 17, replace "(A-D)" with -- (A-C) --.

Claim 2, line 21, after "sequence" and before "FIG" insert -- of --.

Claim 3, line 23, replace "FIG." with -- FIGS. --.

Claim 3, line 24, replace "(A-D)" with -- (A-C) --.

Claim 4, line 39, after "vector" and before "the" insert -- comprising --.

Signed and Sealed this

Twenty-fifth Day of November, 1997

Attest:

BRUCE LEHMAN

*Attesting Officer*  *Commissioner of Patents and Trademarks*